United States Patent
Lahusen et al.

(10) Patent No.: US 11,352,646 B2
(45) Date of Patent: Jun. 7, 2022

(54) VECTOR SYSTEM FOR EXPRESSING REGULATORY RNA

(71) Applicant: American Gene Technologies International Inc., Rockville, MD (US)

(72) Inventors: Tyler Lahusen, Rockville, MD (US); Lingzhi Xiao, Rockville, MD (US); Charles David Pauza, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 0 days.

(21) Appl. No.: 17/289,653

(22) PCT Filed: Nov. 5, 2019

(86) PCT No.: PCT/US2019/059828
§ 371 (c)(1),
(2) Date: Apr. 28, 2021

(87) PCT Pub. No.: WO2020/097049
PCT Pub. Date: May 14, 2020

(65) Prior Publication Data
US 2021/0403949 A1    Dec. 30, 2021

Related U.S. Application Data

(60) Provisional application No. 62/755,985, filed on Nov. 5, 2018.

(51) Int. Cl.
*C12N 15/86* (2006.01)
*C12N 15/113* (2010.01)

(52) U.S. Cl.
CPC ............ *C12N 15/86* (2013.01); *C12N 15/113* (2013.01); *C12N 2310/14* (2013.01); *C12N 2740/15023* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 8,124,752 B2 | 2/2012 | Bumcrot et al. | |
| 8,287,857 B2 | 10/2012 | Dudley et al. | |
| 9,834,790 B1 | 12/2017 | Pauza et al. | |
| 9,914,938 B2 | 3/2018 | Pauza et al. | |
| 10,023,880 B2 | 7/2018 | Pauza et al. | |
| 10,036,040 B2 | 7/2018 | Pauza et al. | |
| 10,137,144 B2 | 11/2018 | Pauza et al. | |
| 10,420,789 B2 | 9/2019 | Pauza et al. | |
| 10,472,649 B2 | 11/2019 | Pauza et al. | |
| 2004/0192629 A1 | 9/2004 | Xu et al. | |
| 2004/0248296 A1 | 12/2004 | Beresford et al. | |
| 2004/0265306 A1 | 12/2004 | Arthos et al. | |
| 2005/0019927 A1 | 1/2005 | Markus et al. | |
| 2006/0057553 A1 | 3/2006 | Aguilar-Cordova | |
| 2006/0073576 A1 | 4/2006 | Barnett et al. | |
| 2006/0246520 A1 | 11/2006 | Champagne et al. | |
| 2007/0141679 A1 | 6/2007 | Sodroski | |
| 2008/0003225 A1 | 1/2008 | Vie et al. | |
| 2008/0003682 A1 | 1/2008 | Lois-Caballe et al. | |
| 2008/0153737 A1 | 6/2008 | Lieberman et al. | |
| 2008/0199961 A1 | 8/2008 | Rasko et al. | |
| 2008/0227736 A1 | 9/2008 | Chen et al. | |
| 2008/0293142 A1 | 11/2008 | Liu et al. | |
| 2009/0148936 A1 | 6/2009 | Stout et al. | |
| 2009/0304688 A1 | 12/2009 | Fournie et al. | |
| 2010/0316676 A1 | 12/2010 | Sanders | |
| 2011/0008803 A1 | 1/2011 | Stockwell et al. | |
| 2012/0027725 A1 | 2/2012 | Galvin et al. | |
| 2013/0090371 A1 | 4/2013 | Lu et al. | |
| 2013/0122380 A1 | 8/2013 | Aquino et al. | |
| 2014/0155468 A1 | 6/2014 | Gregory et al. | |
| 2014/0178340 A1 | 6/2014 | Robbins et al. | |
| 2014/0348794 A1 | 11/2014 | Chiorini et al. | |
| 2015/0010578 A1 | 1/2015 | Balazs et al. | |
| 2015/0018539 A1 | 1/2015 | Fellmann | |
| 2015/0126580 A1 | 5/2015 | DePinho et al. | |
| 2016/0060707 A1 | 3/2016 | Goldenberg et al. | |
| 2016/0243169 A1 | 8/2016 | Chen et al. | |
| 2017/0015976 A1 | 1/2017 | Nelson | |
| 2017/0335344 A1 | 11/2017 | Pauza et al. | |
| 2018/0142257 A1 | 5/2018 | Pauza | |
| 2018/0142258 A1 | 5/2018 | Pauza | |
| 2018/0195050 A1 | 7/2018 | Szalay | |

(Continued)

FOREIGN PATENT DOCUMENTS

| | | |
|---|---|---|
| CN | 101516365 | 8/2009 |
| CN | 101679466 | 3/2010 |

(Continued)

OTHER PUBLICATIONS

Davis-Gardner et al., "eCD4-Ig promotes ADCC activity of sera from HIV-1-infected patients", Department of Immunology and Microbiology, The Scripps Research Institute, PLOS Pathogen, Dec. 18, 2017, https://doi.org/10.1371/journal.ppat.1006786.
PCT; International Search Report and Written Opinion in the PCT Application No. PCT/US2021/020721 dated Jul. 21, 2021.
USPTO; Non-Final Office Action dated Jul. 20, 2021 in the U.S. Appl. No. 17/198,017.
Li et al., "Reduced Expression of the Mevalonate Pathway Enzyme Farnesyl Pyrophosphate Synthase Unveils Recognition of Tumor Cells by Vγ2Vδ2 T Cells," J. of Immunology, 2009, vol. 182, pp. 8118-8124.
Wang et al., "Indirect Stimulation of Human Vγ2Vδ2 T Cells through Alterations in Isoprenoid Metabolism," J. of Immunology, vol. 187 pp. 5099-5113, (Nov. 15, 2011).

(Continued)

*Primary Examiner* — Michael D Burkhart
(74) *Attorney, Agent, or Firm* — DLA Piper LLP (US)

(57) ABSTRACT

Viral vectors, lentiviral particles, and modified cells are disclosed. They encode or express a small RNA capable of targeting the KIF11 gene. In embodiments, the viral vectors and lenti viral particles further comprise and a KIF11 gene whose non-coding region has been modified such that it is resistant to activity by the small RNA.

8 Claims, 13 Drawing Sheets

Specification includes a Sequence Listing.

(56) References Cited

U.S. PATENT DOCUMENTS

| | | |
|---|---|---|
| 2018/0256624 A1 | 9/2018 | Pauza |
| 2018/0305716 A1 | 10/2018 | Pauza et al. |
| 2018/0355032 A1 | 12/2018 | Roberts |
| 2019/0062786 A1 | 2/2019 | Pauza et al. |
| 2019/0078096 A1 | 3/2019 | Lahusen et al. |
| 2019/0083523 A1 | 3/2019 | Pauza |
| 2019/0218573 A1 | 7/2019 | Pauza et al. |
| 2019/0388456 A1 | 12/2019 | Pauza et al. |
| 2020/0063161 A1 | 2/2020 | Pauza |
| 2020/0181645 A1 | 6/2020 | Pauza |
| 2021/0047644 A1 | 2/2021 | Lahusen |

FOREIGN PATENT DOCUMENTS

| | | |
|---|---|---|
| CN | 101805750 | 8/2010 |
| CN | 105112370 | 12/2015 |
| CN | 108883100 | 11/2018 |
| EP | 3402483 | 11/2018 |
| EP | 3426777 | 1/2019 |
| JP | 2007-527240 | 9/2007 |
| JP | 2008-538174 | 10/2008 |
| JP | 2013-530152 | 7/2013 |
| JP | 2015-518838 | 7/2015 |
| JP | 2016-502404 | 1/2016 |
| WO | 2002020554 | 3/2002 |
| WO | 2005033282 | 4/2005 |
| WO | 2006039721 | 4/2006 |
| WO | 2007000668 | 1/2007 |
| WO | 2007015122 | 2/2007 |
| WO | 2007132292 | 11/2007 |
| WO | 2008025025 | 2/2008 |
| WO | 2009100928 | 8/2009 |
| WO | 2009147445 | 12/2009 |
| WO | 2010051521 | 5/2010 |
| WO | 2010117974 | 10/2010 |
| WO | 2010127166 | 11/2010 |
| WO | 2011008348 | 1/2011 |
| WO | 2012048303 | 4/2012 |
| WO | 2012061075 | 5/2012 |
| WO | 2012145624 | 10/2012 |
| WO | 2013096455 | 6/2013 |
| WO | 2014117050 | 7/2014 |
| WO | 2014187881 | 11/2014 |
| WO | 2015017755 | 2/2015 |
| WO | 2015078999 | 6/2015 |
| WO | 2015164759 | 10/2015 |
| WO | 20170068077 | 4/2017 |
| WO | 2017123918 | 7/2017 |
| WO | 2017156311 | 9/2017 |
| WO | 20170173453 | 10/2017 |
| WO | 2018009246 | 1/2018 |
| WO | 20180148443 | 8/2018 |
| WO | 2018232359 | 12/2018 |
| WO | 2020011247 | 1/2020 |
| WO | 2020097049 | 5/2020 |
| WO | 2021178571 | 9/2021 |

OTHER PUBLICATIONS

Dieli et al., "Targeting Human γδ T Cells with Zoledronate and Interleukin-2 for immunotherapy of Hormone-Refractory Prostate Cancer," Europe PMC Funders Group, Cancer Research, vol. 67(15), pp. 7450-1451, (Aug. 1, 2007).
Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).
Miettinen et al., "Mevalonate Pathway Regulates Cell Size Homeostasis and Proteostasis Through Autophagy," Cell Reports, vol. 13(11), pp. 2610-2620, (Dec. 2015).
Tolmachov, "Designing Lentiviral Gene Vectors," Viral Gene Therapy, Chapter 13, pp. 263-284, (2011).
Z. Li, "Inhibition of farnesyl pyrophosphate synthase prevents angiotensin II-induced cardiac fibrosis in vitro," Clinical & Experimental Immunology, (2014).
Xiaofeng Jiang, "A novel EST-derived RNAi screen reveals a critical role for farnesyl diphosphate in B2-adrenerigic receptor internalization and down-regulation," The FASEB Journal, vol. 26, pp. 1-13(1995).
Jian Yang, "Lentiviral-Mediated Silencing of Farnelsyl Pyrophosphate Synthase through RNA Interference in Mice," Biomed Research International, vol. 2015, Article ID 914026, 6 pages, (2015).
Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).
Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).
Nada et al., "Enhancing adoptive cancer immunotherapy with Vγ2Vδ2 T cells through pulse zoledronate stimulation", Journal for Immunotherapy of Cancer, vol. 5, No. 1, (Feb. 21, 2017), pp. 1-23, (2017) DOI 10.1186/s40425-017-0209-6 *the whole document*.
Benyamine et al., "BTN3A molecules considerably improve Vγ9Vδ2T cells-based immunotherapy in acute myeloid leukemia," Oncolmmunology, vol. 5, No. 10, 10 pages, (Oct. 2, 2016), E1146843 *the whole document*.
Harly et al., "Key implication of CD277/butyrophilin-3 (BTN3A) in cellular stress sensing by a major human γδ T-cell subset," American Society of Hematology, vol. 120, No. 11, (Sep. 13, 2012), pp. 2269-2279, XP055081172, ISSN: 0006-4971, DOI: 10.1182/blood-2012-05-430470 *the whole document*.
Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.
Ostertag et al., "Brain Tumor Eradication and Prolonged Survival from Intratumoral Conversion of 5-Fluorocytosine to 5-fluorouracil Using a Nonlytic Retroviral Replicating Vector," Neuro-Oncology 14(2), pp. 145-159, Feb. 2012.
Twitty et al., "Retroviral Replicating Vectors Deliver Cytosine Deaminase Leading to Targeted 5-Fluorouracil-Mediated Cytotoxicity in Multiple Human Cancer Types, Human Gene Therapy Methods", 27(1), pp. 17-31, Feb. 1, 2016.
Hassan et al., "Isolation of umbilical cord mesenchymal stem cells using human blood derivative accompanied with explant method," Stem Cell Investigation, pp. 1-8, (2019).
Huang et al., "An Efficient protocol to generate placental chorionic plate-derived mesenchymal stem cells with superior proliferative and immunomodulatory properties," Stem Cell Research & Therapy, pp. 1-15, (2019).
Thompson et al., "Alkylamines cause Vγ9Vδ2 T-cell activation and proliferation by inhibiting the mevalonate pathway," Blood, Jan. 15, 2006, vol. 107, pp. 651-654.
Gober et al.,"Human T Cell Receptor γδ Cells Recognize Endogenous Mevalonate Metabolites in Tumor Cells," J. of Experimental Med., Jan. 20, 2003, vol. 197, pp. 163-168.
Human papillomavirus type 16 (HPV16), complete genome; GenBank: K02718.1; Publication [online]; Mar. 18, 1994, https://www.ncbi.nlm.nih.gov/nucleotide/333031?report=genbank&log$=nucltop&blast_rank=22&RID=H3E1THFU014; pp. 1-4.
{Long control region} [human papillomavirus, type 16, Genomic, 860 nt]; Accession S60559. Publication [online]. May 7, 1993, https://www.ncbi.nlm.nih.gov/nucleotide/237343?report=genbank&log$=nucltop&blast_rank=1&RID=H3FCKA00014; pp. 1.
Stunkel et al., "The Chromatin Structure of the Long Control Region of Human Papillomavirus Type 16 Repress Viral Oncoprotein Expression," Journal of Virology, vol. 73, No. 3, pp. 1918-1930 (Mar. 1999).
Lu et al., "Anti-Sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088 (Jul. 2004).

(56) References Cited

OTHER PUBLICATIONS

GenBank Accession No. JG619773, MNESC1NG-T3-001_L15_6FEB2009_054 MNESC1NG cell culture from Mahonia nervosa Berberis nervosa cDNA, mRNA sequence, Feb. 13, 2014 (online). [Retrieved on Dec. 5, 2017], Retrieved from the internet:<URL: https://www.ncbi.nlm.nih.gov/nucest/JG619773 > entire document.
Moser et al., "γδ T cells: novel initiators of adaptive immunity," Immunological Reviews, vol. 215, pp. 89-102 (Feb. 2, 2007).
Capietto, A. H. et al., "Stimulated γδ T Cells Increase the in Vivo Efficacy of Trastuzumab in HER-2+ Breast Cancer," J Immunology, vol. 187(2), pp. 1031-1038, (2011).
Chen, Z. and M. S. Freedman, "CD 16+ γδ T Cells Mediate Antibody Dependent Cellular Cytotoxicity: Potential Mechanism in the Pathogenesis of Multiple Sclerosis," Clin Immunology, vol. 128(2), pp. 219-227, (2008).
Couzi, L. et al., "Antibody-Dependent Anti-Cytomegalovirus Activity of Human γδ T Cells Expressing CD16 (FcγRIIIa)," Blood, vol. 119(6), pp. 1418-1427, (2012).
Fisher, J. P. et al., "Effective Combination Treatment of GD2-Expressing Neuroblastoma and Ewing's Sarcoma Using Anti-GD2 ch14.18/CHO Antibody with Vγ9Vδ2+γδT Cells," OncoImmunology, vol. 5(1), pp. e1025194, (2016).
Gertner-Dardenne, J. et al., "Bromohydrin pyrophosphate enhances antibody-dependent cell-mediated cytotoxicity induced by therapeutic antibodies," Blood 113(20): 4875-4884, (2009).
Poonia, B. and C. D. Panza, "Gamma delta T cells from HIV+ donors can be expanded in vitro by zoledronate/interleukin-2 to become cytotoxic effectors for antibody-dependent cellular cytotoxicity," Cryotherapy 14(2): 173-181, (2012).
Schiller, C. B. et al., "CD19-Specific Triple body SPM-1 Engages NK and γδ T Cells for Rapid and Efficient Lysis of Malignant B-Lymphoid Cells," Oncotarget, vol. 7(50), pp. 83392-83408, (2016).
Tokuyama, H. et al., "Vγ9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).
Oh et al. "Lentiviral Vector Design Using Alternative RNA Export Elements," Retrovirology, vol. 4:38, pp. 1-10, (2007).
Ding et al., "Administration-Route and Gender-Independent Long-term Therapeutic Correction of Phenylketonuria (PKU) in a Mouse Model by Recombinant Adeno-Associated Virus 8 Pseudo typed Vector-Mediated Gene Transfer," Gene Therapy, vol. 13, pp. 583-587, (Dec. 1, 2005).
Nowacki et al., "The PAH Mutation Analysis Consortium Database: Update 1996," Nucleic Acid Research, vol. 25(1), pp. 139-142, (Jan. 1, 1997).
Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).
Wang et al., "Butyrophilin 3 A1 Plays an Essential Role in Prenyl Pyrophosphate Stimulation of Human Vg2Vd2 T Cells," Journal of Immunology, vol. 191(3), pp. 1029-1042, (Jul. 5, 2013).
Hee Yeon Kim., "Farnesyl diphosphate synthase is important for the maintenance of glioblastoma stemness," Experimental & Molecular Medicine, (2018).
Hong Wang., "Indirect Stimulation of Human V2V2 Cells Through Alterations in Isoprenoid Metabolism," The Journal of Immunology, (2011).
Daryl S. Schiller, ""Parameters Influencing Measurement of the Gag Antigen-Specific T-Proliferative Response to HIV Type 1 Infection,"" AIDS Research and Human Retroviruses, vol. 16, No. 3, pp. 259-271, (2000).
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT; International Search Report dated Nov. 9, 2018 in Application No. PCT/US2018/037924.
PCT; Written Opinion dated Nov. 9, 2018 in Application No. PCT/US2018/037924.
USPTO; Notice of Allowance dated Oct. 13, 2017 in U.S. Appl. No. 14/706,481.
USPTO; Notice of Allowance dated Nov. 2, 2017 in U.S. Appl. No. 15/652,080.
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Notice of Allowance dated Apr. 23, 2018 in U.S. Appl. No. 15/850,937.
USPTO; Notice Allowance dated Apr. 26, 2018 in U.S. Appl. No. 15/849,062.
USPTO; Non-Final Office Action dated Jun. 15, 2018 in U.S. Appl. No. 15/904,131.
USPTO; Non-Final Office Action dated Dec. 31, 2018 in U.S. Appl. No. 16/182,443
USPTO; Final Office Action dated May 2, 2019 in U.S. Appl. No. 16/182,443.
USPTO; Non-Final Office Action dated May 7, 2019 in U.S. Appl. No. 16/008,991.
USPTO; Non-Final Office Action dated May 16, 2019 in U.S. Appl. No. 16/132,247.
USPTO; Notice of Allowance dated Jun. 18, 2019 in the U.S. Appl. No. 16/182,443.
USPTO; Notice of Allowance dated Jul. 3, 2019 in U.S. Appl. No. 16/182,443.
USPTO; Notice of Allowance dated Aug. 14, 2019 in the U.S. Appl. No. 16/008,991.
USPTO; Final Office Action dated Jul. 1, 2019 in the U.S. Appl. No. 16/132,247.
USPTO; Notice of Allowance dated Jul. 19, 2019 in the U.S. Appl. No. 16/132,247.
USPTO; Restriction Requirement dated Nov. 7, 2019 in the U.S. Appl. No. 16/083,384.
USPTO; Non-Final Office Action dated Mar. 16, 2020 in the U.S. Appl. No. 16/083,384.
USPTO; Notice of Allowance dated May 18, 2020 in the U.S. Appl. No. 16/083,384.
USPTO; Non-Final Office Action dated Jun. 1, 2020 in the U.S. Appl. No. 16/530,908.
USPTO; Notice of Allowance dated Jul. 10, 2020 in the U.S. Appl. No. 16/530,908.
USPTO; Non-Final Office Action dated Nov. 25, 2020 in the U.S. Appl. No. 16/943,800.
USPTO; Restriction Requirement dated Dec. 8, 2020 in the U.S. Appl. No. 16/563,738.
USPTO; Notice of Allowance dated Feb. 10, 2021 in the U.S. Appl. No. 16/943,800.
USPTO; Non-Final Office Action dated Mar. 12, 2021 in the U.S. Appl. No. 16/563,738.
USPTO; Invitation to Pay Additional Fees and, Where Applicable, Protest Fee dated Sep. 11, 2018 in Application No. PCT/US2018/37924.
JP: Japanese Office Action in the Application No. 2018-536892 dated Jun. 26, 2020.
JP: Final Office Action in the JP Application No. 2018-536892 dated Nov. 16, 2020.
CN; 1st Office Action in the CN Application No. 202010396594.8 dated Jan. 15, 2021.
EP; Supplementary Search Report in the EP Application No. 18817253 dated Feb. 10, 2021.
JP: Office Action in the JP Application No. 2018-547354 dated Feb. 16, 2021.
EPO: Extended Search Report dated Jun. 6, 2019 in EP Application No. 17739028.3.
CN; 1st Office Action in the CN Application No. 20170017712.6 dated May 8, 2020.
EPO: European Search Report dated Aug. 12, 2019 in the EP Application No. 17764128.9.

(56) References Cited

OTHER PUBLICATIONS

Chen et al., "An unconventional Trail to cancer therapy", Eur J Immunol, 2013, 43: 3159-3162.
Riaño et al., "Vγ9Vδ2 TCR-activation by phosphorylated antigens requires butyrophilin 3 AI (BTN3A1) and additional genes on human chromosome 6", EurJ Immunol, 2014, 44: 2571-2576.
US Non-Final Office Action in U.S. Appl. No. 16/614,682, dated Feb. 28, 2022, 75 pages.

AGT Helper plus Rev plasmid

AGT Envelope plasmid

Lentiviral vector expressing shKIF11 and KIF11

RSV – 5' LTR – Psi – RRE – cPPT – H1 – shKIF11 (UTR) – CMV – KIF11 – WPRE – ΔU3 3' LTR

FIG. 4

VECTOR SYSTEM FOR EXPRESSING REGULATORY RNA

CROSS-REFERENCE TO RELATED APPLICATION

This application claims priority to: U.S. Provisional Patent Application No. 62/755,985, filed on Nov. 5, 2018, entitled "VECTOR SYSTEM FOR EXPRESSING REGULATORY RNA," the disclosure of which is incorporated herein by reference.

FIELD

The present disclosure relates generally to the field of gene therapy, specifically in relation to the use of vectors and modified cells that encode or express regulatory RNA.

BACKGROUND

Malignant or neoplastic cells may be controlled by regulatory RNA and especially inhibitory RNA (RNAi) capable of blocking critical mechanisms of cell growth. In part, because they produce RNAi, Mesenchymal Stem Cells (MSC) are used increasingly for cellular therapies and are envisioned as cellular delivery vehicles for cancer treatment. MSC also produce immune-inhibiting cytokines including TGF-ß and have a short half-life in vivo, making them good candidates for allogeneic cell therapy. Further, MSC express genes of the Connexin family that create a plasma membrane pore capable of interacting with connexin pores on tumor cell membranes. These pores allow exchange of cytoplasmic materials including RNAi, and may be exploited to deliver growth-inhibiting RNAi into tumor cells. MSC therapy is used currently for regenerative medicine and to combat autoimmune or inflammatory diseases.

SUMMARY

In an aspect, a viral vector is provided comprising a first nucleotide sequence encoding a small RNA capable of binding a non-coding region of a host copy of KIF11.

In embodiments, the non-coding region of the host copy of KIF11 is a 3' untranslated region or a 5' untranslated region. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the viral vector further comprises a second nucleotide sequence encoding a KIF11 gene or a variant thereof, wherein the KIF11 gene or the variant thereof lacks at least one sequence portion. In embodiments, the sequence portion comprises a coding region or a non-coding region of the KIF11 gene or variant thereof. Where the sequence portion comprises a non-coding region, the sequence portion may comprise at least one of a 5' untranslated region or a 3' untranslated region of the KIF11 gene or variant thereof.

In another aspect, a lentiviral particle produced by a packaging cell and capable of infecting a target cell is provided, wherein the lentiviral particle comprises an envelope protein capable of infecting the target cell; and a first nucleotide sequence encoding a small RNA capable of binding a non-coding region of a host copy of KIF11.

In embodiments, the non-coding region is a 3' untranslated region or a 5' untranslated region of the host copy of KIF11. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the lentiviral particle further comprises a second nucleotide sequence encoding a KIF11 gene or a variant thereof, wherein the KIF11 gene or the variant thereof lacks at least one sequence portion. In embodiments, the sequence portion comprises a coding region or a non-coding region of the KIF11 gene or variant thereof. Where the sequence portion comprises a non-coding region, the sequence portion may comprise at least one of a 5' untranslated region or a 3' untranslated region of the KIF11 gene or variant thereof. In embodiments, the target cell is a mesenchymal stem cell.

In another aspect, a modified mesenchymal stem cell is provided comprising a mesenchymal stem cell infected with a lentiviral particle, wherein the lentiviral particle comprises: an envelope protein capable of infecting the mesenchymal stem cell; and a first nucleotide sequence encoding a small RNA capable of binding a non-coding region of a host copy of KIF11.

In embodiments, the non-coding region is a 3' untranslated region or a 5' untranslated region of the host copy of KIF11. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the first nucleotide sequence is present in the modified mesenchymal stem cell at between about 1 and about 10 copies per cell.

In embodiments, the lentiviral particle further comprises a second nucleotide sequence encoding a KIF11 gene or a variant thereof, wherein the KIF11 gene or the variant thereof lacks at least one sequence portion. In embodiments, the sequence portion comprises a coding region or a non-coding region of the KIF11 gene or variant thereof. Where the sequence portion comprises a non-coding region, the sequence portion may comprise at least one of a 5' untranslated region or a 3' untranslated region of the KIF11 gene or variant thereof.

In another aspect, a method of producing a modified mesenchymal stem cell is provided, the method comprising: infecting a mesenchymal stem cell with an effective amount of a lentiviral particle, wherein the lentiviral particle comprises: an envelope protein capable of infecting the mesenchymal stem cell; and a first nucleotide sequence encoding a small RNA capable of binding a non-coding region of a host copy of KIF11.

In embodiments, the non-coding region is a 3' untranslated region or a 5' untranslated region of the host copy of KIF11. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the first nucleotide sequence is present in the modified mesenchymal stem cell at between about 1 and about 10 copies per cell.

In embodiments, the lentiviral particle further comprises a second nucleotide sequence encoding a KIF11 gene or a variant thereof, wherein the KIF11 gene or the variant thereof lacks at least one sequence portion. In embodiments, the sequence portion comprises a coding region or a non-coding region of the KIF11 gene or variant thereof. Where the sequence portion comprises a non-coding region, the sequence portion may comprise at least one of a 5' untranslated region or a 3' untranslated region of the KIF11 gene or variant thereof.

In another aspect, a method of treating cancer in a subject is provided. The method comprises administering a therapeutically-effective amount of any modified mesenchymal stem cell described herein to the subject. In embodiments, the modified mesenchymal stem cell is allogeneic to the subject. In embodiments, the modified mesenchymal stem cell is autologous to the subject. In embodiments, the cancer is selected from any one or more of a carcinoma, a sarcoma, a myeloma, a lymphoma, a mixed type, or a mixture of the foregoing.

In another aspect a use of the modified mesenchymal stem cell to treat cancer is provided comprising any of the modified mesenchymal stem cells described herein.

In another aspect, a method of treating cancer in a subject is provided, the method comprising administering a therapeutically effective amount of any lentiviral particle described herein to the subject.

In embodiments, the cancer is selected from any one or more of a carcinoma, a sarcoma, a myeloma, a lymphoma, a mixed type, or a mixture of the foregoing. In embodiments, the lentiviral particle is administered to the subject via an infected target cell. In embodiments, the target cell comprises a somatic cell. In embodiments, the somatic cell comprises a hepatocyte or a lymphocyte. In embodiments, the somatic cell comprises a lymphocyte, wherein the lymphocyte comprises a tumor specific T cell. In embodiments, the target cell comprises a stem cell. In embodiments, the stem cell comprises an induced pluripotent stem cell or a mesenchymal stem cell.

BRIEF DESCRIPTION OF THE DRAWINGS

FIG. 4 depicts a linear map of a lentiviral vector expressing a KIF11 shRNA targeting sequence and a KIF11 coding sequence.

DETAILED DESCRIPTION

Overview of the Disclosure

Figure 1:
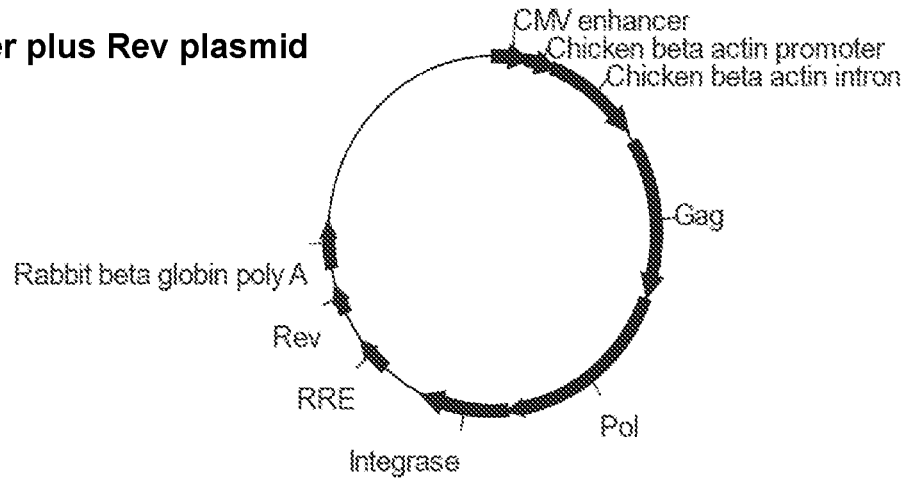
FIG. 1 depicts an exemplary 3-vector lentiviral vector system, in a circularized form.
Figure 1:
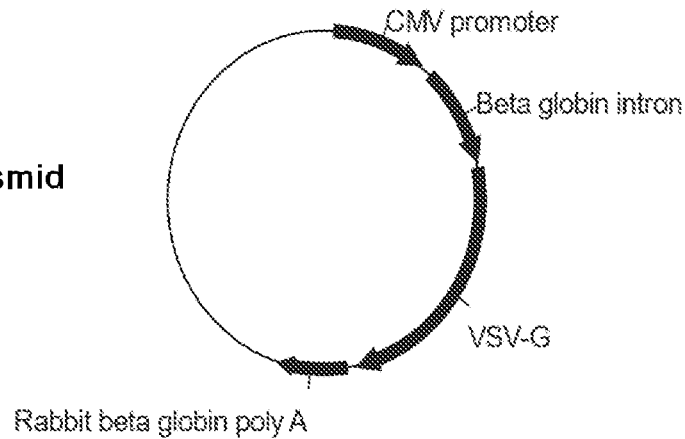
Figure 1:
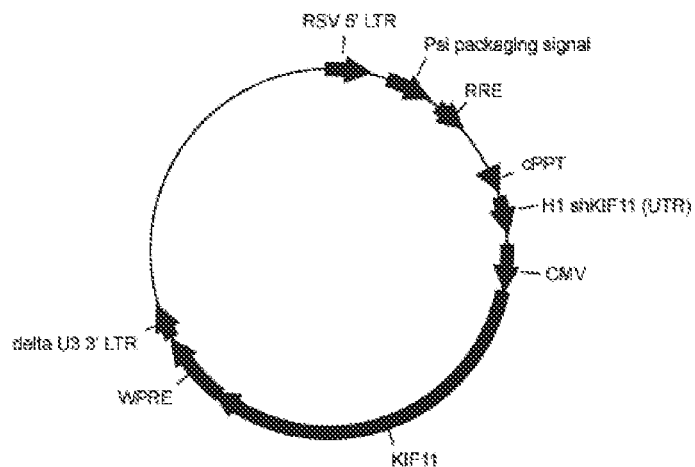

In an aspect, this disclosure relates to vectors and modified cells that encode or express a small RNA capable of binding to a host cell copy of KIF11. In embodiments, the vectors are viral vectors. In embodiments, the modified cells are modified mesenchymal stem cells.

In another aspect, this disclosure relates to vectors and modified cells that encode or express: (i) a small RNA capable of binding a host copy of KIF11; and (ii) a modified KIF11 that is resistant to the small RNA. In embodiments, the vectors are viral vectors. In embodiments, the modified cells are mesenchymal stem cells.

In another aspect, this disclosure relates to vectors and modified cells that encode or express: (i) a small RNA capable of binding a host copy of KIF11; and (ii) an exogenous KIF11 gene that is resistant to the small RNA. In embodiments, the vectors are viral vectors. In embodiments, the modified cells are mesenchymal cells. In embodiments, the small RNA is capable of binding a non-coding region of a host copy of KIF11, for example, in the 5' UTR or in the 3' UTR. In embodiments, the exogenous KIF11 gene lacks at least a portion of a target sequence (e.g., a sequence portion thereof). In such embodiments, the exogenous KIF11 is resistant to activity by the small RNA, for example, to the ability of the small RNA to bind the exogenous KIF11. In such embodiments, the ability of the small RNA to modulate expression of the exogenous KIF11 is decreased and/or prevented.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The terms "administration of" or "administering" an active agent should be understood to mean providing an active agent to the subject in need of treatment in a form that can be introduced into that individual's body in a therapeutically useful form and therapeutically effective amount.

As used herein, the term "allogeneic" refers to a treatment in which the donor cells or tissues used in the treatment are not derived from the subject that is being treated with the donor cells or tissues. Accordingly, a treatment that is "allogeneic to the subject" refers to a treatment in which the donor cells or tissues do not derive from the subject.

As used herein, the term "autologous" refers to a treatment in which the donor cells or tissues used in the treatment are derived from the subject that is being treated with the donor cells or tissues. Accordingly, a treatment that is "autologous to the subject," refers to a treatment in which the donor cells or tissues derive from the subject.

As used herein, the term "complementary" refers to the capacity of two (2) nucleotide sequences to hybridize to each other through hydrogen bonding of one or more purines with one or more pyrimidines between the two (2) nucleotide sequences. Adenine (a purine) has the capacity of hydrogen bonding to both thymine (a pyrimidine) and uracil (a pyrimidine). Guanine (a purine) has the capacity of hydrogen bonding to cytosine (a pyrimidine). The term "complementary" includes two nucleotide sequences that are perfectly "complementary" in which each nucleobase on one nucleotide sequence is hydrogen bonded to its counterpart nucleobase on the other nucleotide sequence. The term "complementary" includes two nucleotide sequences that are imperfectly "complementary" in which at least one nucleobase on one nucleotide sequence is not hydrogen bonded to its counterpart nucleobase on the other nucleotide sequence. Imperfect "complementary" occurs when a nucleobase on one of the nucleotide sequences does not have the capacity to hydrogen bond to its counterpart nucleobase on the other nucleotide sequence. For example, when the counterpart to adenine on one of the nucleotide sequences is guanine or, for example, when the counterpart to uracil on one of the nucleotide sequences is cytosine. Two nucleotide sequences that are "complementary" may include a nucleotide sequence of a small RNA that is "complementary" to a nucleotide sequence of a mRNA. The nucleotide sequence of the small RNA may be perfectly "complementary" or imperfectly "complementary" to the nucleotide sequence of the mRNA.

As used herein, the term "comprising" is intended to mean that the compositions and methods include the recited elements, but does not exclude other elements. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "expression," "expressed," or "encodes" refers to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The terms "individual," "subject," and "patient" are used interchangeably herein, and refer to any individual mammal subject, e.g., murine, porcine, bovine, canine, feline, equine, non-human primate or human primate.

The term "KIF11" refers to the gene Kinesin family member 11, also known as Kinesin-5. KIF11 functions in mitosis through interacting with the mitotic spindle. The term KIF11 includes all wild-type and variant KIF11 sequences, including both nucleotide and peptide sequences. Without limitation, the term KIF11 includes reference to SEQ ID NO: 4, and further includes variants having at least about 80% identity therewith.

The term "miRNA" refers to a microRNA, and also may be referred to herein as "miR".

The term "non-coding sequence" or "non-coding region" refers to the portion of a gene that does not code for a protein. The term without limitation refers to 5' untranslated sequences or regions of the gene, 3' untranslated sequences or regions of the gene, and introns of the gene.

The term "packaging cell line" refers to any cell line that can be used to express a lentiviral particle.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, word-length=3 to obtain amino acid sequences homologous to the protein molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

As used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "SEQ ID NO" is synonymous with the term "Sequence ID No."

As used herein, "small RNA" refers to non-coding RNA that are generally less than about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, generally through pathways that result in the destruction of the target gene mRNA.

As used herein, a "target cell" is any cell that contains a surface molecule, such as a cell surface receptor, to which a biochemical agent, such as a vector or plasmid, is capable of binding. Upon interaction between the surface molecule and the biochemical agent, the "target cell" is capable of uptake of the biochemical agent by means of, for example, transduction. Uptake of the biochemical agent may result in modification to the genotype, the phenotype, or both the genotype and the phenotype of the "target cell."

As used herein, the term "target sequence" refers to a sequence portion on a gene or variant thereof that is complementary to a nucleic acid such as a small RNA. A "target sequence" may include a sequence portion on a coding region of a gene. Alternatively, a "target sequence" may include a sequence portion on a non-coding region of a gene such as a 3' UTR or a 5' UTR. For example, a "target sequence" may include a sequence portion on the 3' UTR or the 5' UTR of the KIF11 gene.

The term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" includes, without limitation, any suitable viral vector, including an integrating vector or a non-integrating vector. In certain embodiments, a lentiviral vector or an AAV vector is used. In certain embodiments, a retrovirus, a measles virus, a mumps virus, an arenavirus, a picornavirus, a herpesvirus, or a poxvirus is used. Additionally, as used herein with reference to the lentiviral vector system, the term "vector" is synonymous with "plasmid". For example, the 3-vector and 4-vector systems, which include the 2-vector and 3-vector packaging systems, can also be referred to as 3-plasmid and 4-plasmid systems.

"A treatment" is intended to target the disease state and combat it, i.e., ameliorate or prevent the disease state. The particular treatment thus will depend on the disease state to be targeted and the current or future state of medicinal therapies and therapeutic approaches. A treatment may have associated toxicities.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

As used herein, the term "UTR" or "untranslated region" is in reference to a region of a gene that is 5' or 3' of the coding region of a gene.

As used herein, the term "3' UTR" or "3' untranslated region" is the "UTR" or "untranslated region" that is 3' of the coding region of a gene.

As used herein, the term "5' UTR" or "5' untranslated region" is the "UTR" or "untranslated region" that is 5' of the coding region of a gene.

As used herein, the term "variant" may also be referred to herein as analog or variation. A variant refers to any substitution, deletion, or addition to a nucleotide sequence.
Description of Aspects and Embodiments of the Disclosure In an aspect, a viral vector is provided comprising a first nucleotide sequence encoding a small RNA capable of binding a non-coding region of a host copy of KIF11.

In an aspect, viral vector particles described herein are derived from viruses. In embodiments, the virus is any of a measles virus, a picornavirus, a mumps virus, an arenavirus or any other virus described herein. In embodiments, the virus encodes small RNA comprising any one or more of a miRNA, a siRNA, a dsRNA, a shRNA, a ribozyme, and a piRNA.

In an aspect, viral vector particles described herein are derived from retroviruses. In embodiments, the retrovirus is a HIV virus. In embodiments, the retrovirus is any retrovirus described herein. In embodiments, the retrovirus encodes small RNA comprising any one or more of a miRNA, a siRNA, a shRNA, a ribozyme, and a piRNA.

In embodiments, the non-coding region is a 3' untranslated region or a 5' untranslated region of the host copy of KIF11. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the viral vector further comprises a second nucleotide sequence encoding a KIF11 gene or a variant thereof, wherein the KIF11 gene or the variant thereof lacks at least one sequence portion. In embodiments, the sequence portion is in a non-coding region of the KIF11 gene. In embodiments, the non-coding region of the KIF11 gene is in at least one of a 5' untranslated region or a 3' untranslated region.

In embodiments, the small RNA is a shRNA. In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the small RNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2 or SEQ ID NO: 3.

In embodiments, the KIF11 gene or variant thereof lacks more than one defined target sequence, for example, the KIF11 gene or variant thereof lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene or variant thereof lacks more than 10 defined target sequences.

In another aspect, a lentiviral particle produced by a packaging cell and capable of infecting a target cell is provided, the lentiviral particle comprising: an envelope protein capable of infecting the target cell; and a first nucleotide sequence encoding a small RNA capable of binding a non-coding region of a host copy of KIF11.

In embodiments, the lentiviral particle further comprises a Gag protein. In embodiments, the lentiviral particle further comprises a Pol protein.

In embodiments, the non-coding region is a 3' untranslated region or a 5' untranslated region. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the lentiviral particle further comprises a second nucleotide sequence encoding a KIF11 gene or a variant thereof, wherein the KIF11 gene or the variant thereof lacks at least one sequence portion. In embodiments, the sequence portion is in a non-coding region of the KIF11 gene. In embodiments, the non-coding region of the KIF11 gene is in at least one of the 5' untranslated region or the 3' untranslated region. In embodiments, the target cell is a mesenchymal stem cell.

In embodiments, the small RNA is a shRNA. In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the small RNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2 or

SEQ ID NO: 3.

In embodiments, the KIF11 gene or variant thereof lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene or variant thereof lacks more than 10 defined target sequences.

In another aspect, a modified mesenchymal stem cell is provided comprising a mesenchymal stem cell infected with a lentiviral particle, wherein the lentiviral particle comprises: an envelope protein capable of infecting the mesenchymal stem cell; and a first nucleotide sequence encoding a small RNA capable of binding a non-coding region of a host copy of KIF11.

In embodiments, the lentiviral particle further comprises a Gag protein. In embodiments, the lentiviral particle further comprises a Pol protein.

In embodiments, the non-coding region is a 3' untranslated region or a 5' untranslated region. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the first nucleotide sequence is present in the modified mesenchymal stem cell at between about 1 and about 10 copies per cell.

In embodiments, the nucleotide sequence encoding the small RNA is present at 1 copy per cell, 2 copies per cell, 3 copies per cell, 4 copies per cell, 5 copies per cell, 6 copies per cell, 7 copies per cell, 8 copies per cell, 9 copies per cell, or 10 copies per cell. In embodiments, the nucleotide sequence encoding the small RNA is present between about 10 and about 20 copies per cell.

In embodiments, the small RNA is a shRNA. In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the small RNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2 or SEQ ID NO: 3.

In another aspect, a method of producing a modified mesenchymal stem cell is provided, the method comprising: infecting a mesenchymal stem cell with an effective amount of a lentiviral particle, wherein the lentiviral particle comprises: an envelope protein capable of infecting the mesenchymal stem cell; and a first nucleotide sequence encoding a small RNA capable of binding at least one complementary region in a non-coding region of a host copy of KIF11.

In embodiments, the lentiviral particle further comprises a Gag protein. In embodiments, the lentiviral particle further comprises a Pol protein.

In embodiments, the non-coding region is a 3' untranslated region or a 5' untranslated region. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the first nucleotide sequence is present in the modified mesenchymal stem cell at between about 1 and about 10 copies per cell.

In embodiments, the nucleotide sequence encoding the small RNA is present at 1 copy per cell, 2 copies per cell, 3 copies per cell, 4 copies per cell, 5 copies per cell, 6 copies per cell, 7 copies per cell, 8 copies per cell, 9 copies per cell, or 10 copies per cell. In embodiments, the nucleotide sequence encoding the small RNA is present between about 10 and about 20 copies per cell.

In embodiments, the small RNA is a shRNA. In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the small RNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2 or SEQ ID NO: 3.

In embodiments, the KIF11 gene or variant thereof lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene or variant thereof lacks more than 10 defined target sequence.

In another aspect, a method of treating cancer in a subject is provided, the method comprising administering a therapeutically-effective amount of any modified mesenchymal stem cell described herein to the subject.

In embodiments, the modified mesenchymal stem cell is allogeneic to the subject. In embodiments, the modified mesenchymal stem cell is autologous to the subject.

In embodiments, the cancer is selected from any one or more of a carcinoma, a sarcoma, a myeloma, a lymphoma, a mixed type, or a mixture of the foregoing. In embodiments, the cancer is any cancer described herein.

In another aspect, a use of the modified mesenchymal stem cell to treat cancer is provided comprising any of the modified mesenchymal stem cells described herein.

In another aspect, a method of treating cancer in a subject is provided, the method comprising administering a therapeutically effective amount of any lentiviral particle described herein to the subject.

In embodiments, the cancer is selected from any one or more of a carcinoma, a sarcoma, a myeloma, a lymphoma, a mixed type, or a mixture of the foregoing.

In embodiments, the lentiviral particle is administered to the subject via an infected target cell. In embodiments, the target cell comprises a somatic cell. In embodiments the somatic cell comprises a bone cell, a cartilage cell, a nerve cell, an epithelial cell, a muscle cell, a blood cell, a conductive cell, a connective cell, a glandular cell, or a supportive cell.

In embodiments, the somatic cell comprises a hepatocyte.

In embodiments, the somatic cell comprises a lymphocyte. In embodiments, the lymphocyte comprises a B cell. In embodiments, the lymphocyte comprises a T cell. In embodiments, the T cell comprises a tumor specific T cell.

In embodiments, the target cell comprises a stem cell. In embodiments, the stem cell comprises an embryonic stem cell. In embodiments, the stem cell comprises a somatic stem cell. In embodiments, the stem cell comprises an induced pluripotent stem cell. In embodiments, the stem cell comprises a mesenchymal stem cell.

In another aspect, a viral vector is provided, the viral vector comprises: (i) an encoded KIF11 gene comprising a coding region, and at least one of a 5' untranslated region and a 3' untranslated region, wherein the KIF11 gene lacks at least one defined target sequence in at least one of the 5' untranslated region or the 3' untranslated region, and (ii) a small RNA capable of binding at least one complementary region in a non-coding region of a host copy of KIF11, wherein expression of the encoded KIF11 gene is resistant to activity by the small RNA.

In embodiments, the KIF11 gene lacks at least one defined target sequence in the 5' untranslated region. In embodiments, the KIF11 gene lacks at least one defined target sequence in the 3' untranslated region. In embodiments, the KIF11 gene lacks at least one defined target sequence in both the 5' and 3' untranslated regions.

In embodiments, the KIF11 gene lacks more than one defined target sequences, for example, the KIF11 gene lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene lacks more than 10 defined target sequences.

In embodiments, the KIF11 gene comprises a variant in a portion of its non-coding region relative to a host copy of KIF11. In embodiments, the variant comprises a substitution in the nucleotide sequence of KIF11. In embodiments, the variant comprises a deletion in the nucleotide sequence of KIF11. In embodiments, the variant comprises an addition to the nucleotide sequence of KIF11. In embodiments, the variant is in the 3' untranslated region of the KIF11 gene. In embodiments, the variant is in the 5' untranslated region of the KIF11 gene. In embodiments, the variant causes the KIF11 gene to lack at least one target sequence (e.g., a sequence portion thereof).

In embodiments, the KIF11 gene or variant thereof comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with SEQ ID NO: 4.

In embodiments, the small RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, and SEQ ID NO: 3.

In embodiments, the small RNA targets a sequence not present in the gene expression construct of the same lentivirus vector to avoid the possibility of intragenic recombination of the vector or plasmids encoding vector components. In embodiments, the small RNA targets a sequence not present in the gene expression construct of the same lentivirus vector, when the protein coding region differs by a small number of mutations.

In embodiments, a small number of mutations is less than 20 mutations. In embodiments, a small number of mutations is less than 15 mutations. In embodiments, a small number of mutations is less than 10 mutations. In embodiments, a small number of mutations is less than 5 mutations. In embodiments, a small number of mutations is 4 mutations. In embodiments, a small number of mutations is 3 mutations. In embodiments, a small number of mutations is 2 mutations. In embodiments, a small number of mutations is 1 mutation.

In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the viral vector is a lentiviral vector. In embodiments, the viral vector is an AAV vector.

In another aspect, a lentiviral particle produced by a packaging cell is provided. In embodiments the lentiviral particle is produced in the 293T/17 HEK packaging cell line. In embodiments, the lentiviral particle is produced in any cell known in the art that is capable of producing a lentiviral particle.

In embodiments, the lentiviral particle comprises an envelope protein capable of infecting target cells. In embodiments, the lentiviral particle comprises (i) a KIF11 gene comprising a coding region, and at least one of a 5' untranslated region and a 3' untranslated region, wherein the KIF11 gene sequence lacks at least one defined target sequence in at least one of the 5' untranslated region or the 3' untranslated region; and (ii) a small RNA capable of binding to at least one complementary region in a non-coding region of a host copy of KIF11, wherein the KIF11 gene in the lentiviral particle is resistant to activity by the small RNA.

In embodiments, the KIF11 gene in the lentiviral particle lacks at least one defined target sequence in the 5' untranslated region. In embodiments, the KIF11 gene in the lentiviral particle lacks at least one defined target sequence in the 3' untranslated region. In embodiments, the KIF11 gene in the lentiviral particle lacks at least one defined target sequence in both the 5' and 3' untranslated regions.

In embodiments, the KIF11 gene in the lentiviral particle lacks more than one defined target sequence, for example, the KIF11 gene in the lentiviral particle lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene in the lentiviral particle lacks more than 10 defined target sequences.

In embodiments, the KIF11 gene in the lentiviral particle comprises a variant in a portion of its non-coding sequence relative to a host copy of the KIF11 gene. In embodiments, the variant comprises a substitution in the non-coding sequence of KIF11. In embodiments, the variant comprises a deletion in the non-coding sequence of KIF11. In embodiments, the variant comprises an addition to the non-coding sequence of KIF11. In embodiments, the variant is in the 3' untranslated region of the KIF11 gene in the lentiviral particle. In embodiments, the variant is in the 5' untranslated region of the KIF11 gene in the lentiviral particle. In embodiments, the variant causes the KIF11 gene to lack at least one target sequence (e.g., a sequence portion thereof).

In embodiments, the KIF11 gene in the lentiviral particle or variant thereof comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with SEQ ID NO: 4.

In embodiments, the small RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, or SEQ ID NO: 3.

In embodiments, the small RNA is a siRNA. In embodiments, the small RNA is a microRNA. In embodiments, the small RNA is a dsRNA. In embodiments, the small RNA is a piRNA. In embodiments, the small RNA is a ribozyme.

In another aspect, a method of treating a cancer in a subject using an immunotherapy-based composition is provided. In embodiments, the method comprises administering or having administered a therapeutically-effective amount of the immunotherapy-based composition to the subject.

In embodiments, the immunotherapy-based composition comprises a modified cell. In embodiments, the modified cell is a modified mesenchymal stem cell.

In embodiments, the immunotherapy-based composition further comprises a lentiviral particle, that comprises: (i) an envelope protein capable of infecting a cancer cell; (ii) a KIF11 gene comprising a coding region, and at least one of a 5' untranslated region and a 3' untranslated region, wherein the KIF11 gene lacks at least one defined target sequence in at least one of the 5' untranslated region and the 3' untranslated region; and (iii) a small RNA capable of binding at least one complementary region in a non-coding region of a host copy of a KIF11 gene, wherein the KIF11 gene in the lentiviral particle is resistant to activity by the small RNA.

In embodiments, the KIF11 gene in the lentiviral particle lacks at least one defined target sequence in the 5' untranslated region. In embodiments, the KIF11 gene in the lentiviral particle lacks at least one defined target sequence in the 3' untranslated region. In embodiments, the KIF11 gene in the lentiviral particle lacks at least one defined target sequence in both the 5' and 3' untranslated regions.

In embodiments, the KIF11 gene in the lentiviral particle lacks more than one defined target sequence, for example, the KIF11 gene in the lentiviral particle lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene in the lentiviral particle lacks more than 10 defined target sequences.

In embodiments, the KIF11 gene in the lentiviral particle comprises a variant in a portion of its non-coding sequence relative to a host copy of KIF11. In embodiments, the variant comprises a substitution in the nucleotide sequence of KIF11. In embodiments, the variant comprises a deletion in the nucleotide sequence of KIF11. In embodiments, the variant comprises an addition to the nucleotide sequence of KIF11. In embodiments, the variant is in the 3' untranslated region of the first nucleotide sequence. In embodiments, the variant is in the 5' untranslated region of the first nucleotide sequence. In embodiments, the variant causes the KIF11 gene to lack at least one target sequence (e.g., a sequence portion thereof).

In embodiments, the KIF11 gene in the lentiviral particle comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with SEQ ID NO: 4.

In embodiments, the small RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, and SEQ ID NO: 3.

In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In another aspect, a modified cell is provided comprising a coding region of a KIF11 gene, wherein the KIF11 gene lacks at least one defined target sequence in at least one of a 5' untranslated region or a 3' untranslated region. In embodiments, the modified cell expresses a small RNA capable of binding to at least one complementary region in a non-coding region of a host copy of the KIF11 gene.

In embodiments, the modified cell is a modified cell of any cell known in the art. In embodiments, the modified cell is a modified bone cell. In embodiments, the modified cell is a modified cartilage cell. In embodiments, the modified cell is a modified nerve cell. In embodiments, the modified cell is a modified epithelial cell. In embodiments, the modified cell is a modified muscle cell. In embodiments, the modified cell is a modified blood cell. In embodiments, the modified cell is a modified conductive cell. In embodiments, the modified cell is a modified connective cell. In embodiments, the modified cell is a modified glandular cell. In embodiments, the modified cell is a modified supportive cell.

In embodiments, the modified cell is a modified mesenchymal stem cell.

In embodiments, the modified cell is cultured such that it expands and/or proliferates to create a seed stock of cells that can be used in therapy.

In embodiments, the modified cell or seed stock is used to treat a cancer. In embodiments, the modified cell or seed stock is used to treat any of the cancers described herein.

In embodiments, the modified cell or seed stock is used to treat a tumor. In embodiments, the tumor is a solid tumor. In embodiments, the tumor is a benign tumor. In embodiments, the tumor is a metastatic tumor. In embodiments, the tumor is a fluid-filled tumor.

In embodiments, the modified cell or seed stock is used to treat a cell or group of cells that is different from the modified cell or seed stock.

In embodiments, the modified cell or seed stock is used in a cell therapy. In embodiments, the cell therapy is an allogeneic cell therapy. In embodiments, the cell therapy is an autologous cell therapy.

In embodiments, the KIF11 gene exogenously expressed in the modified cell lacks at least one defined target sequence in a 5' untranslated region. In embodiments, the KIF11 gene exogenously expressed in the modified cell lacks at least one defined target sequence in a 3' untranslated region. In embodiments, the KIF11 gene exogenously expressed in the modified cell lacks at least one defined target sequence in both the 5' and 3' untranslated regions.

In embodiments, the KIF11 gene exogenously expressed in the modified cell lacks more than one defined target sequence in its untranslated region(s), for example, lacks 2 defined target sequences, lacks 3 defined target sequences, lack 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene exogenously expressed in the modified cell lacks more than 10 defined target sequences.

In embodiments, the KIF11 gene exogenously expressed in the modified cell comprises a variant in a portion of its non-coding sequence relative to a host copy of the KIF11 gene. In embodiments, the variant comprises a substitution in the nucleotide sequence of KIF11. In embodiments, the variant comprises a deletion in the nucleotide sequence of KIF11. In embodiments, the variant comprises an addition to the nucleotide sequence of KIF11. In embodiments, the variant is in a 3' untranslated region of the KIF11 gene exogenously expressed in the modified cell. In embodiments, the variant is in a 5' untranslated region of the KIF11 gene exogenously expressed in the modified cell. In embodiments, the variant causes the KIF11 gene to lack at least one target sequence (e.g., a sequence portion thereof).

In embodiments, KIF11 gene exogenously expressed in the modified cell comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity with SEQ ID NO: 4.

In embodiments, the regulatory RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, and SEQ ID NO: 3.

In embodiments, the small RNA is a siRNA. In embodiments, the small RNA is a microRNA. In embodiments, the small RNA is a dsRNA. In embodiments, the small RNA is a piRNA. In embodiments, the small RNA is a ribozyme.

In embodiments, the small RNA inhibits expression of a host copy of the KIF11 gene through binding the 3' untranslated region of the gene.

In embodiments, the small RNA is delivered to cancer cells as part of a cell therapy. In embodiments, the cell therapy is an autologous cell therapy. In embodiments, the cell therapy is an allogeneic cell therapy.

In embodiments, the cancer cells are any type of cancer cells known in the art. In embodiments, the cancer cells are derived from any cancer described herein.

In embodiments, the small RNA results in reduction in KIF11 mRNA expression relative to control treatments. In embodiments, the reduction in KIF11 mRNA expression is 1% or greater relative to control treatments, for example, greater than 5%, greater than 10%, greater than 15%, greater than 20%, greater than 20%, greater than 25%, greater than 30%, greater than 35%, greater than 40%, greater than 45%, greater than 50%, greater than 55%, greater than 60%, greater than 70%, greater than 75%, greater than 80%, greater than 85%, greater than 90%, or greater than 95%.

In embodiments, reduction in KIF11 mRNA expression results in reduction of cell number relative to control treatments. In embodiments, the cell number is reduced by more than 1%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, or more than 95%.

In another aspect, a lentiviral vector is provided that co-expresses (i) a small RNA and (ii) a KIF11 gene. In embodiments, the small RNA targets a host copy of the KIF11 gene and the KIF11 gene expressed by the lentiviral vector is resistant to the small RNA. In embodiments, the KIF11 gene expressed by the lentiviral vector is truncated. In embodiments, the truncation is at the 3' untranslated region. In embodiments, the truncation is at the 5' untranslated region. In embodiments the KIF11 gene expressed by the lentiviral vector is mutated. In embodiments, the mutation is in the 3' untranslated region. In embodiments, the mutation is in the 5' untranslated region.

In embodiments, the small RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, and SEQ ID NO: 3.

In embodiments, the lentiviral vector is delivered to cancer cells as part of cell therapy. In embodiments, the cancer cells are any cancer cells known in the art. In embodiments, the cell therapy is an allogeneic cell therapy. In embodiments, the cell therapy is an autologous cell therapy.

In embodiments, the KIF11 gene has at least one variant in its 3' untranslated region relative to a host copy of the KIF11 gene. In embodiments, the variant comprises a substitution in the nucleotide sequence of the KIF11 gene. In embodiments, the variant comprises a deletion in the nucleotide sequence of the KIF11 gene. In embodiments, the variant comprises an addition to the nucleotide sequence of the KIF11 gene.

In embodiments, the vector system that carries the genetic material is a 2-component vector system. In embodiments, the vector system that carries the genetic material is a 3-component vector system.

In another aspect, modified mesenchymal stem cells are provided. In embodiments, the modified mesenchymal stem cells produce inhibitory RNA against KIF11. In embodiments, the modified mesenchymal stem cells retain their growth capacity through exogenous expression of KIF11. In embodiments, the KIF11 that is exogenously expressed lacks a non-coding sequence that can be targeted by the small RNA.

In embodiments, the mesenchymal stems are genetically modified using a 2-component lentivirus vector system. In embodiments, the 2-component lentivirus vector system delivers inhibitory RNA that targets KIF11. In embodiments, the 2-component lentivirus vector system delivers an exogenous KIF11 gene.

In embodiments, the modified mesenchymal cells have special properties that allow engaging in cell-to-cell contact with tumor cells. In embodiments, the cell-to-cell contact allows for delivery of small RNA that target KIF11 to cancer cells via a portal formed by connexin proteins.

Cancer

The compositions and methods provided herein are used to treat cancer. A cell, tissue, or target may be a cancer cell, a cancerous tissue, harbor cancerous tissue, or be a subject or patient diagnosed or at risk of developing a disease or condition. In certain aspects, a cell may be an epithelial, an endothelial, a mesothelial, a glial, a stromal, or a mucosal cell. The cancer cell population can include, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell, can also include a cancer cell population from any of the foregoing, and can be associated with one or more of carcinomas, sarcomas, myelomas, lymphomas, mixed types or mixtures of the foregoing. In still a further aspect cancer includes, but is not limited to astrocytoma, acute myeloid anaplastic large cell lymphoma, angiosarcoma, B-cell lymphoma, Burkitt's lymphoma, breast carcinoma, bladder carcinoma, carcinoma of the head and neck, cervical carcinoma, colorectal carcinoma, endometrial carcinoma, esophageal squamous cell carcinoma, Ewing's sarcoma, fibrosarcoma, glioma, glioblastoma, gastrinoma, gastric carcinoma, hepatoblastoma, hepatocellular carcinoma, Kaposi's sarcoma, Hodgkin lymphoma, laryngeal squamous cell carcinoma, larynx carcinoma, leiomyosarcoma, lipoma, liposarcoma, melanoma, mantle cell lymphoma, medulloblastoma, mesothelioma, myxofibrosarcoma, mucosa-associated lymphoid tissue B cell lymphoma, multiple myeloma, high-risk myelodysplastic syndrome, nasopharyngeal carcinoma, neuroblastoma, neurofibroma, high-grade non-Hodgkin lymphoma, non-Hodgkin lymphoma, lung carcinoma, non-small cell lung carcinoma, ovarian carcinoma, oesophageal carcinoma, osteosarcoma, pancreatic carcinoma, pheochromocytoma, prostate carcinoma, renal cell carcinoma, retinoblastoma, rhabdomyosarcoma, salivary gland tumor, Schwannoma, small cell lung cancer, squamous cell carcinoma of the head and neck, testicular tumor, thyroid carcinoma, urothelial carcinoma, and Wilm's tumor.

The compositions and methods provided herein are also used to treat NSCLC (non-small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases.

Genetic Medicines

Genetic medicine includes reference to viral vectors that are used to deliver genetic constructs to host cells for the purposes of disease therapy or prevention. Genetic medicines include cell therapies in which cells have been modified through delivery of the genetic constructs to the cells.

Genetic constructs can include, but are not limited to, functional genes or portions of genes to correct or complement existing defects, DNA sequences encoding regulatory proteins, DNA sequences encoding regulatory RNA molecules including antisense, short homology RNA, long noncoding RNA, small interfering RNA or others, and decoy sequences encoding either RNA or proteins designed to compete for critical cellular factors to alter a disease state. Genetic constructs include constructs that encode or express regulatory sequences that are capable of knocking down gene expression. Genetic medicine involves delivering these therapeutic genetic constructs either directly or through cell therapies to target cells to provide treatment or alleviation of a particular disease.

Therapeutic Vectors

A lentiviral virion (particle) in accordance with various aspects and embodiments herein is expressed by a vector system encoding the necessary viral proteins to produce a virion (viral particle). In various embodiments, one vector containing a nucleic acid sequence encoding the lentiviral Pol proteins is provided for reverse transcription and integration, operably linked to a promoter. In another embodiment, the pol proteins are expressed by multiple vectors. In other embodiments, vectors containing a nucleic acid sequence encoding the lentiviral Gag proteins for forming a viral capsid, operably linked to a promoter, are provided. In embodiments, this gag nucleic acid sequence is on a separate vector than at least some of the pol nucleic acid sequence. In other embodiments, the gag nucleic acid is on a separate vector from all the pol nucleic acid sequences that encode pol proteins.

Numerous modifications can be made to the vectors herein, which are used to create the particles to further minimize the chance of obtaining wild type revertants. These include, but are not limited to, deletions of the U3 region of the LTR, tat deletions and matrix (MA) deletions. In embodiments, the gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment, the envelope protein is not from a lentivirus, but from a different virus. In such instances, the resultant particle is referred to as a pseudotyped particle. By appropriate selection of envelopes one can "infect" virtually any cell. For example, one can use an env gene that encodes an envelope protein that targets an endocytic compartment. Examples of viruses from which such env genes and envelope proteins can be derived from include the influenza virus (e.g., the Influenza A virus, Influenza B virus, Influenza C virus, Influenza D virus, Isavirus, Quaranjavirus, and Thogotovirus), the Vesiculovirus (e.g., Indiana vesiculovirus), alpha viruses (e.g., the Semliki forest virus, Sindbis virus, Aura virus, Barmah Forest virus, Bebaru virus, Cabassou virus, Getah virus, Highlands J virus, Trocara virus, Una Virus, Ndumu virus, and Middleburg virus, among others), arenaviruses (e.g., the lymphocytic choriomeningitis virus, Machupo virus, Junin virus and Lassa Fever virus), flaviviruses (e.g., the tick-borne encephalitis virus, Dengue virus, hepatitis C virus, GB virus, Apoi virus, Bagaza virus, Edge Hill virus, Jugra virus, Kadam virus, Dakar bat virus, Modoc virus, Powassan virus, Usutu virus, and Sal Viej a virus, among others), rhabdoviruses (e.g., vesicular stomatitis virus, rabies virus), paramyxoviruses (e.g., mumps or measles) and orthomyxoviruses (e.g., influenza virus).

Other envelope proteins that can preferably be used include those derived from endogenous retroviruses (e.g., feline endogenous retroviruses and baboon endogenous retroviruses) and closely related gammaretroviruses (e.g., the Moloney Leukemia Virus, MLV-E, MLV-A, Gibbon Ape Leukemia Virus, GALV, Feline leukemia virus, Koala retrovirus, Trager duck spleen necrosis virus, Viper retrovirus, Chick syncytial virus, Gardner-Arnstein feline sarcoma virus, and Porcine type-C oncovirus, among others). These gammaretroviruses can be used as sources of env genes and envelope proteins for targeting primary cells. The gammaretroviruses are particularly preferred where the host cell is a primary cell.

Envelope proteins can be selected to target a specific desired host cell. For example, targeting specific receptors such as a dopamine receptor can be used for brain delivery. Another target can be vascular endothelium. These cells can be targeted using an envelope protein derived from any virus in the Filoviridae family (e.g., Cuevaviruses, Dianloviruses, Ebolaviruses, and Marburgviruses). Species of Ebolaviruses include Tai Forest ebolavirus, Zaire ebolavirus, Sudan ebolavirus, Bundibugyo ebolavirus, and Reston ebolavirus.

In addition, in embodiments, glycoproteins can undergo post-transcriptional modifications. For example, in an embodiment, the GP of Ebola, can be modified after translation to become the GP1 and GP2 glycoproteins. In another embodiment, one can use different lentiviral capsids with a pseudotyped envelope (e.g., FIV or SHIV [U.S. Pat. No. 5,654,195]). A SHIV pseudotyped vector can readily be used in animal models such as monkeys.

Lentiviral vector systems as provided herein typically include at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 1). In another embodiment, the gag and pol genes are provided on a first plasmid and the rev gene is provided on a second plasmid (e.g., FIG. 2). Accordingly, both 3-vector and 4-vector systems can be used to produce a lentivirus as described herein. In embodiments, the therapeutic vector, at least one envelope plasmid and at least one helper plasmid are transfected into a packaging cell, for example a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of KIF11 and/or inhibiting the expression of endogenous KIF11.

Figure 2:
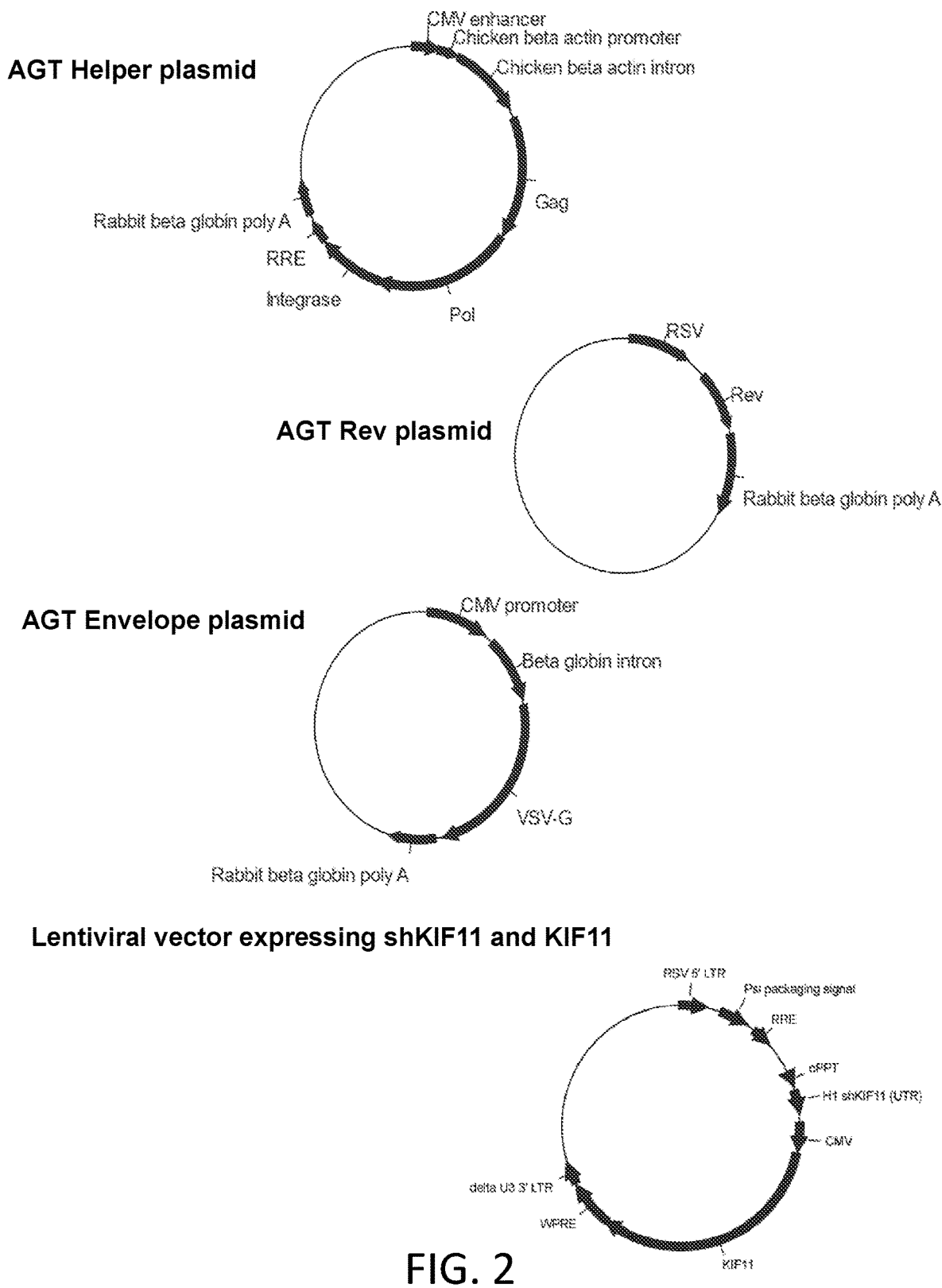
FIG. 2 depicts an exemplary 4-vector lentiviral vector system, in a circularized form.

In another aspect, and as detailed in FIG. 1 and FIG. 2, the lentiviral vector, which is also referred to herein as a therapeutic vector, can include the following elements: hybrid 5' long terminal repeat (RSV/5' LTR) (SEQ ID NO: 5 and SEQ ID NO: 6), Psi sequence (RNA packaging site) (SEQ ID NO: 7), RRE (Rev-response element) (SEQ ID NO: 8), cPPT (polypurine tract) (SEQ ID NO: 9), H1 promoter (SEQ ID NO: 10), KIF11 shRNA (SEQ ID NO: 1, SEQ ID NO: 2, or SEQ ID NO: 3), Woodchuck Post-Transcriptional Regulatory Element (WPRE) (SEQ ID NO: 11), and 3' Delta LTR (SEQ ID NO: 12). In another aspect, sequence variation, by way of substitution, deletion, addition, or mutation can be used to modify the sequences references herein.

In another aspect, the lentiviral vector, which is also referred to herein as a therapeutic vector, can include the following elements: 5' long terminal repeat, RRE (Rev-response element), cPPT (polypurine tract), H1 promoter, KIF11 shRNA, CMV promoter, transferrin receptor transmembrane region fused with IgG1 Fc, Woodchuck Post-Transcriptional Regulatory Element (WPRE), and 3' Delta LTR.

In another aspect, a helper plasmid has been designed to include the following elements: CAG promoter (SEQ ID NO: 13); HIV component gag (SEQ ID NO: 14); HIV component pol (SEQ ID NO: 15); HIV Int (SEQ ID NO: 16); HIV RRE (SEQ ID NO: 17); and HIV Rev (SEQ ID NO: 18).

In another aspect, a helper plasmid has been designed to include the following elements: CMV enhancer, chicken beta actin promoter, rabbit beta globin intron, HIV component gag; HIV component pol; HIV Int; HIV RRE; HIV Rev, and rabbit beta globin poly A.

In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from human endogenous retroviruses including HERV-W, baboon endogenous retrovirus BaEV, feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, Md.), and can also be designed as described herein. Moreover, it is within the skill of a person skilled in the art to substitute or modify aspects of a lentiviral packaging system to improve any number of relevant factors, including the production efficiency of a lentiviral particle.

In another aspect, adeno-associated viral (AAV) vectors can also be used.

AAV Vector Construction. KIF11 sequence (SEQ ID NO: 4) or KIF11 shRNA sequence (e.g., SEQ ID NO: 1, SEQ ID NO: 2, or SEQ ID NO: 3) can be inserted into the pAAV plasmid (Cell Biolabs). KIF11 oligonucleotide sequences containing BamHI and EcoRI restriction sites are synthesized by Eurofins MWG Operon. Overlapping sense and antisense oligonucleotide sequences are mixed and annealed during cooling from 70 degrees Celsius to room temperature. The pAAV are digested with the restriction enzymes BamHI and EcoRI for one hour at 37 degrees Celsius. The digested pAAV plasmid are purified by agarose gel electrophoresis and extracted from the gel using a DNA gel extraction kit from Thermo Scientific. The DNA concentrations are determined and vector to oligo (3:1 ratio) are mixed, allowed to anneal, and ligated. The ligation reaction is performed with T4 DNA ligase for 30 minutes at room temperature. 2.5 microliters of the ligation mix are added to 25 microliters of STBL3 competent bacterial cells. Transformation is achieved after heat-shock at 42 degrees Celsius. Bacterial cells are spread on agar plates containing ampicillin and drug-resistant colonies (indicating the presence of ampicillin-resistance plasmids) are recovered and expanded in LB broth. To check for insertion of the oligo sequences, plasmid DNA is extracted from harvested bacteria cultures with the Thermo Scientific DNA mini prep kit. Insertion of shRNA sequences in the pAAV plasmid is verified by DNA sequencing using a specific primer for the promoter used to regulate shRNA expression.

Production of AAV particles. The AAV-KIF11 shRNA plasmid is combined with the plasmids pAAV-RC2 (Cell Biolabs) and pHelper (Cell Biolabs). The pAAV-RC2 plasmid contains the Rep and AAV2 capsid genes and pHelper contains the adenovirus E2A, E4, and VA genes. To produce AAV particles, these plasmids are transfected in the ratio 1:1:1 (pAAV-shKIF11: pAAV-RC2: pHelper) into 293T cells. For transfection of cells in 150 mm dishes (BD Falcon), 10 micrograms of each plasmid are added together in 1 ml of DMEM. In another tube, 60 microliters of the transfection reagent PEI (1 microgram/ml) (Polysciences) is added to 1 ml of DMEM. The two tubes are mixed together and allowed to incubate for 15 minutes. Then the transfection mixture is added to cells and the cells are collected after 3 days. The cells are lysed by freeze/thaw lysis in dry ice/isopropanol. Benzonase nuclease (Sigma) is added to the cell lysate for 30 minutes at 37 degrees Celsius. Cell debris is then pelleted by centrifugation at 4 degrees Celsius for 15 minutes at 12,000 rpm. The supernatant is collected and then added to target cells.

Dosage and Dosage Forms

Mesenchymal Stem Cells

In embodiments, the vector compositions can be administered to mesenchymal stem cells (MSCs). MSCs can be isolated from multiple sources including the bone marrow, the placenta, and the umbilical cord. Subsequent to isolation, MSCs are genetically modified and expanded to create a seed stock. The seed stock can then be used in an autologous or allogeneic cell therapy. Methods of isolation of MSCs, expansion of MSCs, and administration of MSCs are described below.

Isolation and expansion of MSCs: Numerous methods are known in the art for isolating and expanding MSCs. In embodiments, MSCs are isolated from placentas, which are recovered after elective cesarean section delivery for full-term newborns. The placenta is washed in phosphate buffered saline (PBS) and the maternal decidua is removed. Tissue portions of approximately 1 cm$^3$ or 4 grams wet weight are dissected from the fetal interfacing chorionic villous. Tissue portions are washed again in PBS and treated at 37° C. with 1 mg/ml Collagenase A solution for 60 minutes. Digested material is collected by centrifugation and resuspended in a trypsin/EDTA solution for 10 minutes at 37° C. Trypsin-treated material is collected again by centrifugation, washed once, resuspended in Bio-AMF-1 medium (Biological Industries, Israel) with 1% penicillin-streptomycin solution plus 5 mM L-Glutamine. Cells were transferred to T-25 culture flasks and incubated in a humidified atmosphere at 37° C. with 5% $CO_2$. When MSC reach confluence in the T-25 flask, they are treated with trypsin/EDTA to release cells bound to plastic, diluted with medium and re-plated in new T-25 flasks.

Other methods of isolating and expanding MSCs that are known in the art can be used. Detailed protocols for isolating and expanding MSCs are described in the following references, which are incorporated herein by reference in their entirety: (i) Huang Q, Yang Y, Luo C, Wen Y, Liu R, Li S, Chen T, Sun H, and Tang L. 2019. *An efficient protocol to generate placental chorionic plate-derived mesenchymal stem cells with superior proliferative and immunomodulatory properties*. Stem Cell Research & Therapy 10:301. (ii) Hassan G, Kasem I, Antaki, R, Mohammad M B, AlKadry R, and Aljamali M. 2019. *Isolation of umbilical cord mesenchymal stem cells using blood derivatives accompanied with explant method*. Stem Cell Investigation 6:29.

Identifying phenotypes of MSCs: The MSC phenotype varies according to tissue of origin. For chorionic villous MSCs the major phenotypic markers of cell identity include: CD44, CD73, CD105, CD90, alpha-SMA, and Stro-1. Antibody staining and flow cytometry to detect these cell surface markers will confirm the presence of MSC and further indicate the fraction of cells most similar to chorionic villous MSC. Specific patterns of gene expression have also been identified for MSCs. Chorionic villous MSCs express SOX-2 but not NANOG or POU5F1. Expression of all three of these genes is a common marker for embryonic stem cell pluripotency; expression limited to SOX-2 is consistent with the partially pluripotent phenotype of MSC.

Production of lentivirus vectors: Lentivirus vectors are produced from packaging cells that were transfected with 3 (for laboratory purposes) or 4 (for clinical use) plasmids encoding virion enzyme and structural proteins, the envelope glycoprotein, and the therapeutic transgene. Typically, the envelope glycoprotein is glycoprotein G from Vesicular Stomatitis Virus. Typical lentivirus vectors complemented with VSV-G are suitable for MSC transduction and stable genetic modification.

Lentivirus vector genetic modification of MSCs: Several approaches to genetic modification of MSCs are known in the art. Lentivirus vectors are the preferred method for stable genetic modification of MSC and have been evaluated in short-term and long-term cultures of bone marrow-derived and other types of MSC. Creating lentivirus vectors expressing both marker proteins (green or red fluorescence proteins) and puromycin acetyltransferase (confers resistance to puromycin) allow for drug selection of genetically modified MSC, which appear identical to unmodified MSC after a battery of tests for phenotypic changes, altered cell mobility, or capacity for cell amplification in long-term culture.

Lentivirus vector particle transduction can be performed in three steps:

Step 1: confluent MSCs are trypsinized, diluted 1:3 and replated for 2 days.

Step 2: Lentivirus vector stock in PBS plus 8 ug/mL Polybrene is overlayed on the MSC cell monolayer for 4 hours then removed by rinsing cells with medium.

Step 3: MSCs are cultured for a defined period of time. The period of time may be less than one day, one day, or more than one day, as appropriate.

Step 4: MSCs are detached from the plate with trypsin solution and used for DNA, RNA, or protein extraction that will measure the efficiency of transduction.

For most lentivirus vectors, transduction with multiplicity of infection equal to 5 results in >80% of MSCs becoming genetically modified. The modifications are stable and transgene expression persists for many generations.

For large scale manufacturing of gene modified MSCs for clinical use, a seed stock containing 10-50 million transduced MSCs are enlarged through serial passage and adapted to suspension culture. The final cell culture volume may reach 100 to 200 L, with cell yields approaching $5 \times 10^9$ per liter. Cells are recovered by centrifugation and/or filtration, washed and resuspended in medium for in vivo administration. Large scale expansion of MSCs can be performed in suspension cultures of up to 200 L under GMP conditions.

Administration of Cell Compositions (Cell Therapy)

Genetic modification and expansion of MSCs results in the creation of seed stock that can then be used as part of a cell therapy. Subjects may be administered an allogeneic or autologous cell therapy.

The cell therapy may be administered periodically, such as once or twice a day, or any other suitable time period. For example, cell compositions may be administered to a subject in need once a week, once every other week, once every three weeks, once a month, every other month, every three months, every six months, every nine months, once a year, every eighteen months, every two years, every thirty months, or every three years.

In embodiments, the cell compositions are administered as a pharmaceutical composition. In embodiments, the pharmaceutical composition can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition can also be formulated for injection, insufflation, infusion, or intradermal exposure. For instance, an injectable formulation may comprise the cell compositions in an aqueous or non-aqueous solution at a suitable pH and tonicity.

The cell compositions may be administered to a subject via direct injection into a tumor site or at a site of infection. In embodiments, the cell compositions can be administered systemically. In embodiments, the cell compositions can be administered via guided cannulation to tissues immediately surrounding the sites of tumor or infection.

The cell compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the cell compositions can be formulated into any pharmaceutically acceptable dosage form, such as capsule, liquid dispersion, gel, aerosol, pulmonary aerosol, nasal aerosol, ointment, cream, semi-solid dosage form, a solution, an emulsion, and a suspension. Further, the pharmaceutical composition may be a transdermal delivery system.

In embodiments, the pharmaceutical composition can be formulated as a sublingual or buccal dosage form. Such dosage forms comprise solution compositions that are administered under the tongue.

In embodiments, the pharmaceutical composition can be formulated as a nasal dosage form. Such dosage forms comprise solution, suspension, and gel compositions for nasal delivery.

In embodiments, the pharmaceutical composition can be formulated in a liquid dosage form for oral administration, such as suspensions, emulsions or syrups. In embodiments, the liquid dosage form can include, in addition to commonly used simple diluents such as water and liquid paraffin, various excipients such as humectants, sweeteners, aromatics or preservatives. In embodiments, the pharmaceutical composition can be formulated to be suitable for administration to a pediatric patient.

In embodiments, the pharmaceutical composition can be formulated in a dosage form for parenteral administration, such as sterile aqueous solutions, suspensions, emulsions, non-aqueous solutions or suppositories.

The dosage of the pharmaceutical composition can vary depending on the patient's weight, age, gender, administration time and mode, excretion rate, and the severity of disease.

In embodiments, the treatment of cancer is accomplished by guided direct injection of the cell compositions into tumors, using needle, or intravascular cannulation. In embodiments, the cell compositions are administered into the cerebrospinal fluid, blood or lymphatic circulation by venous or arterial cannulation or injection, intradermal delivery, intramuscular delivery or injection into a draining organ near the site of disease.

EXAMPLES

The following examples are given to illustrate aspects of the present embodiments. It should be understood, however, that the embodiments are not to be limited to the specific conditions or details described in these examples. All printed publications referenced herein are specifically incorporated by reference.

Example 1: Development of a Lentiviral Vector System

A lentiviral vector system was developed as summarized in FIG. 1 and FIG. 2 (circularized form). Lentiviral particles can be produced in 293T/17 HEK cells (purchased from American Type Culture Collection, Manassas, Va.) following transfection with the therapeutic vector, the envelope plasmid, and the helper plasmid. The transfection of 293T/17 HEK cells, will produce functional viral particles, will use the reagent Poly(ethylenimine) (PEI) to increase the efficiency of plasmid DNA uptake. The plasmids and DNA are initially added separately in culture medium without serum in a ratio of 3:1 (mass ratio of PEI to DNA). After 2-3 days, cell medium is collected, and lentiviral particles are purified by high-speed centrifugation and/or filtration followed by anion-exchange chromatography. The concentration of lentiviral particles can be expressed in terms of transducing units/ml (TU/ml). The determination of TU is accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-plasmid system (i.e., a 2-plasmid lentiviral packaging system) was designed to produce lentiviral particles. A schematic of the 3-plasmid system is shown in FIG. 1 Briefly, and with reference to FIG. 1, the top-most vector is a helper plasmid, which, in this case, includes Rev; the vector appearing in the middle is the envelope plasmid; the bottom-most vector is the therapeutic vector, as described herein.

Referring more specifically to FIG. 1, the Helper plus Rev plasmid includes a CAG enhancer (SEQ ID NO: 19); a CAG promoter (SEQ ID NO: 13); a chicken beta actin intron (SEQ ID NO: 20); a HIV gag (SEQ ID NO: 14); a HIV Pol (SEQ ID NO: 15); a HIV Int (SEQ ID NO: 16); a HIV RRE (SEQ ID NO: 17); a HIV Rev (SEQ ID NO: 18); and a rabbit beta globin poly A (SEQ ID NO: 21). The Helper plus Rev plasmid includes a CMV enhancer; a chicken beta actin promoter; a rabbit beta globin intron; a HIV gag; a HIV Pol; a HIV Int; a HIV RRE; a HIV Rev; and a rabbit beta globin poly A.

The Envelope plasmid includes a CMV promoter (SEQ ID NO: 22); a beta globin intron (SEQ ID NO: 23); a VSV-G (SEQ ID NO: 24); and a rabbit beta globin poly A (SEQ ID NO: 25).

Synthesis of a 2-Vector Lentiviral Packaging System Including Helper (Plus Rev) and Envelope Plasmids.

Materials and Methods:

Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAG-GAAGAT-3') (SEQ ID NO: 44) and reverse primer was (5'-CCATACAATGAATGGACACTAGGCGGCCGCAC-GAAT-3') (SEQ ID NO: 45)

The sequence for the Gag, Pol, Integrase fragment was as follows:

```
                                      (SEQ ID NO: 26)
GAATTCATGAATTTGCCAGGAAGATGGAAACCAAAAATGATAGGGGGAAT

TGGAGGTTTTATCAAAGTAAGACAGTATGATCAGATACTCATAGAAATCT

GCGGACATAAAGCTATAGGTACAGTATTAGTAGGACCTACACCTGTCAAC

ATAATTGGAAGAAATCTGTTGACTCAGATTGGCTGCACTTTAAATTTTCC

CATTAGTCCTATTGAGACTGTACCAGTAAAATTAAAGCCAGGAATGGATG

GCCCAAAAGTTAAACAATGGCCATTGACAGAAGAAAAATAAAAGCATTA

GTAGAAATTTGTACAGAAATGGAAAAGGAAGGAAAAATTTCAAAAATTGG

GCCTGAAAATCCATACAATACTCCAGTATTTGCCATAAAGAAAAAAGACA

GTACTAAATGGAGAAAATTAGTAGATTTCAGAGAACTTAATAAGAACT

CAAGATTTCTGGGAAGTTCAATTAGGAATACCACATCCTGCAGGGTTAAA

ACAGAAAAAATCAGTAACAGTACTGGATGTGGGCGATGCATATTTTTCAG
```

```
TTCCCTTAGATAAAGACTTCAGGAAGTATACTGCATTTACCATACCTAGT

ATAAACAATGAGACACCAGGGATTAGATATCAGTACAATGTGCTTCCACA

GGGATGGAAAGGATCACCAGCAATATTCCAGTGTAGCATGACAAAAATCT

TAGAGCCTTTTAGAAAACAAAATCCAGACATAGTCATCTATCAATACATG

GATGATTTGTATGTAGGATCTGACTTAGAAATAGGGCAGCATAGAACAAA

AATAGAGGAACTGAGACAACATCTGTTGAGGTGGGGATTTACCACACCAG

ACAAAAAACATCAGAAAGAACCTCCATTCCTTTGGATGGGTTATGAACTC

CATCCTGATAAATGGACAGTACAGCCTATAGTGCTGCCAGAAAAGGACAG

CTGGACTGTCAATGACATACAGAAATTAGTGGGAAAATTGAATTGGGCAA

GTCAGATTTATGCAGGGATTAAAGTAAGGCAATTATGTAAACTTCTTAGG

GGAACCAAAGCACTAACAGAAGTAGTACCACTAACAGAAGAAGCAGAGCT

AGAACTGGCAGAAAACAGGGAGATTCTAAAAGAACCGGTACATGGAGTGT

ATTATGACCCATCAAAAGACTTAATAGCAGAAATACAGAAGCAGGGGCAA

GGCCAATGGACATATCAAATTTATCAAGAGCCATTTAAAAATCTGAAAAC

AGGAAAGTATGCAAGAATGAAGGGTGCCCACACTAATGATGTGAAACAAT

TAACAGAGGCAGTACAAAAAATAGCCACAGAAAGCATAGTAATATGGGGA

AAGACTCCTAAATTTAAATTACCCATACAAAAGGAAACATGGGAAGCATG

GTGGACAGAGTATTGGCAAGCCACCTGGATTCCTGAGTGGGAGTTTGTCA

ATACCCCTCCCTTAGTGAAGTTATGGTACCAGTTAGAGAAAGAACCCATA

ATAGGAGCAGAAACTTTCTATGTAGATGGGGCAGCCAATAGGGAAACTAA

ATTAGGAAAAGCAGGATATGTAACTGACAGAGGAAGACAAAAAGTTGTCC

CCCTAACGGACACAACAAATCAGAAGACTGAGTTACAAGCAATTCATCTA

GCTTTGCAGGATTCGGGATTAGAAGTAAACATAGTGACAGACTCACAATA

TGCATTGGGAATCATTCAAGCACAACCAGATAAGAGTGAATCAGAGTTAG

TCAGTCAAATAATAGAGCAGTTAATAAAAAAGGAAAAAGTCTACCTGGCA

TGGGTACCAGCACACAAAGGAATTGGAGGAAATGAACAAGTAGATAAATT

GGTCAGTGCTGGAATCAGGAAAGTACTATTTTTAGATGGAATAGATAAGG

CCCAAGAAGAACATGAGAAATATCACAGTAATTGGAGAGCAATGGCTAGT

GATTTTAACCTACCACCTGTAGTAGCAAAAGAAATAGTAGCCAGCTGTGA

TAAATGTCAGCTAAAAGGGGAAGCCATGCATGGACAAGTAGACTGTAGCC

CAGGAATATGGCAGCTAGATTGTACACATTTAGAAGGAAAAGTTATCTTG

GTAGCAGTTCATGTAGCCAGTGGATATATAGAAGCAGAAGTAATTCCAGC

AGAGACAGGGCAAGAAACAGCATACTTCCTCTTAAAATTAGCAGGAAGAT

GGCCAGTAAAAACAGTACATACAGACAATGGCAGCAATTTCACCAGTACT

ACAGTTAAGGCCGCCTGTTGGTGGCGGGGATCAAGCAGGAATTTGGCAT

TCCCTACAATCCCCAAAGTCAAGGAGTAATAGAATCTATGAATAAAGAAT

TAAAGAAAATTATAGGACAGGTAAGAGATCAGGCTGAACATCTTAAGACA

GCAGTACAAATGGCAGTATTCATCCACAATTTTAAAAGAAAAGGGGGGAT

TGGGGGGTACAGTGCAGGGGAAAGAATAGTAGACATAATAGCAACAGACA

TACAAACTAAAGAATTACAAAAACAAATTACAAAAATTCAAAATTTTCGG
```

```
GTTTATTACAGGGACAGCAGAGATCCAGTTTGGAAAGGACCAGCAAAGCT

CCTCTGGAAAGGTGAAGGGGCAGTAGTAATACAAGATAATAGTGACATAA

AAGTAGTGCCAAGAAGAAAAGCAAAGATCATCAGGGATTATGGAAAACAG

ATGGCAGGTGATGATTGTGTGGCAAGTAGACAGGATGAGGATTAA
```

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 27)
```
TCTAGAATGGCAGGAAGAAGCGGAGACAGCGACGAAGAGCTCATCAGAAC

AGTCAGACTCATCAAGCTTCTCTATCAAAGCAACCCACCTCCCAATCCCG

AGGGGACCCGACAGGCCCGAAGGAATAGAAGAAGAAGGTGGAGAGAGAGA

CAGAGACAGATCCATTCGATTAGTGAACGGATCCTTGGCACTTATCTGGG

ACGATCTGCGGAGCCTGTGCCTCTTCAGCTACCACCGCTTGAGAGACTTA

CTCTTGATTGTAACGAGGATTGTGGAACTTCTGGGACGCAGGGGGTGGGA

AGCCCTCAAATATTGGTGGAATCTCCTACAATATTGGAGTCAGGAGCTAA

AGAATAGAGGAGCTTTGTTCCTTGGGTTCTTGGGAGCAGCAGGAAGCACT

ATGGGCGCAGCGTCAATGACGCTGACGGTACAGGCCAGACAATTATTGTC

TGGTATAGTGCAGCAGCAGAACAATTTGCTGAGGGCTATTGAGGCGCAAC

AGCATCTGTTGCAACTCACAGTCTGGGGCATCAAGCAGCTCCAGGCAAGA

ATCCTGGCTGTGGAAAGATACCTAAAGGATCAACAGCTCCTAGATCTTTT

TCCCTCTGCCAAAAATTATGGGGACATCATGAAGCCCCTTGAGCATCTGA

CTTCTGGCTAATAAAGGAAATTTATTTTCATTGCAATAGTGTGTTGGAAT

TTTTTGTGTCTCTCACTCGGAAGGACATATGGGAGGGCAAATCATTTAAA

ACATCAGAATGAGTATTTGGTTTAGAGTTTGGCAACATATGCCATATGCT

GGCTGCCATGAACAAAGGTGGCTATAAAGAGGTCATCAGTATATGAAACA

GCCCCCTGCTGTCCATTCCTTATTCCATAGAAAAGCCTTGACTTGAGGTT

AGATTTTTTTATATTTTGTTTTGTGTTATTTTTTCTTTAACATCCCTA

AAATTTTCCTTACATGTTTTACTAGCCAGATTTTTCCTCCTCTCCTGACT

ACTCCCAGTCATAGCTGTCCCTCTTCTCTTATGAAGATCCCTCGACCTGC

AGCCCAAGCTTGGCGTAATCATGGTCATAGCTGTTTCCTGTGTGAAATTG

TTATCCGCTCACAATTCCACACAACATACGAGCCGGAAGCATAAAGTGTA

AAGCCTGGGGTGCCTAATGAGTGAGCTAACTCACATTAATTGCGTTGCGC

TCACTGCCCGCTTTCCAGTCGGGAAACCTGTCGTGCCAGCGGATCCGCAT

CTCAATTAGTCAGCAACCATAGTCCCGCCCCTAACTCCGCCCATCCCGCC

CCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAG

AAGTAGTGAGGAGGCTTTTTTGGAGGCCTAGGCTTTTGCAAAAAGCTAAC

TTGTTTATTGCAGCTTATAATGGTTACAAATAAAGCAATAGCATCACAAA
```

-continued

TTTCACAAATAAAGCATTTTTTTCACTGCATTCTAGTTGTGGTTTGTCCA

AACTCATCAATGTATCTTATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 28)
ACGCGTTAGTTATTAATAGTAATCAATTACGGGGTCATTAGTTCATAGCC

CATATATGGAGTTCCGCGTTACATAACTTACGGTAAATGGCCCGCCTGGC

TGACCGCCCAACGACCCCCGCCCATTGACGTCAATAATGACGTATGTTCC

CATAGTAACGCCAATAGGGACTTTCCATTGACGTCAATGGGTGGACTATT

TACGGTAAACTGCCCACTTGGCAGTACATCAAGTGTATCATATGCCAAGT

ACGCCCCCTATTGACGTCAATGACGGTAAATGGCCCGCCTGGCATTATGC

CCAGTACATGACCTTATGGGACTTTCCTACTTGGCAGTACATCTACGTAT

TAGTCATCGCTATTACCATGGGTCGAGGTGAGCCCCACGTTCTGCTTCAC

TCTCCCCATCTCCCCCCCCTCCCCACCCCCAATTTTGTATTTATTTATTT

TTTAATTATTTTGTGCAGCGATGGGGCGGGGGGGGGGGGCGCGCGCC

AGGCGGGGCGGGCGGGCGAGGGCGGGCGGGGCGAGGCGGAGAGGTG

CGGCGGCAGCCAATCAGAGCGGCGCGCTCCGAAAGTTTCCTTTTATGGCG

AGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCC

GCCCGCCCCGGCTCTGACTGACCGCGTTACTCCCACAGGTGAGCGGGCGG

GACGGCCCTTCTCCTCCGGGCTGTAATTAGCGCTTGGTTTAATGACGGCT

CGTTTCTTTTCTGTGGCTGCGTGAAAGCCTTAAAGGGCTCCGGGAGGGCC

CTTTGTGCGGGGGGAGCGGCTCGGGGGTGCGTGCGTGTGTGTGCGT

GGGGAGCGCCGCGTGCGGCCCGCGCTGCCCGGCGGCTGTGAGCGCTGCGG

GCGCGGCGCGGGCTTTGTGCGCTCCGCGTGTGCGCGAGGGGAGCGCGGC

CGGGGGCGGTGCCCCGCGGTGCGGGGGGCTGCGAGGGGAACAAAGGCTG

CGTGCGGGTGTGTGCGTGGGGGGTGAGCAGGGGGTGTGGGCGCGGCGG

TCGGGCTGTAACCCCCCCCTGCACCCCCCTCCCCGAGTTGCTGAGCACGG

CCCGGCTTCGGGTGCGGGCTCCGTGCGGGCGTGGCGCGGGGCTCGCCG

TGCCGGGCGGGGGTGGCGGCAGGTGGGGGTGCCGGGCGGGCGGGGCCG

CCTCGGGCCGGGAGGGCTCGGGGAGGGGCGCGGCGGCCCCGGAGCGCC

GGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCGAA

ATCTGGGAGGCGCCGCCGCACCCCCTCTAGCGGGCGCGGGCGAAGCGGTG

CGGCGCCGGCAGGAAGGAAATGGGCGGGGAGGGCCTTCGTGCGTCGCCGC

GCCGCCGTCCCCTTCTCCATCTCCAGCCTCGGGGCTGCCGCAGGGGGACG

-continued

GCTGCCTTCGGGGGGGACGGGGCAGGGCGGGGTTCGGCTTCTGGCGTGTG

ACCGGCGGGAATTC

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

(SEQ ID NO: 24)
GAATTCATGAAGTGCCTTTTGTACTTAGCCTTTTTATTCATTGGGGTGAA

TTGCAAGTTCACCATAGTTTTTCCACACAACCAAAAAGGAAACTGGAAAA

ATGTTCCTTCTAATTACCATTATTGCCCGTCAAGCTCAGATTTAAATTGG

CATAATGACTTAATAGGCACAGCCTTACAAGTCAAAATGCCCAAGAGTCA

CAAGGCTATTCAAGCAGACGGTTGGATGTGTCATGCTTCCAAATGGGTCA

CTACTTGTGATTTCCGCTGGTATGGACCGAAGTATATAACACATTCCATC

CGATCCTTCACTCCATCTGTAGAACAATGCAAGGAAAGCATTGAACAAAC

GAAACAAGGAACTTGGCTGAATCCAGGCTTCCCTCCTCAAAGTTGTGGAT

ATGCAACTGTGACGGATGCCGAAGCAGTGATTGTCCAGGTGACTCCTCAC

CATGTGCTGGTTGATGAATACACAGGAGAATGGGTTGATTCACAGTTCAT

CAACGGAAAATGCAGCAATTACATATGCCCCACTGTCCATAACTCTACAA

CCTGGCATTCTGACTATAAGGTCAAAGGGCTATGTGATTCTAACCTCATT

TCCATGGACATCACCTTCTTCTCAGAGGACGGAGAGCTATCATCCCTGGG

AAAGGAGGGCACAGGGTTCAGAAGTAACTACTTTGCTTATGAAACTGGAG

GCAAGGCCTGCAAAATGCAATACTGCAAGCATTGGGGAGTCAGACTCCCA

TCAGGTGTCTGGTTCGAGATGGCTGATAAGGATCTCTTTGCTGCAGCCAG

ATTCCCTGAATGCCCAGAAGGGTCAAGTATCTCTGCTCCATCTCAGACCT

CAGTGGATGTAAGTCTAATTCAGGACGTTGAGAGGATCTTGGATTATTCC

CTCTGCCAAGAAACCTGGAGCAAAATCAGAGCGGGTCTTCCAATCTCTCC

AGTGGATCTCAGCTATCTTGCTCCTAAAAACCCAGGAACCGGTCCTGCTT

TCACCATAATCAATGGTACCCTAAAATACTTTGAGACCAGATACATCAGA

GTCGATATTGCTGCTCCAATCCTCTCAAGAATGGTCGGAATGATCAGTGG

AACTACCACAGAAAGGGAACTGTGGGATGACTGGGCACCATATGAAGACG

TGGAAATTGGACCCAATGGAGTTCTGAGGACCAGTTCAGGATATAAGTTT

CCTTTATACATGATTGGACATGGTATGTTGGACTCCGATCTTCATCTTAG

CTCAAAGGCTCAGGTGTTCGAACATCCTCACATTCAAGACGCTGCTTCGC

AACTTCCTGATGATGAGAGTTTATTTTTTGGTGATACTGGGCTATCCAAA

AATCCAATCGAGCTTGTAGAAGGTTGGTTCAGTAGTTGGAAAAGCTCTAT

TGCCTCTTTTTTCTTTATCATAGGGTTAATCATTGGACTATTCTTGGTTC

TCCGAGTTGGTATCCATCTTTGCATTAAATTAAAGCACACCAAGAAAGA

CAGATTTATACAGACATAGAGATGAGAATTC

A 4-vector system (i.e., a 3-vector lentiviral packaging system) has also been designed and produced using the methods and materials described herein. A schematic of the 4-vector system is shown in FIG. 2. Briefly, and with reference to FIG. 2, the top vector is a helper plasmid, which, in this case, does not include Rev; the vector that is second from the top is a separate Rev plasmid; the vector that is second from the bottom is the envelope plasmid; the bottom vector is the previously described therapeutic vector.

As shown in FIG. 1, the Helper plasmid includes a CAG enhancer (SEQ ID NO: 19); a CAG promoter (SEQ ID NO: 13); a chicken beta actin intron (SEQ ID NO: 20); a HIV gag (SEQ ID NO: 14); a HIV Pol (SEQ ID NO: 15); a HIV Int (SEQ ID NO: 16); a HIV RRE (SEQ ID NO: 17); and a rabbit beta globin poly A (SEQ ID NO: 21). The Helper plasmid includes a CMV enhancer; a chicken beta actin promoter; a rabbit beta globin intron; a HIV gag; a HIV Pol; a HIV Int; a HIV RRE; and a rabbit beta globin poly A.

As shown in FIG. 2, the Rev plasmid includes an RSV promoter (SEQ ID NO: 29); a HIV Rev (SEQ ID NO: 18); and a rabbit beta globin poly A (SEQ ID NO: 21).

As shown in FIG. 1 and FIG. 2, the Envelope plasmid includes a CMV promoter (SEQ ID NO: 22); a beta globin intron (SEQ ID NO: 23); a VSV-G (SEQ ID NO: 24); and a rabbit beta globin poly A (SEQ ID NO: 25).

Synthesis of a 3-Vector Lentiviral Packaging System Including Helper, Rev, and Envelope Plasmids.
Materials and Methods:
Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

(SEQ ID NO: 30)
TCTAGAAGGAGCTTTGTTCCTTGGGTTCTTGGGAGCAGCAGGAAGCACTA

TGGGCGCAGCGTCAATGACGCTGACGGTACAGGCCAGACAATTATTGTCT

GGTATAGTGCAGCAGCAGAACAATTTGCTGAGGGCTATTGAGGCGCAACA

GCATCTGTTGCAACTCACAGTCTGGGGCATCAAGCAGCTCCAGGCAAGAA

TCCTGGCTGTGGAAAGATACCTAAAGGATCAACAGCTCCTAGATCTTTTT

CCCTCTGCCAAAAATTATGGGGACATCATGAAGCCCCTTGAGCATCTGAC

TTCTGGCTAATAAAGGAAATTTATTTTCATTGCAATAGTGTGTTGGAATT

TTTTGTGTCTCTCACTCGGAAGGACATATGGGAGGGCAAATCATTTAAAA

CATCAGAATGAGTATTTGGTTTAGAGTTTGGCAACATATGCCATATGCTG

GCTGCCATGAACAAAGGTGGCTATAAAGAGGTCATCAGTATATGAAACAG

CCCCCTGCTGTCCATTCCTTATTCCATAGAAAAGCCTTGACTTGAGGTTA

GATTTTTTTTATATTTTGTTTGTGTTATTTTTTTCTTTAACATCCCTAA

AATTTTCCTTACATGTTTTACTAGCCAGATTTTTCCTCCTCTCCTGACTA

CTCCCAGTCATAGCTGTCCCTCTTCTCTTATGAAGATCCCTCGACCTGCA

GCCCAAGCTTGGCGTAATCATGGTCATAGCTGTTTCCTGTGTGAAATTGT

TATCCGCTCACAATTCCACACAACATACGAGCCGGAAGCATAAAGTGTAA

AGCCTGGGGTGCCTAATGAGTGAGCTAACTCACATTAATTGCGTTGCGCT

CACTGCCCGCTTTCCAGTCGGGAAACCTGTCGTGCCAGCGGATCCGCATC

TCAATTAGTCAGCAACCATAGTCCCGCCCCTAACTCCGCCCATCCCGCCC

CTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGA

AGTAGTGAGGAGGCTTTTTTGGAGGCCTAGGCTTTTGCAAAAAGCTAACT

TGTTTATTGCAGCTTATAATGGTTACAAATAAAGCAATAGCATCACAAAT

TTCACAAATAAAGCATTTTTTTCACTGCATTCTAGTTGTGGTTTGTCCAA

ACTCATCAATGTATCTTATCACCCGGG

Construction of the Rev Plasmid:
The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

(SEQ ID NO: 29)
CAATTGCGATGTACGGGCCAGATATACGCGTATCTGAGGGGACTAGGGTG

TGTTTAGGCGAAAAGCGGGGCTTCGGTTGTACGCGGTTAGGAGTCCCCTC

AGGATATAGTAGTTTCGCTTTTGCATAGGGAGGGGGAAATGTAGTCTTAT

GCAATACACTTGTAGTCTTGCAACATGGTAACGATGAGTTAGCAACATGC

CTTACAAGGAGAGAAAAAGCACCGTGCATGCCGATTGGTGGAAGTAAGGT

GGTACGATCGTGCCTTATTAGGAAGGCAACAGACAGGTCTGACATGGATT

GGACGAACCACTGAATTCCGCATTGCAGAGATAATTGTATTTAAGTGCCT

AGCTCGATACAATAAACGCCATTTGACCATTCACCACATTGGTGTGCACC

TCCAAGCTCGAGCTCGTTTAGTGAACCGTCAGATCGCCTGGAGACGCCAT

CCACGCTGTTTTGACCTCCATAGAAGACACCGGGACCGATCCAGCCTCCC

CTCGAAGCTAGCGATTAGGCATCTCCTATGGCAGGAAGAAGCGGAGACAG

CGACGAAGAACTCCTCAAGGCAGTCAGACTCATCAAGTTTCTCTATCAAA

GCAACCCACCTCCCAATCCCGAGGGGACCCGACAGGCCCGAAGGAATAGA

AGAAGAAGGTGGAGAGAGAGACAGAGACAGATCCATTCGATTAGTGAACG

GATCCTTAGCACTTATCTGGGACGATCTGCGGAGCCTGTGCCTCTTCAGC

TACCACCGCTTGAGAGACTTACTCTTGATTGTAACGAGGATTGTGGAACT

TCTGGGACGCAGGGGGTGGGAAGCCCTCAAATATTGGTGGAATCTCCTAC

AATATTGGAGTCAGGAGCTAAAGAATAGTCTAGA

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 31), phosphoglycerate kinase (PGK) (SEQ ID NO: 32), and ubiquitin C (UbC) (SEQ ID NO: 33) can replace the CMV (SEQ ID NO: 22) or CAG promoter (SEQ ID NO: 13). These sequences can also be further varied by addition, substitution, deletion or mutation.

Poly A sequences: SV40 poly A (SEQ ID NO: 34) and bGH poly A (SEQ ID NO: 35) can replace the rabbit beta globin poly A (SEQ ID NO: 21). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 14); HIV Pol (SEQ ID NO: 15); and HIV Int (SEQ ID NO: 16) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 36), gibbon ape leukemia virus (GALV) (SEQ ID NO: 37), Rabies (FUG) (SEQ ID NO: 38), lymphocytic choriomeningitis virus (LCMV) (SEQ ID NO: 39), influenza A fowl plague virus (FPV) (SEQ ID NO: 40), Ross River alphavirus (RRV) (SEQ ID NO: 41), murine leukemia virus 10A1 (MLV) (SEQ ID NO: 42), or Ebola virus (EboV) (SEQ ID NO: 43). Sequences for these envelopes are identified in the sequence table herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'δ LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3'delta LTR. Sequences corresponding with the above elements are identified in the sequence listings portion herein.

Example 2: Lentiviral Particle-Delivered shRNA-Based RNA Interference Targeting the Human KIF11 (Eg5) Untranslated Region Results in Significantly Reduced Levels of KIF11 mRNA PC3 human prostate carcinoma cells were infected with lentiviral vector particles containing the H1 promoter and either a non-targeting shRNA (used as a control) (SEQ ID NO: 56) or any one of three different KIF11 shRNA sequences: KIF11 shRNA sequence #1 (SEQ ID NO: 1); KIF11 shRNA sequence #2 (SEQ ID NO: 2); and KIF11 shRNA sequence #3 (SEQ ID NO: 3).

PC3 human prostate carcinoma cells were seeded in 24-well plates at $5 \times 10^4$ cells per well. After 24 hours, the cells were transduced at 5 MOI with lentiviral vector particles containing the H1 promoter and one of three different KIF11 UTR shRNA sequences (SEQ ID NO: 1, SEQ ID NO: 2, or SEQ ID NO: 3) or a lentiviral vector particle expressing only GFP. After 72 hours, RNA was extracted from the cells with the RNeasy kit (Qiagen) and converted to cDNA with SuperScript VILO (Thermo). Expression of KIF11 cDNA was determined by quantitative PCR using a FAM-labeled KIF11 TaqMan probe (SEQ ID NO: 48) and primers for KIF11 (forward primer (SEQ ID NO: 46); reverse primer (SEQ ID NO: 47)). KIF11 RNA expression was normalized to actin levels for each sample (Actin forward primer (SEQ ID NO: 49); Actin reverse primer #1 (SEQ ID NO: 50); Actin probe (SEQ ID NO: 52)).

Figure 5:
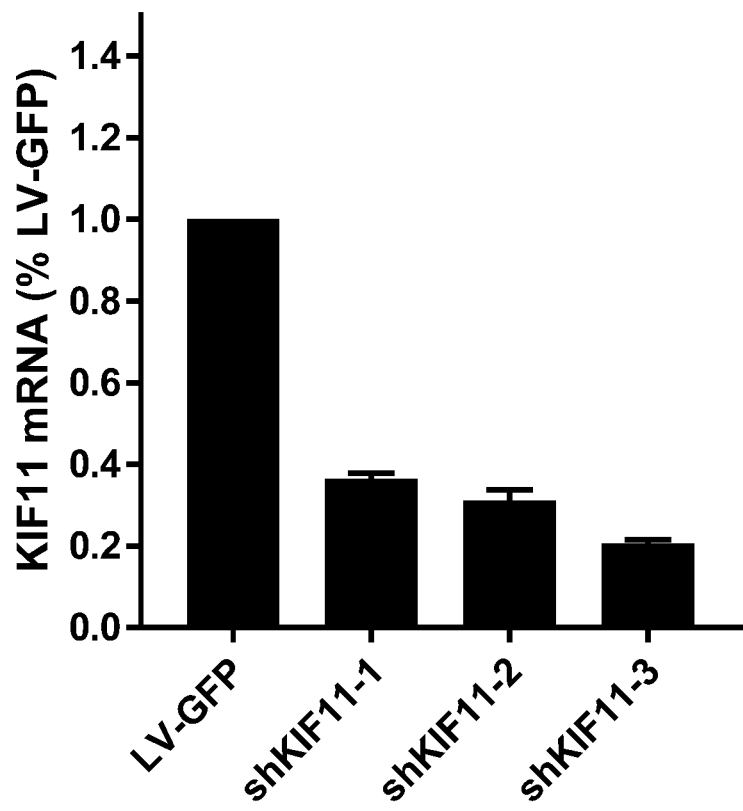
FIG. 5 depicts data demonstrating effect of lentiviral-delivered shRNA-based RNA interference that targets the human KIF11 untranslated region.

Levels of KIF11 mRNA relative to the % LV-GFP is shown in FIG. 5. As compared to LV-GFP transduced cells, KIF11 RNA: (i) decreased 63% using KIF11 shRNA sequence #1 (SEQ ID NO: 1) (see, bar showing KIF11 mRNA expression after transduction with shKIF11-1), (ii) decreased 69% using KIF11 shRNA sequence #2 (SEQ ID NO: 2) (see, bar showing KIF11 mRNA expression after transduction with shKIF11-2), and (iii) decreased 79% using KIF11 shRNA sequence #3 (SEQ ID NO: 3) (see, bar showing KIF11 mRNA expression after transduction with shKIF11-3).

Example 3: Lentiviral Particle-Delivered Co-Expression of Both (i) a shRNA-Based RNA Interference Targeting the Human KIF11 Untranslated Region and (ii) a KIF11 Coding Sequence, Results in High Expression Levels of KIF11

Figure 3:
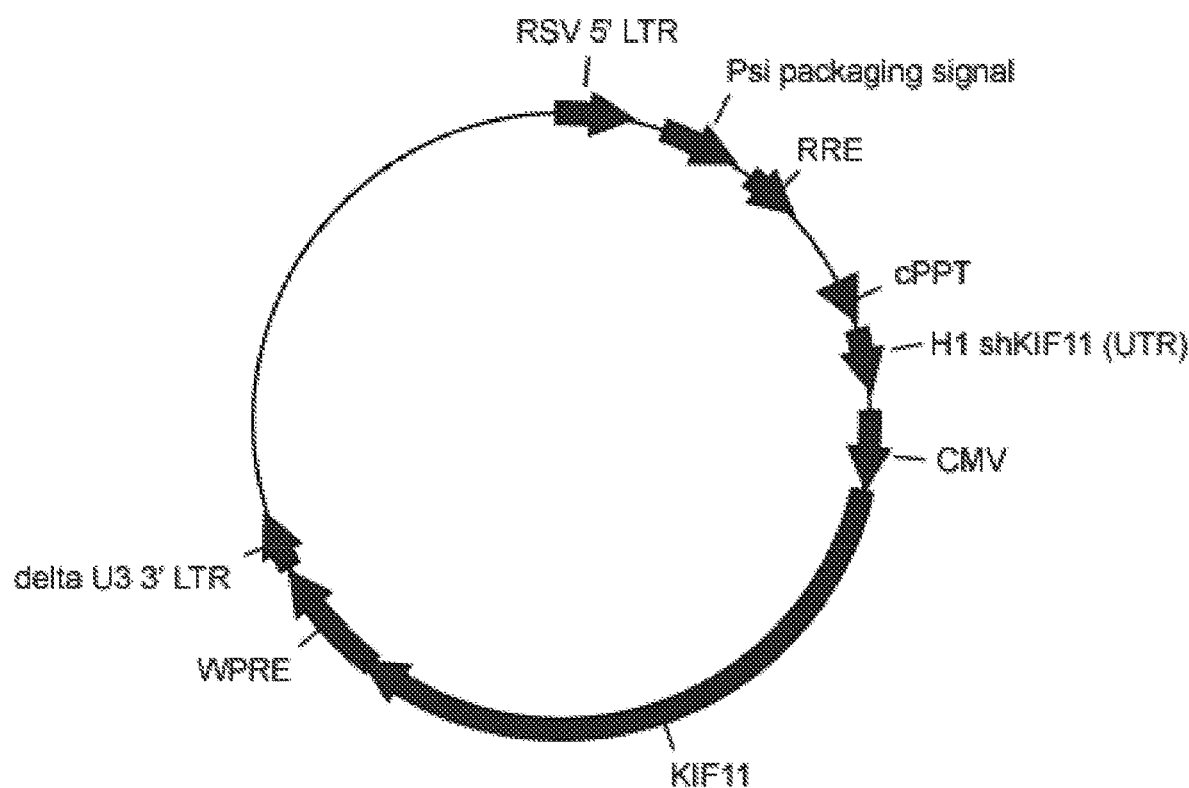
FIG. 3 depicts a lentiviral vector expressing KIF11 shRNA targeting sequence and the KIF11 coding sequence, in a circularized form.

PC3 human prostate carcinoma cells were infected with a lentiviral vector particle containing the H1 promoter regulating the expression of KIF11 shRNA (KIF11 shRNA sequence #3 (SEQ ID NO: 3)) and a lentiviral vector particle containing both: (i) the H1 promoter regulating the expression of KIF11 shRNA (KIF11 shRNA sequence #3) (SEQ ID NO: 3)); and (ii) a CMV promoter regulating the expression of the KIF11 sequence comprising its coding sequence and a truncated 3'UTR (SEQ ID NO: 4). An embodiment of the vector used in this experiment is provided in FIG. 3 (circularized form) and FIG. 4 (linear form).

PC3 human prostate carcinoma cells were seeded in 24-well plates at $5 \times 10^4$ cells per well. After 24 hours, the cells were transduced at 5 MOI with a lentiviral vector particle expressing KIF11 UTR shRNA #3 (SEQ ID NO: 3) and a CMV promoter regulating the expression of the KIF11 coding sequence (SEQ ID NO: 4). After 72 hours, RNA was extracted from the cells with the RNeasy kit (Qiagen) and converted to cDNA with SuperScript VILO (Thermo). Expression of KIF11 cDNA was determined by quantitative PCR using a FAM-labeled KIF11 TaqMan probe (SEQ ID NO: 48) and primers for KIF11 (forward primer (SEQ ID NO: 46); reverse primer (SEQ ID NO: 47)). KIF11 expression was normalized to actin levels for each sample (Actin forward primer (SEQ ID NO: 49); Actin reverse primer #1 (SEQ ID NO: 50); and Actin probe (SEQ ID NO: 52)).

Figure 6:
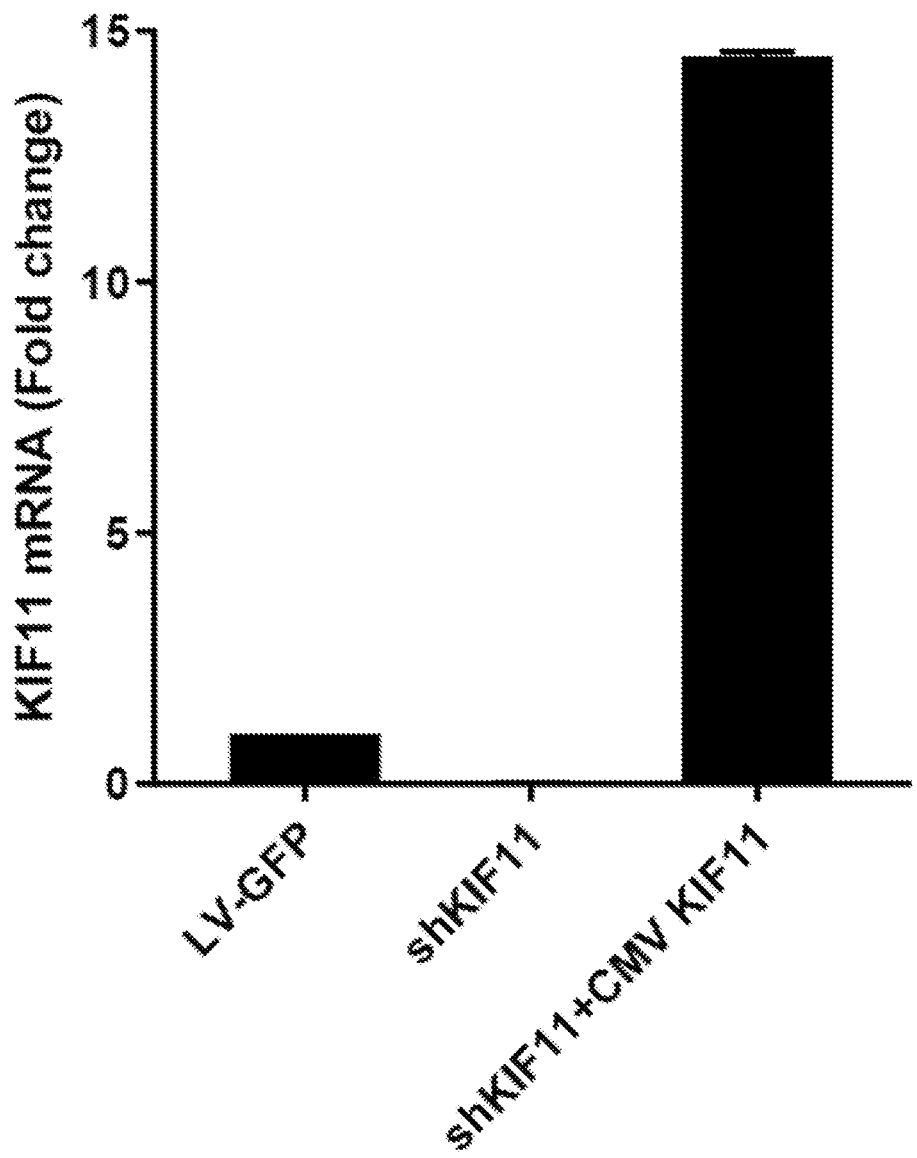
FIG. 6 depicts data demonstrating effect on KIF11 mRNA levels after lentiviral-delivered co-expression of both a shRNA-based RNA targeting the human KIF11 untranslated region and a KIF11 gene.

As shown in FIG. 6, relative to the control treated LV-GFP treated cells, KIF11 mRNA: (i) decreased 77% when cells were transduced with the vector expressing the KIF11 shRNA sequence #3 (SEQ ID NO: 3) (see, bar showing KIF11 mRNA expression after transduction with shKIF11); and (ii) increased 14.5-fold when cells were transduced with the vector expressing the KIF11 shRNA sequence #3 (SEQ ID NO: 3) and the KIF11 sequence (SEQ ID NO: 4) (see, bar showing KIF11 mRNA expression after transduction with shKIF11+CMV KIF11). This shows that shRNA is suppressing endogenous KIF11 mRNA and not affecting expression of KIF11 from the transgene.

Example 4: Lentiviral Particle-Delivered shRNA-Based RNA Interference Targeting the Human KIF11 (Eg5) Untranslated Region, Results in Reduced Numbers of Viable Cells PC3 human prostate carcinoma cells were transduced with a lentiviral vector particle containing the H1 promoter and either KIF11 shRNA sequence #2 (SEQ ID NO: 2) or sequence #3 (SEQ ID NO: 3).

PC3 human prostate carcinoma cells were seeded in 24-well plates at $5 \times 10^4$ cells per well. After 24 hours, the cells were transduced at 5 MOI with a lentiviral vector particle expressing either KIF11 UTR shRNA #2 or #3 (SEQ ID NO: 2 or SEQ ID NO: 3, respectively). After 4 days, cell number was determined with the MTT reagent (Sigma) at 570 nm. The MTT reagent is a tetrazolium dye (3-(4,5,-dimethylthiazol-2-yl)-2,5-diphenyltetrazolium bromide. In metabolically active, viable cells the NAD(P)H-dependent oxidoreductase enzymes cause reduction of the MTT reagent to its insoluble form known as formazan, which is purple in color. An MTT assay for cell viability was performed by adding the MTT reagent to a cell suspension then examining cells under the microscope to enumerate the proportion appearing purple. Automated versions of the MTT assay distributes cells to individual wells of a plastic plate followed by colorimetry to measure the intensity of purple color.

Figure 7:
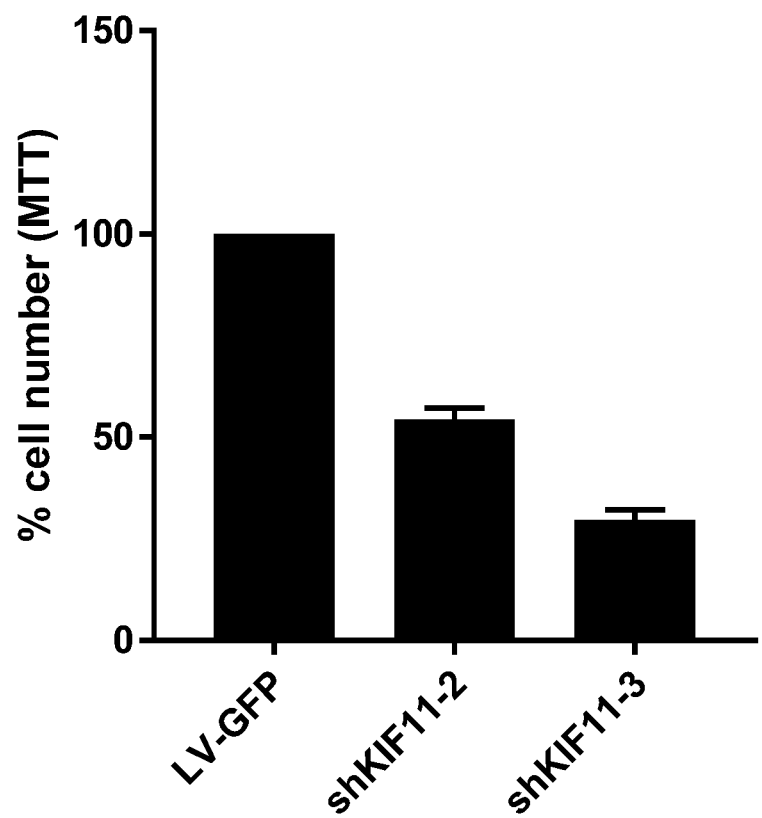
FIG. 7 depicts data demonstrating the effect of KIF11 knockdown on the proliferation of PC3 cells.

As shown in FIG. 7, as compared to LV-GFP transduced cells, the number of cells: (i) decreased 46% in cells transduced with the KIF11 shRNA #2 sequence (SEQ ID NO: 2) (see, bar showing % cell number after transduction with shKIF11-2); and (ii) decreased 70% in cells transduced with the KIF11 shRNA #3 sequence (SEQ ID NO: 3) (see, bar showing % cell number after transduction with shKIF11-3). This suggests that KIF11 is a valid target for reducing cancer cell proliferation.

Example 5: Lentiviral Particle-Delivered Co-Expression of Both (i) a shRNA-Based RNA Interference Targeting the Human KIF11 Untranslated Region and (ii) a KIF11 Coding Sequence, Results in Maintaining High Levels of Cell Number PC3 human prostate carcinoma cells were transduced with lentiviral vector particles expressing (i) GFP (control), (ii) shKIF11 (UTR), and (iii) a shKIF11 (UTR) and a sequence that encodes KIF11 (SEQ ID NO: 4) driven by a CMV promoter. The shKIF11 (UTR) sequence used in each of the lentiviral vector particles was the KIF shRNA sequence #3 (SEQ ID NO: 3). The sequence that encodes KIF11 (SEQ ID NO: 4) comprised a truncation in the 3'UTR of the KIF11 gene.

PC3 human prostate carcinoma cells were seeded in 24-well plates at $5 \times 10^4$ cells per well. After 24 hours, the cells were transduced at 5 MOI with lentiviral vector particles expressing KIF11 UTR shRNA #3 (SEQ ID NO: 3) alone or co-expressed with the KIF11 coding sequence as well as the lentiviral vector particle expressing only GFP (control). After 4 days, cell number was determined by culturing with the MTT reagent ((3-(4,5-dimethylthiazol-2-yl)-2,5-diphenyl tetrazolium bromide) (SigmaMillipore) which produces a dark blue formazan product in live cells. The MTT assay was carried out as described in Example 4.

Figure 8:
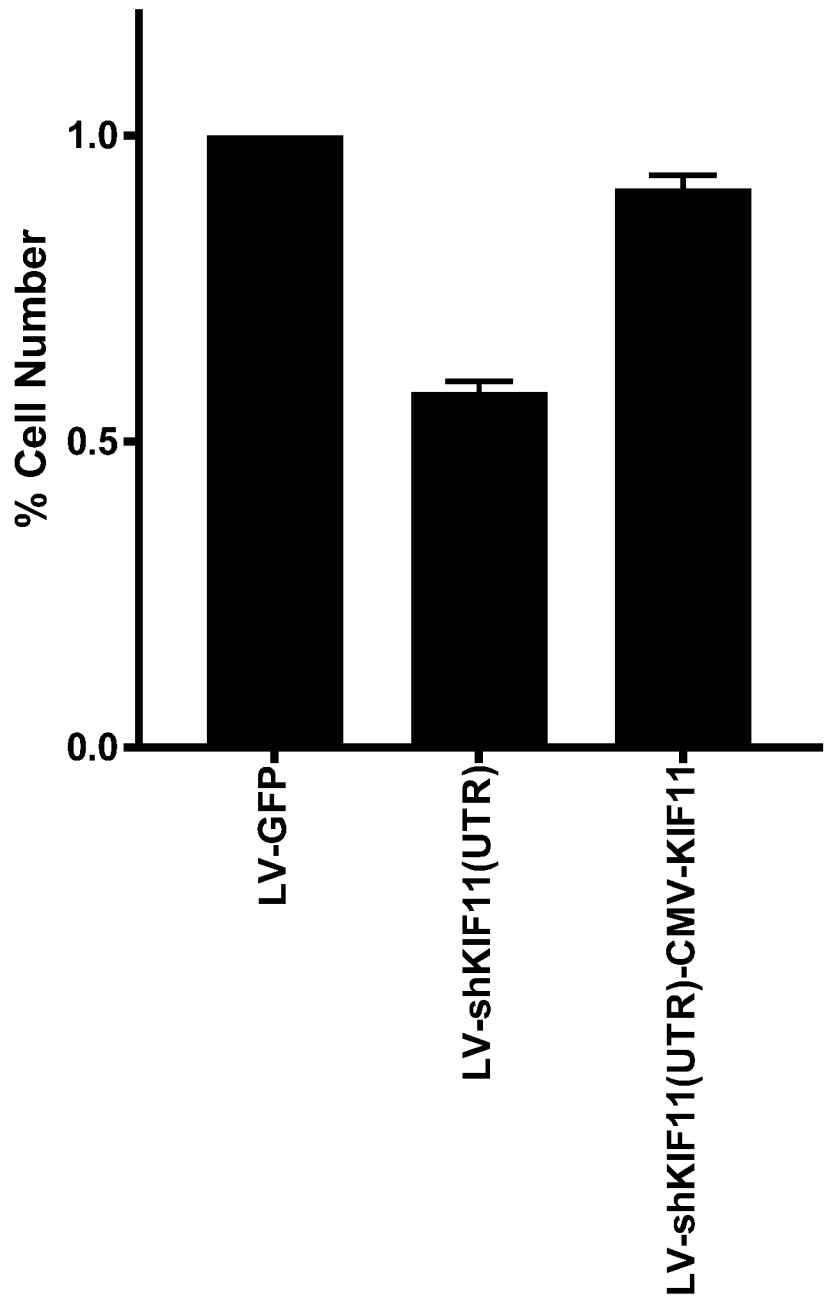
FIG. 8 depicts data demonstrating effect on proliferation of PC3 cells after lentiviral-delivered co-expression of both a shRNA-based RNA targeting the human KIF11 untranslated region and a KIF gene.

As shown in FIG. 8, as compared to LV-GFP transduced cells (see, bar showing % cell number after transduction with LV-GFP) (control vector set at 100%), the number of cells decreased 42% in cells that were transduced with the KIF11 shRNA sequence #3 (SEQ ID NO: 3) (see, bar showing % cell number after transduction with LV-shKIF11 (UTR). This reduction in number of cells was rescued to only a 9% decrease in cells that were transduced with the vector expressing the KIF11 shRNA sequence #3 (SEQ ID NO: 3) and the KIF11 coding sequence (see, bar showing % cell number after transduction with LV-shKIF11(UTR)-CMV-KIF11). Therefore, proliferation of PC3 was minimally affected by KIF11 shRNA when an exogenous KIF11 was expressed that contained a truncated 3'UTR.

Example 6: Mesenchymal Stem Cells can be Modified to Produce Inhibitory RNA Against a Required Cell Cycle Protein and Retain Growth Potential by Using a 2-Component Lentivirus Vector This Example illustrates use of a 2-component lentivirus vector to enable the bulk manufacturing from seed stock, of a mesenchymal stem cell product that proliferates in culture while also expressing high levels of inhibitory RNA blocking a critical function for cell growth.

The kinesin family member protein KIF11 is required for spindle formation and mitosis. It has been observed that inhibitory RNA capable of reducing the levels of KIF11 will reduce malignant tumor growth. Consequently, delivery of such an inhibitory RNA to the tumor microenvironment will be of therapeutic value. One method for delivering inhibitory RNA involves the use of mesenchymal stem cells. The cells have special properties for engaging cell-to-cell contact with tumor cells and delivering various molecules via a portal formed by connexin proteins.

Normal manufacturing for therapeutic doses of mesenchymal stem cells starts with a seed stock of highly characterized cells, which are expanded through several days of cell growth to achieve the numbers of cells required for in vivo therapy. Clearly, alternative strategies are needed to manufacture therapeutic doses of genetically modify mesenchymal stem cells that are programmed to produce high levels of an inhibitory RNA destined to suppress tumor cell growth.

The 2-component lentivirus vector system overcomes the problem of manufacturing modified mesenchymal stem cells. In this embodiment, the lentivirus vector expresses a modified version of the KIF11 gene containing the normal protein coding sequence but lacking the 3' untranslated region found normally in messenger RNA. From a separate cassette, the same lentivirus vector also expresses one or more inhibitory RNA in the form of a siRNA, shRNA, or microRNA that is targeted against the 3' untranslated region of normal KIF11 mRNA. In this way the modified mesenchymal stem cell expresses sufficient levels of KIF11 protein to maintain cell growth and also produces high levels of the inhibitory RNA that can be exported via connexin channels into tumor cells where it will suppress malignant growth. This is accomplished without sacrificing the ability to manufacture large cell doses of modified mesenchymal stem cells from a seed stock. Thus, the seed stock has been modified by a 2-component lentivirus vector, characterized in advance, qualified for clinical use and available as a cell and gene therapy for multiple tumor types.

Figure 9:
FIG. 9 depicts data demonstrating transduction of mesenchymal stem cells with a lentiviral vector expressing GFP.

Example 7: Transduction of Mesenchymal Stem Cells (MSCs) with a Lentiviral Vector Particle Expressing GFP Results in a Dose-Dependent Increase in GFP Expression MSCs were passaged three times and then seeded in 24 well plates at $2 \times 10^4$ cells per well. After 24 hours, the cells were transduced with a lentiviral vector (LV) particle expressing GFP at 4 and 20 multiplicity of infection (MOI) (based on a 293T titer value). After three days, the cells were imaged for GFP Fluorescence. As shown in FIG. 9, there was a dose-dependent increase in GFP brightness of the cells. As shown in the middle panel (LV-GFP 4 MOI), about 80% of the MSCs stained positive for GFP. As shown in the right panel (LV-GFP 20 MOI), close to 100% of the MSCs stained positive for GFP.

Example 8: Multiplicity of Infection Equal to 4 was Sufficient to Achieve 10 Vector Genomes Per Mesenchymal Stem Cell (MSC)

MSCs were passaged three times and then seeded in 6-well plates at $1 \times 10^5$ cells per well. After 24 hours, the cells were transduced with lentiviral vector particles expressing KIF11 shRNA sequence #3 (SEQ ID NO: 3) alone or KIF11 shRNA sequence #3 (SEQ ID NO: 3) with the KIF11 sequence (SEQ ID NO: 4). The vector particles also expressed GFP as a transduction marker. After 72 hours, genomic DNA was extracted with the DNeasy kit (Qiagen). A duplex PCR reaction was performed with 25 and 50 ng of DNA on a QuantStudio 3 qPCR machine using vector-specific Gag primers (Gag forward primer (SEQ ID NO: 53); Gag reverse primer (SEQ ID NO: 54)) and a FAM-labeled probe (SEQ ID NO: 55)) and Actin primers (Actin forward primer (SEQ ID NO: 49); Actin reverse primer #2 (SEQ ID NO: 51)) and a VIC-labeled probe (SEQ ID NO: 52)), as a cell control. The number of vector copies from the cell samples were determined with a standard curve using a lentiviral plasmid containing the Gag and actin sequences. The vector copy number was calculated using the formula: (Quantity Mean of Gag sequence/Quantity mean of Actin sequence).

Figure 10:
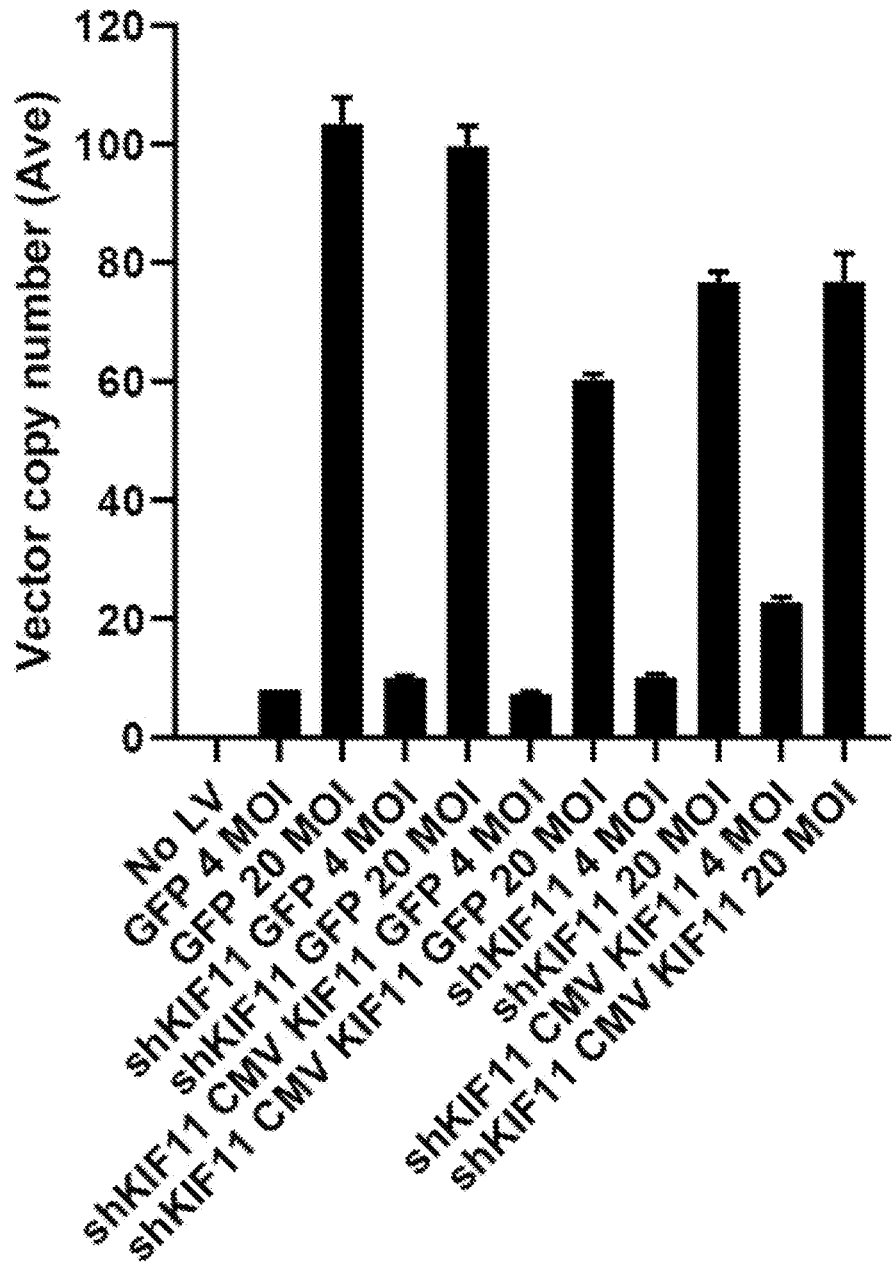
FIG. 10 depicts data demonstrating vector copy number of mesenchymal stem cells after transduction with various lentiviral vectors expressing shRNA against KIF11.

Results showing the vector copy number are shown in FIG. 10. In each of the vector particles in which 4 MOI was used, the vector copy number was between 7 and 20 (see, bars showing vector copy number of vectors transduced at 4 MOI: (i) GFP 4 MOI, (ii) shKIF11 GFP 4 MOI, (iii) shKIF11 CMV KIF11 GFP 4 MOI, (iv) shKIF11 4 MOI, and (iv) shKIF11 CMV KIF11 4 MOI). In each of the vectors in which 20 MOI was used, the vector copy number was between 60 and 100 (see, bars showing vector copy number of vectors transduced at 20 MOI: (i) GFP 20 MOI, (ii) shKIF11 GFP 20 MOI, (iii) shKIF11 CMV KIF11 GFP 20 MOI, (iv) shKIF11 20 MOI, and (v) shKIF11 CMV KIF11 20 MOI).

The preferred vector copy number ranges between 1 and 10, with 5 or less typically being the target. The ideal target for the vector copy number is influenced by the functional efficiency of the vector. For example, a vector expressing a shRNA against a target, should reduce the target gene expression greater than 80% with a vector copy number of 5 or less. However, it is known that a vector copy number that is greater than 10 can cause genotoxicity. Thus, the data indicates that using 20 MOI is too high.

Example 9: Lentiviral Vector Particles Expressing the KIF11 UTR-Targeted shRNA Reduces KIF11 mRNA Levels in Mesenchymal Stem Cells (MSCs); mRNA Levels are Restored in Cells Transduced with a Lentivirus Co-Expressing Truncated KIF11 and the UTR-Targeting shRNA MSCs were passaged three times and then seeded in 6-well plates at $1 \times 10^5$ cells per well. After 24 hours, the cells were transduced with lentiviral vector particles expressing either KIF11 shRNA sequence #3 (SEQ ID NO: 3) alone or KIF11 shRNA sequence #3 (SEQ ID NO: 3) and the KIF11 coding sequence (SEQ ID NO: 4). Certain lentiviral vector particles also expressed GFP as a transduction marker. After 72 hours, RNA was extracted from the cells with the RNeasy kit (Qiagen) and converted to cDNA with SuperScript VILO (Thermo). Expression of KIF11 cDNA was determined by quantitative PCR using TaqMan probes (SEQ ID NO: 48) and primers for KIF11 (KIF11 forward primer (SEQ ID NO: 46); KIF11 reverse primer (SEQ ID NO: 47)) and actin (Actin forward primer (SEQ ID NO: 49; Actin reverse primer #1 (SEQ ID NO: 50)), and a VIC-labeled probe (SEQ ID NO: 52). KIF11 expression was normalized to actin levels for each sample.

Figure 11:
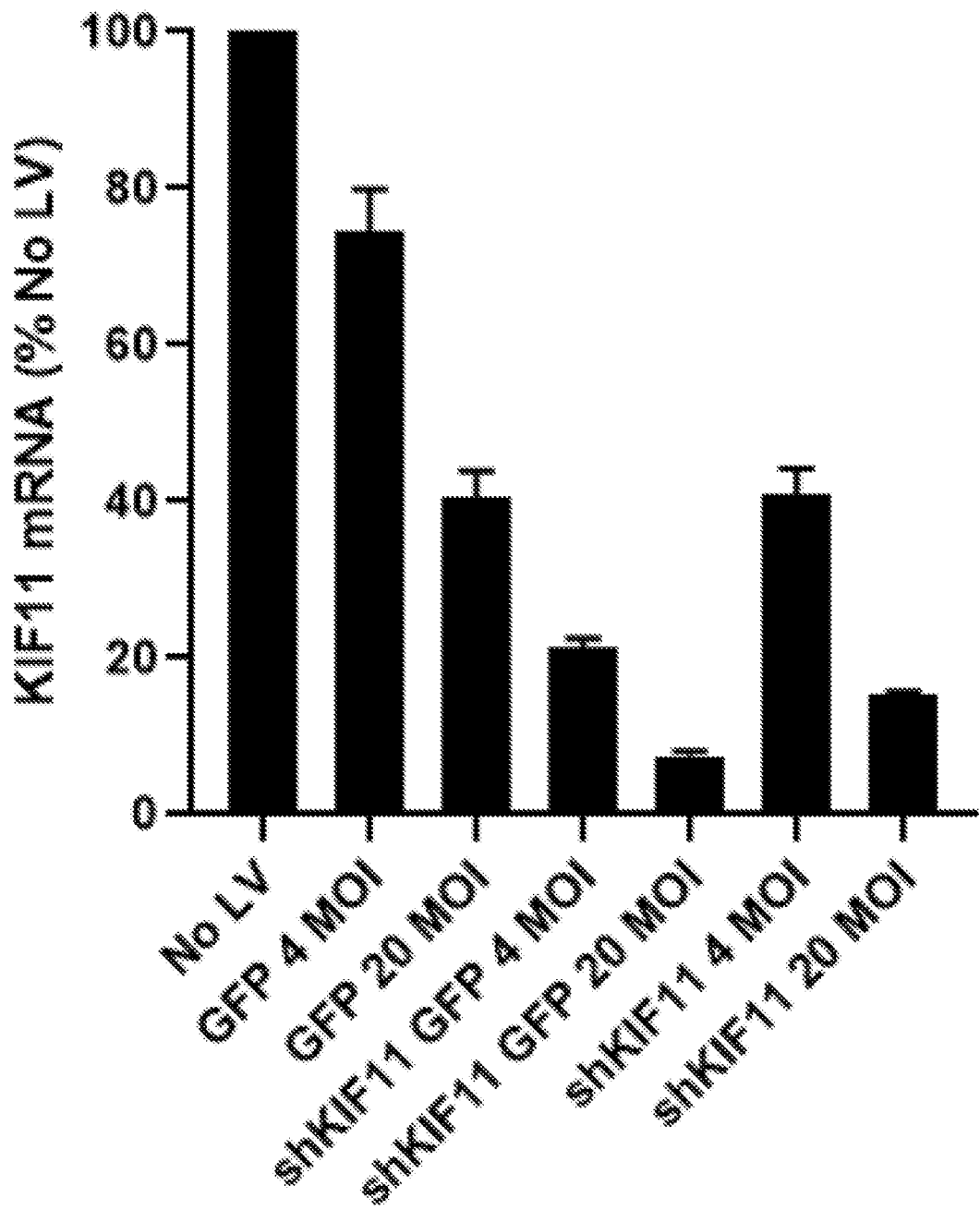
FIGS. 11A and 11B depict data showing KIF11 mRNA expression in mesenchymal stem cells after transduction with lentiviral vectors expressing: (A) a shRNA against KIF11 alone; and (B) a shRNA against KIF11 and a KIF11 coding sequence.

FIG. 11A represents KIF11 RNA expression as a percentage of non-transduced cells (NO LV). As compared to non-transduced MSCs, a vector containing the KIF11 shRNA sequence #3 (SEQ ID NO: 3) and GFP, resulted in a 79 percent decrease in KIF11 RNA and 92.5% decrease in KIF11 RNA at 4 MOI (see, bar showing data of KIF11 mRNA after transduction with shKIF11 GFP 4 MOI) and 20 MOI (see, bar showing data of KIF11 mRNA after transduction with shKIF11 GFP 20 MOI), respectively. As compared to non-transduced MSCs, vectors containing the KIF11 shRNA sequence #3 (SEQ ID NO: 3) without GFP, resulted in a 59 percent decrease in KIF11 RNA and an 85 percent decrease in KIF11 RNA at 4 MOI (see, bar showing data of KIF11 mRNA after transduction with shKIF11 4 MOI) and 20 MOI (see, bar showing data of KIF11 mRNA after transduction with shKIF11 20 MOI), respectively. Thus, in both vectors expressing KIF11 shRNA, increasing the MOI resulted in a greater decrease in KIF11 mRNA expression, regardless of whether the vector expressed GFP.

Of note, transduction with vectors that only contained GFP resulted in a reduction of KIF11 mRNA. For example, as compared to non-transduced MSCs, vectors expressing only GFP resulted in a 59 percent decrease in KIF11 mRNA when the vector was transduced at 20 MOI (see, bar showing data of KIF11 mRNA after transduction with GFP 20 MOI). It is not clear why such a decrease in KIF11 mRNA was observed. However, as revealed from the vector copy number data (see, FIG. 10), 20 MOI results in a high vector copy number. This high vector copy number could be causing toxicity and may, therefore, explain that shRNA-independent effect on KIF11 mRNA.

Figure 11B:
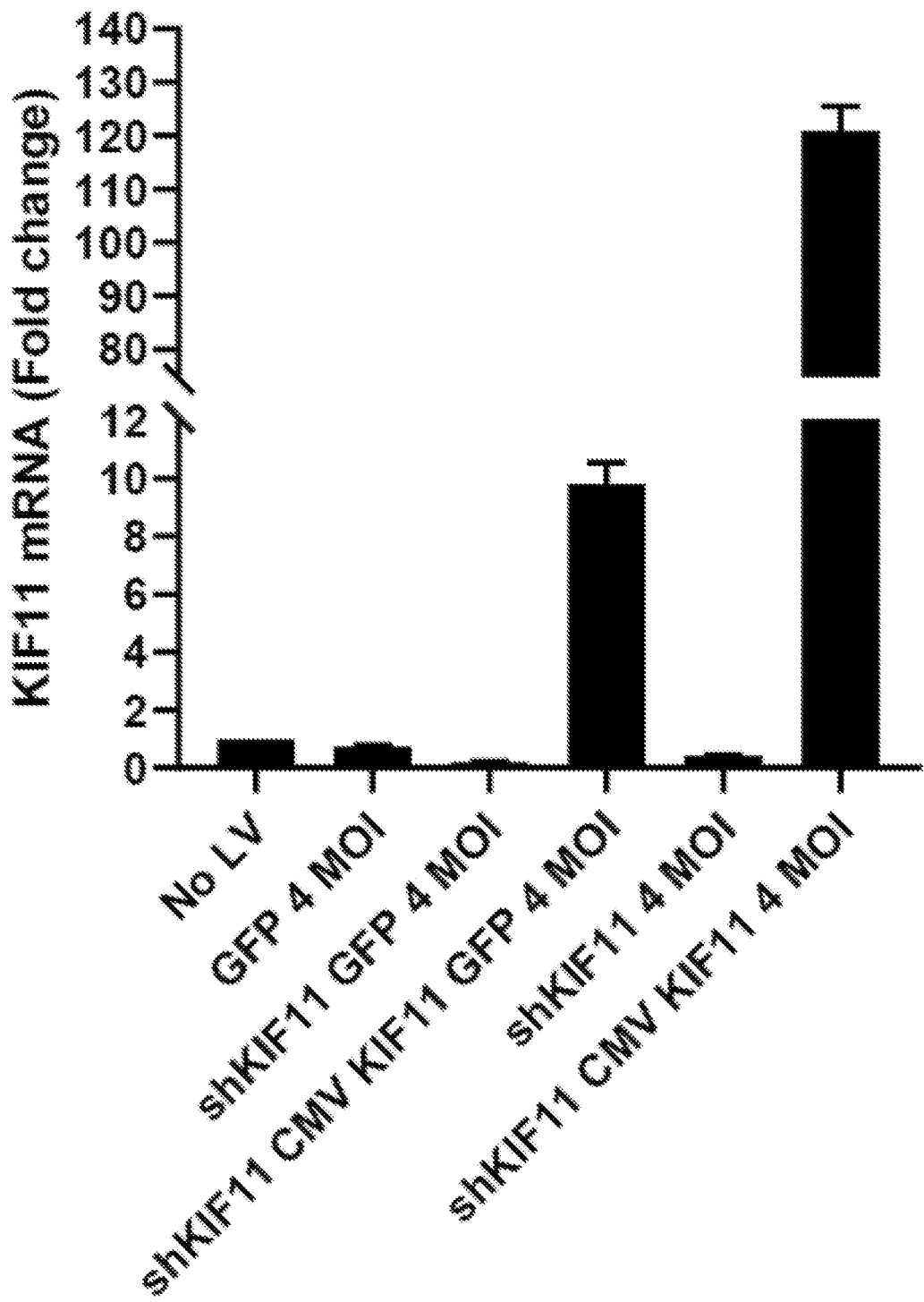

FIG. 11B represents KIF11 mRNA expression as a fold change relative to non-transduced cells (No LV). In the vector that expressed KIF11 shRNA sequence #3 (SEQ ID NO: 3), the KIF11 coding sequence (SEQ ID NO: 4), and GFP, there was a 9.8-fold increase in KIF11 mRNA and the KIF11 coding sequence (see, bar showing KIF11 mRNA after transduction with shKIF11 CMV KIF11 GFP 4 MOI). In the vector that expressed KIF11 shRNA sequence #3 (SEQ ID NO: 3), the KIF11 coding sequence (SEQ ID NO: 4), and no GFP, there was a 121-fold increase in KIF11 mRNA and the KIF11 coding sequence (see, bar showing KIF11 mRNA after transduction with shKIF11 CMV KIF11 4 MOI). This indicates that increasing the complexity of the vector (i.e. adding GFP) causes a reduction in vector-expressed KIF11.

Example 10: KIF11 UTR-Targeted shRNA does not have an Effect on the Proliferation of Mesenchymal Stem Cells (MSCs) During a Single Cell Passage MSCs were passaged three times and then seeded in 24-well plates at $2 \times 10^4$ cells per well. After 24 hours, the cells were transduced with lentiviral vector particles expressing either KIF11 shRNA sequence #3 (SEQ ID NO: 3) alone or KIF11 shRNA sequence #3 (SEQ ID NO: 3) and the KIF11 coding sequence (SEQ ID NO: 4). After six days, cell number was determined after incubation for two hours with the MTT reagent (Sigma) and detection at 570 nm with a plate reader.

Figure 12:
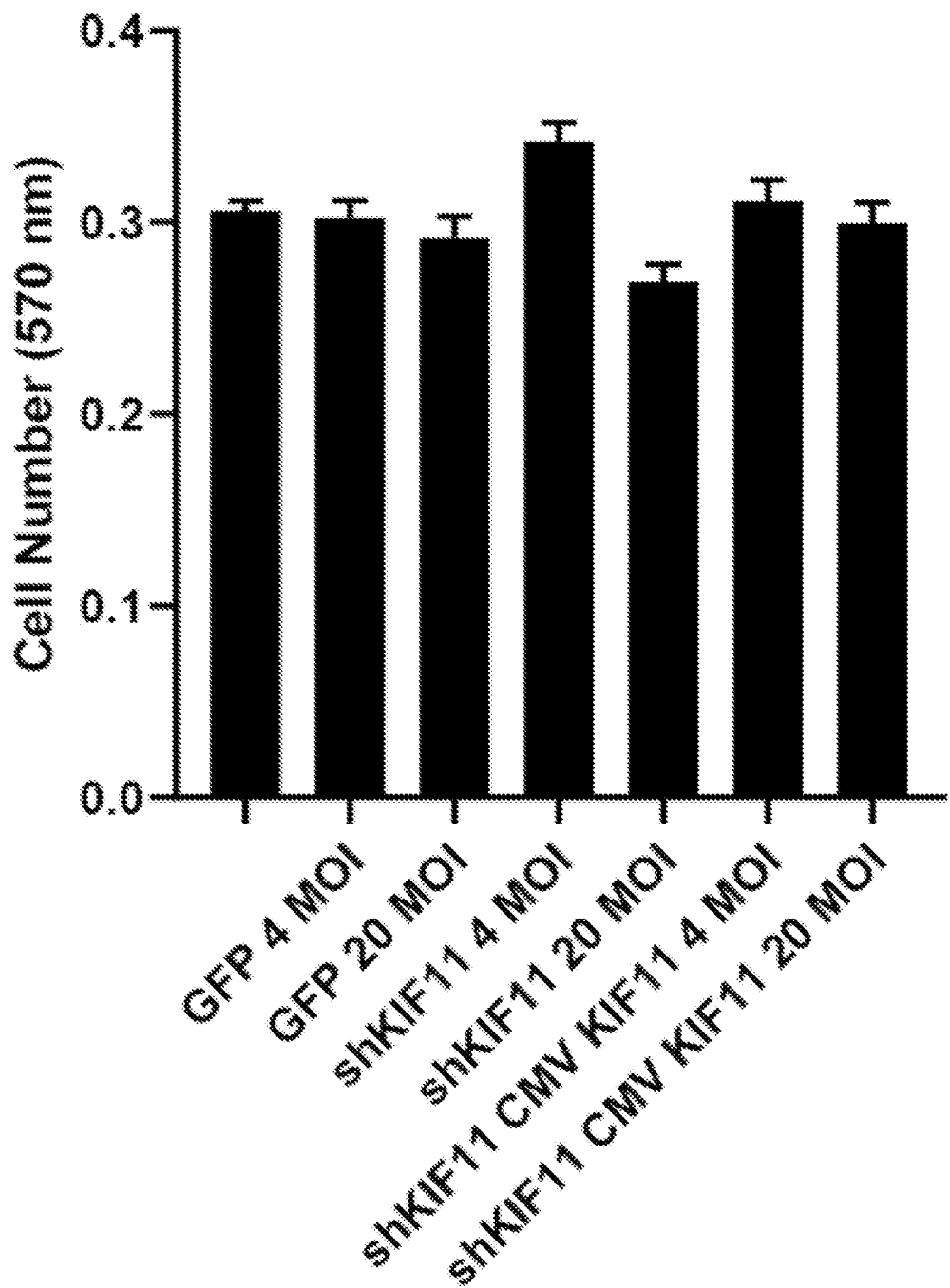
FIG. 12 depicts data showing cell number of mesenchymal stem cells after transduction with vectors expressing shRNA that targets KIF11 or vectors co-expressing shRNA that targets KIF11 and the KIF11 coding sequence.

As shown in FIG. 12, transduction with either lentiviral vector particles expressing the KIF11 shRNA sequence alone (see, bars showing cell number after transduction with shKIF11 4 MOI and shKIF11 20 MOI) or lentiviral vector particles expressing the KIF11 shRNA sequence and the KIF11 coding sequence (see, bars showing cell number after transduction with shKIF11 CMV KIF11 4 MOI and shKIF11 CMV KIF11 20 MOI) resulted in minimal change in the MSCs when compared to control treatments (see, bars showing cell number after transduction with either GFP 4 MOI and GFP 20 MOI). This data may suggest that the vector need not co-express the KIF11 coding sequence in order to maintain survival of the mesenchymal stem cells. Alternatively, expression of the KIF11 shRNA may have a negative impact on survival of the mesenchymal stem cells when trying to expand the MSCs to large, commercial scale cell volumes. Thus, large scale expansion may reveal the benefit of exogenous co-expression of KIF11 to maintain cell yield of the MSCs.

Example 11: Materials and Methods

Detailed methods of: (i) generating lentiviral vectors expression KIF11 shRNA; (ii) generating KIF11 shRNA sequences; (iii) measuring KIF11 RNA expression; (iv) measuring vector copy number; and (v) measuring cell proliferation, which were used to generate the data herein, are described below.

Generation of Lentiviral Vector Particles Expressing KIF11 shRNA

Potential RNA interference sequences were chosen from candidates selected with the shRNA design program from the Broad Institute or the BLOCK-iT™ RNAi Designer from Thermo Scientific. Short-hairpin oligonucleotide sequences containing BamHI and EcoRI restriction sites were synthesized by Eurofins Genomics. Oligonucleotide sequences were annealed by incubating at 70 degrees Celsius and then cooling to room temperature for 1 hour. In parallel, the lentiviral vectors were digested with the restriction enzymes BamHI and EcoRI for one hour at 37 degrees Celsius. The digested lentiviral vectors were purified by agarose gel electrophoresis and extracted from the gel using a DNA gel extraction kit (Thermo Scientific). The DNA concentration was determined for each and 50 ng of vector were added to 2 microliters of annealed oligo. The ligation reactions were performed with T4 DNA ligase for 30 minutes at room temperature. 2.5 microliters of the ligation mix were added to 25 microliters of Stbl3 competent bacterial cells. Transformations were done with a heat-shock step at 42 degrees Celsius. Bacterial cells were streaked onto agar plates containing ampicillin and selected colonies were expanded in LB broth. To check for insertion of the oligo sequences, plasmid DNA was extracted from harvested bacterial cultures with a DNA mini prep kit (Thermo Scientific). Insertions of the shRNA sequence in the lentiviral vector were verified by DNA sequencing using H1 primers. Lentiviral vectors containing shRNA sequences were packaged into lentiviral particles to test for their ability to knock-down KIF11 RNA.

Generating KIF11 shRNA Sequences

The sequence of *Homo sapiens* kinesin family member 11 (KIF11) (Eg5) (NM 004523.4) mRNA was used to search for potential shRNA candidates to reduce KIF11 levels in human cells. The search identified three KIF11 shRNA candidates (SEQ ID NO: 1, SEQ ID NO: 2, and SEQ ID NO: 3).

Measuring KIF11 RNA Expression

The effects of the three different KIF11 shRNA sequences on KIF11 expression were determined by measuring mRNA expression following transduction with the lentiviral vectors. PC3 cells were transduced by adding lentivirus vector at a MOI of 5 (based on 293T titer) plus 8 μg/mL of polybrene (MilliporeSigma) to cells and incubating overnight. After 24 hours, the medium was changed, and the cells were cultured for an additional 72 hours. After 72 hours, cells were lysed, and RNA was extracted using the RNeasy mini kit. cDNA was synthesized from 100 ng of RNA using the SuperScript VILO cDNA synthesis kit. PCR reactions were performed using the TaqMan Fast Advanced Master Mix and the samples were then analyzed by quantitative PCR (qPCR) using an Applied Biosystems QuantStudio3 qPCR machine (Thermo Scientific). KIF11 expression was detected using KIF11 primers/probe (KIF11 forward primer (SEQ ID NO: 46); KIF11 reverse primer (SEQ ID NO: 47); KIF11 probe (SEQ ID NO: 48)) and normalized to actin (Actin forward primer (SEQ ID NO: 49; Actin reverse primer #1 (SEQ ID NOs: 50); Actin probe (SEQ ID NO: 52). The relative expression of KIF11 was determined by its Ct value and normalized to the level of actin for each sample.

Measuring Vector Copy Number

MSCs were transduced by adding lentivirus vector plus 8 μg/mL of polybrene (MilliporeSigma) to cells and incubating overnight. After 24 hours, the medium was changed, and the cells were cultured for another 48-72 hours. Then the cells were washed with PBS 2× and the cell pellet was collected to extract genomic DNA with the DNeasy kit (Qiagen). A 50 ng/mL solution of the genomic DNA was prepared. The vector copy number was determined by performing qPCRs with primer and probe sets for a sequence encoded by the lentiviral vector, Gag (Gag forward primer (SEQ ID NO: 53); Gag reverse primer (SEQ ID NO: 54); Gag probe (SEQ ID NO: 55), and for the cellular beta actin gene (Actin forward primer (SEQ ID NO: 49); Acting reverse primer #2 (SEQ ID NO: 51); Acting probe (SEQ ID NO: 52)) on genomic DNAs from transduced cells alongside standard curve samples created using a plasmid that encodes gag and beta actin. PCR reactions were performed using the TaqMan Fast Advanced Master Mix and the samples were then analyzed by qPCR using an Applied Biosystems Quant-Studio3 qPCR machine (Thermo Scientific). The copy number of integrated lentivirus was calculated based on the Ct values as determined by qPCR. The following formula was used to measure vector copy number: Vector copy number=(Quantity mean of Gag sequence/Quantity mean of Actin sequence).

Measuring Cell Proliferation

PC3 and MSC cells were seeded in 24-well plates. After the designated culture time, the media was removed and 0.5 mL of DMEM containing 0.5 mg/mL of MTT was added to the cells. The plate was returned to an incubator at 37 degrees Celsius for 30 minutes for PC3 cells and 2 hours for MSCs. The media was removed, and 0.5 mL of isopropanol was added to the wells. The plate was placed on a rocker at a low speed for 5 minutes and the color was detected with a Bio-Tek plate reader at an absorbance of 570 nm.

Example 12: MSC Isolation, Purification, Expansion, and Characterization

Isolation, purification, and expansion: MSCs are isolated from placentas, which are recovered after elective cesarean section delivery for full-term newborns. The placenta is washed in phosphate buffered saline (PBS) and the maternal decidua is removed. Tissue portions of approximately 1 cm³ or 4 grams wet weight are dissected from the fetal interfacing chorionic villous. Tissue portions are washed again in PBS and treated at 37° C. with 1 mg/ml Collagenase A solution for 60 minutes. Digested material is collected by centrifugation and resuspended in a trypsin/EDTA solution for 10 minutes at 37° C. Trypsin-treated material is collected again by centrifugation, washed once, resuspended in Bio-AMF-1 medium (Biological Industries, Israel) with 1% penicillin-streptomycin solution plus 5 mM L-Glutamine. Cells were transferred to T-25 culture flasks and incubated in a humidified atmosphere at 37° C. with 5% $CO_2$. When MSC reach confluence in the T-25 flask, they are treated with trypsin/EDTA to release cells bound to plastic, diluted with medium and re-plated in new T-25 flasks.

For large scale manufacturing of gene modified MSCs for clinical use, a seed stock containing 10-50 million transduced MSCs are enlarged through serial passage and adapted to suspension culture. The final cell culture volume may reach 100 to 200 L, with cell yields approaching $5 \times 10^9$ per liter. Cells are recovered by centrifugation and/or filtration, washed and resuspended in medium for in vivo administration. Large scale expansion of MSCs can be performed in suspension cultures of up to 200 L under GMP conditions.

Other methods of isolating and expanding MSCs that are known in the art can be used. Detailed protocols for isolating and expanding MSCs are described in the following references, which are incorporated herein by reference in their entirety: (i) Huang Q, Yang Y, Luo C, Wen Y, Liu R, Li S, Chen T, Sun H, and Tang L. 2019. *An efficient protocol to generate placental chorionic plate-derived mesenchymal stem cells with superior proliferative and immunomodulatory properties*. Stem Cell Research & Therapy 10:301. (ii) Hassan G, Kasem I, Antaki, R, Mohammad M B, AlKadry R, and Aljamali M. 2019. *Isolation of umbilical cord mesenchymal stem cells using blood derivatives accompanied with explant method*. Stem Cell Investigation 6:29.

Characterization: The MSC phenotype varies according to tissue of origin. For chorionic villous MSCs the major phenotypic markers of cell identity include: CD44, CD73, CD105, CD90, alpha-SMA, and Stro-1. Antibody staining and flow cytometry to detect these cell surface markers will confirm the presence of MSC and further indicate the fraction of cells most similar to chorionic villous MSC. Specific patterns of gene expression have also been identified for MSCs. Chorionic villous MSCs express SOX-2 but not NANOG or POU5F1. Expression of all three of these genes is a common marker for embryonic stem cell pluripotency; expression limited to SOX-2 is consistent with the partially pluripotent phenotype of MSC.

Example 13: Lentivirus Vector Particle Genetic Modification of MSCs

Lentivirus vectors are a preferred method for stable genetic modification of MSC and have been evaluated in short-term and long-term cultures of bone marrow-derived and other types of MSC. Creating lentivirus vectors expressing both marker proteins (green or red fluorescence proteins) and puromycin acetyltransferase (confers resistance to puromycin) allow for drug selection of genetically modified MSC, which appear identical to unmodified MSC after a battery of tests for phenotypic changes, altered cell mobility, or capacity for cell amplification in long-term culture.

Lentivirus vector particle transduction can be performed in three steps:

Step 1: confluent MSCs are trypsinized, diluted 1:3 and replated for 2 days.

Step 2: Lentivirus vector stock in PBS plus 8 ug/mL Polybrene is overlayed on the MSC cell monolayer for 4 hours then removed by rinsing cells with medium.

Step 3: MSCs are detached from the plate with trypsin solution and used for DNA, RNA, or protein extraction that will measure the efficiency of transduction.

For most lentivirus vectors, transduction with multiplicity of infection equal to 5 results in >80% of MSCs becoming genetically modified. The modifications are stable and transgene expression persists for many generations.

Sequences

The following sequences are referred to herein.

| SEQ ID NO: | Description | Sequence |
|---|---|---|
| 1 | KIF11 small RNA sequence #1 | TTTGATCTGGCAACCATATTTCTCGAGAAATATGGTTGCCAGA TCAAATTTTT |
| 2 | KIF11 small RNA sequence #2 | TGCAATGTAAATACGTATTTCCTCGAGGAAATACGTATTTACA TTGCATTTTT |
| 3 | KIF11 small RNA sequence #3 | GCTTGAGCTTACATAGGTAACTCGAGTTACCTATGTAAGCTCA AGCTTTTT |
| 4 | KIF11 sequence | ATGGCGTCGCAGCCAAATTCGTCTGCGAAGAAGAAAGAGGAGA AGGGGAAGAACATCCAGGTGGTGGTGAGATGCAGACCATTTAA TTTGGCAGAGCGGAAAGCTAGCGCCCATTCAATAGTAGAATGT GATCCTGTACGAAAAGAAGTTAGTGTACGAACTGGAGGATTGG CTGACAAGAGCTCAAGGAAAACATACACTTTTGATATGGTGTT TGGAGCATCTACTAAACAGATTGATGTTTACCGAAGTGTTGTT TGTCCAATTCTGGATGAAGTTATTATGGGCTATAATTGCACTA TCTTTGCGTATGGCCAAACTGGCACTGGAAAAACTTTTACAAT GGAAGGTGAAAGGTCACCTAATGAAGAGTATACCTGGGAAGAG GATCCCTTGGCTGGTATAATTCCACGTACCCTTCATCAAATTT TTGAGAAACTTACTGATAATGGTACTGAATTTTCAGTCAAAGT GTCTCTGTTGGAGATCTATAATGAAGAGCTTTTTGATCTTCTT AATCCATCATCTGATGTTTCTGAGAGACTACAGATGTTTGATG ATCCCCGTAACAAGAGAGGAGTGATAATTAAAGGTTTAGAAGA AATTACAGTACACAACAAGGATGAAGTCTATCAAATTTTAGAA AAGGGGGCAGCAAAAAGGACAACTGCAGCTACTCTGATGAATG CATACTCTAGTCGTTCCCACTCAGTTTTCTCTGTTACAATACA |

| SEQ ID NO: | Description | Sequence |
|---|---|---|
| | | TATGAAAGAAACTACGATTGATGGAGAAGAGCTTGTTAAAATC<br>GGAAAGTTGAACTTGGTTGATCTTGCAGGAAGTGAAAACATTG<br>GCCGTTCTGGAGCTGTTGATAAGAGAGCTCGGGAAGCTGGAAA<br>TATAAATCAATCCCTGTTGACTTTGGGAAGGGTCATTACTGCC<br>CTTGTAGAAAGAACACCTCATGTTCCTTATCGAGAATCTAAAC<br>TAACTAGAATCCTCCAGGATTCTCTTGGAGGGCGTACAAGAAC<br>ATCTATAATTGCAACAATTTCTCCTGCATCTCTCAATCTTGAG<br>GAAACTCTGAGTACATTGGAATATGCTCATAGAGCAAAGAACA<br>TATTGAATAAGCCTGAAGTGAATCAGAAACTCACCAAAAAAGC<br>TCTTATTAAGGAGTATACGGAGGAGATAGAACGTTTAAAACGA<br>GATCTTGCTGCAGCCCGTGAGAAAAATGGAGTGTATATTTCTG<br>AAGAAATTTTAGAGTCATGAGTGGAAAATTAACTGTTCAAGA<br>AGAGCAGATTGTAGAATTGATTGAAAAAATTGGTGCTGTTGAG<br>GAGGAGCTGAATAGGGTTACAGAGTTGTTTATGGATAATAAAA<br>ATGAACTTGACCAGTGTAAATCTGACCTGCAAAATAAAACACA<br>AGAACTTGAAACCACTCAAAAACATTTGCAAGAAACTAAATTA<br>CAACTTGTTAAAGAAGAATATATCACATCAGCTTTGGAAAGTA<br>CTGAGGAGAAACTTCATGATGCTGCCAGCAAGCTGCTTAACAC<br>AGTTGAAGAAACTACAAAAGATGTATCTGGTCTCCATTCCAAA<br>CTGGATCGTAAGAAGGCAGTTGACCAACACAATGCAGAAGCTC<br>AGGATATTTTTGGCAAAAACCTGAATAGTCTGTTTAATAATAT<br>GGAAGAATTAATTAAGGATGGCAGCTCAAAGCAAAAGGCCATG<br>CTAGAAGTACATAAGACCTTATTTGGTAATCTGCTGTCTTCCA<br>GTGTCTCTGCATTAGATACCATTACTACAGTAGCACTTGGATC<br>TCTCACATCTATTCCAGAAATGTGTCTACTCATGTTTCTCAG<br>ATTTTTAATATGATACTAAAAGAACAATCATTAGCAGCAGAAA<br>GTAAAACTGTACTACAGGAATTGATTAATGTACTCAAGACTGA<br>TCTTCTAAGTTCACTGGAAATGATTTTATCCCCAACTGTGGTG<br>TCTATACTGAAAATCAATAGTCAACTAAAGCATATTTTCAAGA<br>CTTCATTGACAGTGGCCGATAAGATAGAAGATCAAAAAAAGGA<br>ACTAGATGGCTTTCTCAGTATACTGTGTAACAATCTACATGAA<br>CTACAAGAAAATACCATTTGTTCCTTGGTTGAGTCACAAAAGC<br>AATGTGGAAACCTAACTGAAGACCTGAAGACAATAAAGCAGAC<br>CCATTCCCAGGAACTTTGCAAGTTAATGAATCTTTGGACAGAG<br>AGATTCTGTGCTTTGGAGGAAAAGTGTGAAAATATACAGAAAC<br>CACTTAGTAGTGTCCAGGAAAATATACAGCAGAAATCTAAGGA<br>TATAGTCAACAAAATGACTTTTCACAGTCAAAAATTTTGTGCT<br>GATTCTGATGGCTTCTCACAGGAACTCAGAAATTTTAACCAAG<br>AAGGTACAAAATTGGTTGAAGAATCTGTGAAACACTCTGATAA<br>ACTCAATGGCAACCTGGAAAAAATATCTCAAGAGACTGAACAG<br>AGATGTGAATCTCTGAACACAAGAACAGTTTATTTTTCTGAAC<br>AGTGGGTATCTTCCTTAAATGAAAGGGAACAGGAACTTCACAA<br>CTTATTGGAGGTTGTAAGCCAATGTTGTGAGGCTTCAAGTTCA<br>GACATCACTGAGAAATCAGATGGACGTAAGGCAGCTCATGAGA<br>AACAGCATAACATTTTTCTTGATCAGATGACTATTGATGAAGA<br>TAAATTGATAGCACAAAATCTAGAACTTAATGAAACCATAAAA<br>ATTGGTTTGACTAAGCTTAATTGCTTTCTGGAACAGGATCTGA<br>AACTGGATATCCCAACAGGTACGACACCACAGAGGAAAAGTTA<br>TTTATACCCATCAACACTGGTAAGAACTGAACCACGTGAACAT<br>CTCCTTGATCAGCTGAAAAGGAAACAGCCTGAGCTGTTAATGA<br>TGCTAAACTGTTCAGAAAACAACAAAGAAGAGACAATTCCGGA<br>TGTGGATGTAGAAGAGGCAGTTCTGGGGCAGTATACTGAAGAA<br>CCTCTAAGTCAAGAGCCATCTGTAGATGCTGGTGTGGATTGTT<br>CATCAATTGGCGGGGTTCCATTTTTCCAGCATAAAAAATCACA<br>TGGAAAAGACAAAGAAAACAGAGGCATTAACACACTGGAGAGG<br>TCTAAAGTGGAAGAAACTACAGAGCACTTGGTTACAAAGAGCA<br>GATTACCTCTGCGAGCCCAGATCAACCTTTAA |
| 5 | Rous Sarcoma virus (RSV) promoter | GTAGTCTTATGCAATACTCTTGTAGTCTTGCAACATGGTAACG<br>ATGAGTTAGCAACATGCCTTACAAGGAGAGAAAAAGCACCGTG<br>CATGCCGATTGGTGGAAGTAAGGTGGTACGATCGTGCCTTATT<br>AGGAAGGCAACAGACGGGTCTGACATGGATTGGACGAACCACT<br>GAATTGCCGCATTGCAGAGATATTGTATTTAAGTGCCTAGCTC<br>GATACAATAAACG |
| 6 | 5' Long terminal repeat (LTR) | GGTCTCTCTGGTTAGACCAGATCTGAGCCTGGGAGCTCTCTGG<br>CTAACTAGGGAACCCACTGCTTAAGCCTCAATAAAGCTTGCCT<br>TGAGTGCTTCAAGTAGTGTGTGCCCGTCTGTTGTGTGACTCTG<br>GTAACTAGAGATCCCTCAGACCCTTTTAGTCAGTGTGGAAAAT<br>CTCTAGCA |
| 7 | Psi Packaging signal | TACGCCAAAAATTTTGACTAGCGGAGGCTAGAAGGAGAGAG |
| 8 | Rev response element (RRE) | AGGAGCTTTGTTCCTTGGGTTCTTGGGAGCAGCAGGAAGCACT<br>ATGGGCGCAGCCTCAATGACGCTGACGGTACAGGCCAGACAAT<br>TATTGTCTGGTATAGTGCAGCAGCAGAACAATTTGCTGAGGGC |

-continued

| SEQ ID NO: | Description | Sequence |
|---|---|---|
|  |  | TATTGAGGCGCAACAGCATCTGTTGCAACTCACAGTCTGGGGC<br>ATCAAGCAGCTCCAGGCAAGAATCCTGGCTGTGGAAAGATACC<br>TAAAGGATCAACAGCTCC |
| 9 | Central polypurine tract (cPPT) | TTTTAAAAGAAAAGGGGGGATTGGGGGGTACAGTGCAGGGGAA<br>AGAATAGTAGACATAATAGCAACAGACATACAAACTAAAGAAT<br>TACAAAAACAAATTACAAAATTCAAAATTTTA |
| 10 | Polymerase III shRNA promoters; H1 promoter | GAACGCTGACGTCATCAACCCGCTCCAAGGAATCGCGGGCCCA<br>GTGTCACTAGGCGGGAACACCCAGCGCGCGTGCGCCCTGGCAG<br>GAAGATGGCTGTGAGGGACAGGGGAGTGGCGCCCTGCAATATT<br>TGCATGTCGCTATGTGTTCTGGGAAATCACCATAAACGTGAAA<br>TGTCTTTGGATTTGGGAATCTTATAAGTTCTGTATGAGACCAC<br>TT |
| 11 | Long WPRE sequence | AATCAACCTCTGATTACAAAATTTGTGAAAGATTGACTGGTAT<br>TCTTAACTATGTTGCTCCTTTTACGCTATGTGGATACGCTGCT<br>TTAATGCCTTTGTATCATGCTATTGCTTCCCGTATGGCTTTCA<br>TTTTCTCCTCCTTGTATAAATCCTGGTTGCTGTCTCTTTATGA<br>GGAGTTGTGGCCCGTTGTCAGGCAACGTGGCGTGGTGTGCACT<br>GTGTTTGCTGACGCAACCCCCACTGGTTGGGGCATTGCCACCA<br>CCTGTCAGCTCCTTTCCGGGACTTTCGCTTTCCCCCTCCCTAT<br>TGCCACGGCGGAACTCATCGCCGCCTGCCTTGCCCGCTGCTGG<br>ACAGGGGCTCGGCTGTTGGGCACTGACAATTCCGTGGTGTTGT<br>CGGGGAAATCATCGTCCTTTCCTTGGCTGCTCGCCTGTGTTGC<br>CACCTGGATTCTGCGCGGGACGTCCTTCTGCTACGTCCCTTCG<br>GCCCTCAATCCAGCGGACCTTCCTTCCCGCGGCCTGCTGCCGG<br>CTCTGCGGCCTCTTCCGCGTCTTCGCCTTCGCCCTCAGACGAG<br>TCGGATCTCCCTTTGGGCCGCCTCCCCGCCT |
| 12 | 3' delta LTR | TGGAAGGGCTAATTCACTCCCAACGAAGATAAGATCTGCTTTT<br>TGCTTGTACTGGGTCTCTCTGGTTAGACCAGATCTGAGCCTGG<br>GAGCTCTCTGGCTAACTAGGGAACCCACTGCTTAAGCCTCAAT<br>AAAGCTTGCCTTGAGTGCTTCAAGTAGTGTGTGCCCGTCTGTT<br>GTGTGACTCTGGTAACTAGAGATCCCTCAGACCCTTTTAGTCA<br>GTGTGGAAAATCTCTAGCAGTAGTAGTTCATGTCA |
| 13 | Helper/Rev; Chicken beta actin (CAG) promoter; Transcription | GCTATTACCATGGGTCGAGGTGAGCCCCACGTTCTGCTTCACT<br>CTCCCCATCTCCCCCCCCTCCCCACCCCCAATTTTGTATTTAT<br>TTATTTTTTAATTATTTTGTGCAGCGATGGGGGCGGGGGGGGG<br>GGGGGCGCGCGCCAGGCGGGGCGGGGCGGGGCGAGGGGCGGGG<br>CGGGGCGAGGCGGAGAGGTGCGGCGGCAGCCAATCAGAGCGGC<br>GCGCTCCGAAAGTTTCCTTTTATGGCGAGGCGGCGGCGGCGGC<br>GGCCCTATAAAAAGCGAAGCGCGCGGCGGGCG |
| 14 | Helper/Rev; HIV Gag; Viral capsid | ATGGGTGCGAGAGCGTCAGTATTAAGCGGGGGAGAATTAGATC<br>GATGGGAAAAAATTCGGTTAAGGCCAGGGGGAAAGAAAAAATA<br>TAAATTAAAACATATAGTATGGGCAAGCAGGGAGCTAGAACGA<br>TTCGCAGTTAATCCTGGCCTGTTAGAAACATCAGAAGGCTGTA<br>GACAAATACTGGGACAGCTACAACCATCCCTTCAGACAGGATC<br>AGAAGAACTTAGATCATTATATAATACAGTAGCAACCCTCTAT<br>TGTGTGCATCAAAGGATAGAGATAAAAGACACCAAGGAAGCTT<br>TAGACAAGATAGAGGAAGAGCAAAACAAAAGTAAGAAAAAAGC<br>ACAGCAAGCAGCAGCTGACACAGGACACAGCAATCAGGTCAGC<br>CAAAATTACCCTATAGTGCAGAACATCCAGGGGCAAATGGTAC<br>ATCAGGCCATATCACCTAGAACTTTAAATGCATGGGTAAAAGT<br>AGTAGAAGAGAAGGCTTTCAGCCCAGAAGTGATACCCATGTTT<br>TCAGCATTATCAGAAGGAGCCACCCCACAAGATTTAAACACCA<br>TGCTAAACACAGTGGGGGGACATCAAGCAGCCATGCAAATGTT<br>AAAAGAGACCATCAATGAGGAAGCTGCAGAATGGGATAGAGTG<br>CATCCAGTGCATGCAGGGCCTATTGCACCAGGCCAGATGAGAG<br>AACCAAGGGGAAGTGACATAGCAGGAACTACTAGTACCCTTCA<br>GGAACAAATAGGATGGATGACACATAATCCACCTATCCCAGTA<br>GGAGAAATCTATAAAAGATGGATAATCCTGGGATTAAATAAAA<br>TAGTAAGAATGTATAGCCCTACCAGCATTCTGGACATAAGACA<br>AGGACCAAAGGAACCCTTTAGAGACTATGTAGACCGATTCTAT<br>AAAACTCTAAGAGCCGAGCAAGCTTCACAAGAGGTAAAAAATT<br>GGATGACAGAAACCTTGTTGGTCCAAAATGCGAACCCAGATTG<br>TAAGACTATTTTAAAAGCATTGGGACCAGGAGCGACACTAGAA<br>GAAATGATGACAGCATGTCAGGGAGTGGGGGGACCCGGCCATA<br>AAGCAAGAGTTTTGGCTGAAGCAATGAGCCAAGTAACAAATCC<br>AGCTACCATAATGATACAGAAAGGCAATTTTAGGAACCAAAGA<br>AAGACTGTTAAGTGTTTCAATTGTGGCAAAGAAGGGCACATAG<br>CCAAAAATTGCAGGGCCCCTAGGAAAAAGGGCTGTTGGAAATG<br>TGGAAAGGAAGGACACCAAATGAAAGATTGTACTGAGAGACAG<br>GCTAATTTTTTAGGGAAGATCTGGCCTTCCCACAAGGGAAGGC |

| SEQ ID NO: | Description | Sequence |
|---|---|---|
| | | CAGGGAATTTTCTTCAGAGCAGACCAGAGCCAACAGCCCCACC<br>AGAAGAGAGCTTCAGGTTTGGGGAAGAGACAACAACTCCCTCT<br>CAGAAGCAGGAGCCGATAGACAAGGAACTGTATCCTTTAGCTT<br>CCCTCAGATCACTCTTTGGCAGCGACCCCTCGTCACAATAA |
| 15 | Helper/Rev; HIV Pol; Protease and reverse transcriptase | ATGAATTTGCCAGGAAGATGGAAACCAAAAATGATAGGGGGAA<br>TTGGAGGTTTTATCAAAGTAGGACAGTATGATCAGATACTCAT<br>AGAAATCTGCGGACATAAAGCTATAGGTACAGTATTAGTAGGA<br>CCTACACCTGTCAACATAATTGGAAGAAATCTGTTGACTCAGA<br>TTGGCTGCACTTTAAATTTTCCCATTAGTCCTATTGAGACTGT<br>ACCAGTAAAATTAAAGCCAGGAATGGATGGCCCAAAAGTTAAA<br>CAATGGCCATTGACAGAAGAAAAAATAAAAGCATTAGTAGAAA<br>TTTGTACAGAAATGGAAAAGGAAGGAAAAATTTCAAAAATTGG<br>GCCTGAAAATCCATACAATACTCCAGTATTTGCCATAAAGAAA<br>AAAGACAGTACTAAATGGAGAAAATTAGTAGATTTCAGAGAAC<br>TTAATAAGAGAACTCAAGATTTCTGGGAAGTTCAATTAGGAAT<br>ACCACATCCTGCAGGGTTAAAACAGAAAAAATCAGTAACAGTA<br>CTGGATGTGGGCGATGCATATTTTTCAGTTCCCTTAGATAAAG<br>ACTTCAGGAAGTATACTGCATTTACCATACCTAGTATAAACAA<br>TGAGACACCAGGGATTAGATATCAGTACAATGTGCTTCCACAG<br>GGATGGAAAGGATCACCAGCAATATTCCAGTGTAGCATGACAA<br>AAATCTTAGAGCCTTTTAGAAAACAAATCCAGACATAGTCAT<br>CTATCAATACATGGATGATTTGTATGTAGGATCTGACTTAGAA<br>ATAGGGCAGCATAGAACAAAAATAGAGGAACTGAGACAACATC<br>TGTTGAGGTGGGGATTTACCACACCAGACAAAAAACATCAGAA<br>AGAACCTCCATTCCTTTGGATGGGTTATGAACTCCATCCTGAT<br>AAATGGACAGTACAGCCTATAGTGCTGCCAGAAAAGGACAGCT<br>GGACTGTCAATGACATACAGAAATTAGTGGGAAAATTGAATTG<br>GGCAAGTCAGATTTATGCAGGGATTAAAGTAAGGCAATTATGT<br>AAACTTCTTAGGGGAACCAAAGCACTAACAGAAGTAGTACCAC<br>TAACAGAAGAAGCAGAGCTAGAACTGGCAGAAAACAGGGAGAT<br>TCTAAAAGAACCGGTACATGGAGTGTATTATGACCCATCAAAA<br>GACTTAATAGCAGAAATACAGAAGCAGGGGCAAGGCCAATGGA<br>CATATCAAATTTATCAAGAGCCATTTAAAAATCTGAAAACAGG<br>AAAATATGCAAGAATGAAGGGTGCCCACACTAATGATGTGAAA<br>CAATTAACAGAGGCAGTACAAAAAATAGCCACAGAAAGCATAG<br>TAATATGGGGAAAGACTCCTAAATTTAAATTACCCATACAAAA<br>GGAAACATGGGAAGCATGGTGGACAGAGTATTGGCAAGCCACC<br>TGGATTCCTGAGTGGGAGTTTGTCAATACCCCTCCCTTAGTGA<br>AGTTATGGTACCAGTTAGAGAAAGAACCCATAATAGGAGCAGA<br>AACTTTCTATGTAGATGGGGCAGCCAATAGGGAAACTAAATTA<br>GGAAAAGCAGGATATGTAACTGACAGAGGAAGACAAAAAGTTG<br>TCCCCCTAACGGACACAACAAATCAGAAGACTGAGTTACAAGC<br>AATTCATCTAGCTTTGCAGGATTCGGGATTAGAAGTAAACATA<br>GTGACAGACTCACAATATGCATTGGGAATCATTCAAGCACAAC<br>CAGATAAGAGTGAATCAGAGTTAGTCAGTCAAATAATAGAGCA<br>GTTAATAAAAAAGGAAAAAGTCTACCTGGCATGGGTACCAGCA<br>CACAAAGGAATTGGAGGAAATGAACAAGTAGATGGGTTGGTCA<br>GTGCTGGAATCAGGAAAGTACTA |
| 16 | Helper Rev; HIV Integrase; Integration of viral RNA | TTTTTAGATGGAATAGATAAGGCCCAAGAAGAACATGAGAAAT<br>ATCACAGTAATTGGAGAGCAATGGCTAGTGATTTTAACCTACC<br>ACCTGTAGTAGCAAAAGAAATAGTAGCCAGCTGTGATAAATGT<br>CAGCTAAAAGGGGAAGCCATGCATGGACAAGTAGACTGTAGCC<br>CAGGAATATGGCAGCTAGATTGTACACATTTAGAAGGAAAAGT<br>TATCTTGGTAGCAGTTCATGTAGCCAGTGGATATATAGAAGCA<br>GAAGTAATTCCAGCAGAGACAGGGCAAGAAACAGCATACTTCC<br>TCTTAAAATTAGCAGGAAGATGGCCAGTAAAAACAGTACATAC<br>AGACAATGGCAGCAATTTCACCAGTACTACAGTTAAGGCCGCC<br>TGTTGGTGGGCGGGGATCAAGCAGGAATTTGGCATTCCCTACA<br>ATCCCCAAAGTCAAGGAGTAATAGAATCTATGAATAAAGAATT<br>AAAGAAAATTATAGGACAGGTAAGAGATCAGGCTGAACATCTT<br>AAGACAGCAGTACAAATGGCAGTATTCATCCACAATTTTAAAA<br>GAAAAGGGGGGATTGGGGGGTACAGTGCAGGGGAAAGAATAGT<br>AGACATAATAGCAACAGACATACAAACTAAAGAATTACAAAAA<br>CAAATTACAAAAATTCAAAATTTTCGGGTTTATTACAGGGACA<br>GCAGAGATCCAGTTTGGAAAGGACCAGCAAAGCTCCTCTGGAA<br>AGGTGAAGGGGCAGTAGTAATACAAGATAATAGTGACATAAAA<br>GTAGTGCCAAGAAGAAAAGCAAAGATCATCAGGGATTATGGAA<br>AACAGATGGCAGGTGATGATTGTGTGGCAAGTAGACAGGATGA<br>GGATTAA |
| 17 | Helper/Rev; HIV RRE; Binds Rev element | AGGAGCTTTGTTCCTTGGGTTCTTGGGAGCAGCAGGAAGCACT<br>ATGGGCGCAGCGTCAATGACGCTGACGGTACAGGCCAGACAAT<br>TATTGTCTGGTATAGTGCAGCAGCAGAACAATTTGCTGAGGGC<br>TATTGAGGCGCAACAGCATCTGTTGCAACTCACAGTCTGGGGC |

| SEQ ID NO: | Description | Sequence |
|---|---|---|
| | | ATCAAGCAGCTCCAGGCAAGAATCCTGGCTGTGGAAAGATACC TAAAGGATCAACAGCTCCT |
| 18 | Helper/Rev; HIV Rev; Nuclear export and stabilize viral mRNA | ATGGCAGGAAGAAGCGGAGACAGCGACGAAGAACTCCTCAAGG CAGTCAGACTCATCAAGTTTCTCTATCAAAGCAACCCACCTCC CAATCCCGAGGGGACCCGACAGGCCCGAAGGAATAGAAGAAGA AGGTGGAGAGAGAGACAGAGACAGATCCATTCGATTAGTGAAC GGATCCTTAGCACTTATCTGGGACGATCTGCGGAGCCTGTGCC TCTTCAGCTACCACCGCTTGAGAGACTTACTCTTGATTGTAAC GAGGATTGTGGAACTTCTGGGACGCAGGGGGTGGGAAGCCCTC AAATATTGGTGGAATCTCCTACAATATTGGAGTCAGGAGCTAA AGAATAG |
| 19 | Helper/Rev; CMV early (CAG) enhancer; Enhance Transcription | TAGTTATTAATAGTAATCAATTACGGGGTCATTAGTTCATAGC CCATATATGGAGTTCCGCGTTACATAACTTACGGTAAATGGCC CGCCTGGCTGACCGCCCAACGACCCCCGCCCATTGACGTCAAT AATGACGTATGTTCCCATAGTAACGCCAATAGGGACTTTCCAT TGACGTCAATGGGTGGACTATTTACGGTAAACTGCCCACTTGG CAGTACATCAAGTGTATCATATGCCAAGTACGCCCCCTATTGA CGTCAATGACGGTAAATGGCCCGCCTGGCATTATGCCCAGTAC ATGACCTTATGGGACTTTCCTACTTGGCAGTACATCTACGTAT TAGTCATC |
| 20 | Helper/Rev; Chicken beta actin intron; Enhance gene expression | GGAGTCGCTGCGTTGCCTTCGCCCCGTGCCCCGCTCCGCGCCG CCTCGCGCCGCCCGCCCCGGCTCTGACTGACCGCGTTACTCCC ACAGGTGAGCGGGCGGGACGGCCCTTCTCCTCCGGGCTGTAAT TAGCGCTTGGTTTAATGACGGCTCGTTTCTTTTCTGTGGCTGC GTGAAAGCCTTAAAGGGCTCCGGGAGGGCCCTTTGTGCGGGGG GGAGCGGCTCGGGGGGTGCGTGCGTGTGTGTGCGTGGGGAG CGCCGCGTGCGGCCCGCGCTGCCCGGCGGCTGTGAGCGCTGCG GGCGCGGCGCGGGGCTTTGTGCGCTCCGCGTGTGCGCGAGGGG AGCGCGGCCGGGGGCGGTGCCCCGCGGTGCGGGGGGGCTGCGA GGGGAACAAAGGCTGCGTGCGGGGTGTGTGCGTGGGGGGGTGA GCAGGGGGTGTGGGCGCGGCGGTCGGGCTGTAACCCCCCCCTG CACCCCCCTCCCCGAGTTGCTGAGCACGGCCCCGGCTTCGGGTG CGGGGCTCCGTGCGGGGCGTGGCGCGGGGCTCGCCGTGCCGGG CGGGGGGTGGCGGCAGGTGGGGGTGCCGGGCGGGGCGGGGCCG CCTCGGGCCGGGGAGGGCTCGGGGAGGGGCGCGGCGGCCCCG GAGCGCCGGCGGCTGTCGAGGCGCGGCGAGCCGCGCAGCCATTGC CTTTTATGGTAATCGTGCGAGAGGGCGCAGGGACTTCCTTTGT CCCAAATCTGGCGGAGCCGAAATCTGGGAGGCGCCGCCGCACC CCCTCTAGCGGGCGCGGGCGAAGCGGTGCGGCGCCGGCAGGAA GGAAATGGGCGGGGAGGGCCTTCGTGCGTCGCCGCGCCGCCGT CCCCTTCTCCATCTCCAGCCTCGGGGCTGCCGCAGGGGACGG CTGCCTTCGGGGGGACGGGGCAGGGCGGGGTTCGGCTTCTGG CGTGTGACCGGCGG |
| 21 | Helper/Rev; Rabbit beta globin poly A; RNA stability | AGATCTTTTTCCCTCTGCCAAAAATTATGGGGACATCATGAAG CCCCTTGAGCATCTGACTTCTGGCTAATAAAGGAAATTTATTT TCATTGCAATAGTGTGTTGGAATTTTTTGTGTCTCTCACTCGG AAGGACATATGGGAGGGCAAATCATTTAAAACATCAGAATGAG TATTTGGTTTAGAGTTTGGCAACATATGCCATATGCTGGCTGC CATGAACAAAGGTGGCTATAAAGAGGTCATCAGTATATGAAAC AGCCCCCTGCTGTCCATTCCTTATTCCATAGAAAAGCCTTGAC TTGAGGTTAGATTTTTTTTATATTTTGTTTTGTGTTATTTTTT TCTTTAACATCCCTAAAATTTTCCTTACATGTTTTACTAGCCA GATTTTTCCTCCTCCTGACTACTCCCAGTCATAGCTGTCCC TCTTCTCTTATGAAGATC |
| 22 | Envelope; CMV promoter; Transcription | ACATTGATTATTGACTAGTTATTAATAGTAATCAATTACGGGG TCATTAGTTCATAGCCCATATATGGAGTTCCGCGTTACATAAC TTACGGTAAATGGCCCGCCTGGCTGACCGCCCAACGACCCCCG CCCATTGACGTCAATAATGACGTATGTTCCCATAGTAACGCCA ATAGGGACTTTCCATTGACGTCAATGGGTGGAGTATTTACGGT AAACTGCCCACTTGGCAGTACATCAAGTGTATCATATGCCAAG TACGCCCCCTATTGACGTCAATGACGGTAAATGGCCCGCCTGG CATTATGCCCAGTACATGACCTTATGGGACTTTCCTACTTGGC AGTACATCTACGTATTAGTCATCGCTATTACCATGGTGATGCG GTTTTGGCAGTACATCAATGGGCGTGGATAGCGGTTTGACTCA CGGGGATTTCCAAGTCTCCACCCCATTGACGTCAATGGGAGTT TGTTTTGGCACCAAAATCAACGGGACTTTCCAAAATGTCGTAA CAACTCCGCCCCATTGACGCAAATGGGCGGTAGGCGTGTACGG TGGGAGGTCTATATAAGC |
| 23 | Envelope; Beta globin intron; | GTGAGTTTGGGGACCCTTGATTGTTCTTTCTTTTTCGCTATTG TAAAATTCATGTTATATGGAGGGGGCAAAGTTTTCAGGGTGTT |

| SEQ ID NO: | Description | Sequence |
|---|---|---|
|  | Enhance gene expression | GTTTAGAATGGGAAGATGTCCCTTGTATCACCATGGACCCTCA<br>TGATAATTTTGTTTCTTTCACTTTCTACTCTGTTGACAACCAT<br>TGTCTCCTCTTATTTTCTTTTCATTTTCTGTAACTTTTTCGTT<br>AAACTTTAGCTTGCATTTGTAACGAATTTTTAAATTCACTTTT<br>GTTTATTTGTCAGATTGTAAGTACTTTCTCTAATCACTTTTTT<br>TTCAAGGCAATCAGGGTATATTATATTGTACTTCAGCACAGTT<br>TTAGAGAACAATTGTTATAATTAAATGATAAGGTAGAATATTT<br>CTGCATATAAATTCTGGCTGGCGTGGAAATATTCTTATTGGTA<br>GAAACAACTACACCCTGGTCATCATCCTGCCTTTCTCTTTATG<br>GTTACAATGATATACACTGTTTGAGATGAGGATAAAATACTCT<br>GAGTCCAAACCGGGCCCCTCTGCTAACCATGTTCATGCCTTCT<br>TCTCTTTCCTACAG |
| 24 | DNA fragment containing VSV-G | GAATTCATGAAGTGCCTTTTGTACTTAGCCTTTTTATTCATTG<br>GGGTGAATTGCAAGTTCACCATAGTTTTTCCACACAACCAAAA<br>AGGAAACTGGAAAAATGTTCCTTCTAATTACCATTATTGCCCG<br>TCAAGCTCAGATTTAAATTGGCATAATGACTTAATAGGCACAG<br>CCTTACAAGTCAAAATGCCCAAGAGTCACAAGGCTATTCAAGC<br>AGACGGTTGGATGTGTCATGCTTCCAAATGGGTCACTACTTGT<br>GATTTCCGCTGGTATGGACCGAAGTATATAACACATTCCATCC<br>GATCCTTCACTCCATCTGTAGAACAATGCAAGGAAAGCATTGA<br>ACAAACGAAACAAGGAACTTGGCTGAATCCAGGCTTCCCTCCT<br>CAAAGTTGTGGATATGCAACTGTGACGGATGCCGAAGCAGTGA<br>TTGTCCAGGTGACTCCTCACCATGTGCTGGTTGATGAATACAC<br>AGGAGAATGGGTTGATTCACAGTTCATCAACGGAAATGCAGC<br>AATTACATATGCCCCACTGTCCATAACTCTACAACCTGGCATT<br>CTGACTATAAGGTCAAAGGGCTATGTGATTCTAACCTCATTTC<br>CATGGACATCACCTTCTTCTCAGAGGACGGAGAGCTATCATCC<br>CTGGGAAAGGAGGGCACAGGGTTCAGAAGTAACTACTTTGCTT<br>ATGAAACTGGAGGCAAGGCCTGCAAAATGCAATACTGCAAGCA<br>TTGGGGAGTCAGACTCCCATCAGGTGTCTGGTTCGAGATGGCT<br>GATAAGGATCTCTTTGCTGCAGCCAGATTCCCTGAATGCCCAG<br>AAGGGTCAAGTATCTCTGCTCCATCTCAGACCTCAGTGGATGT<br>AAGTCTAATTCAGGACGTTGAGAGGATCTTGGATTATTCCCTC<br>TGCCAAGAAACCTGGAGCAAAATCAGAGCGGGTCTTCAATCT<br>CTCCAGTGGATCTCAGCTATCTTGCTCCTAAAAACCCAGGAAC<br>CGGTCCTGCTTTCACCATAATCAATGGTACCCTAAAATACTTT<br>GAGACCAGATACATCAGAGTCGATATTGCTGCTCCAATCCTCT<br>CAAGAATGGTCGGAATGATCAGTGGAACTACCACAGAAAGGGA<br>ACTGTGGGATGACTGGGCACCATATGAAGACGTGGAAATTGGA<br>CCCAATGGAGTTCTGAGGACCAGTTCAGGATATAAGTTTCCTT<br>TATACATGATTGGACATGGTATGTTGGACTCCGATCTTCATCT<br>TAGCTCAAAGGCTCAGGTGTTCGAACATCCTCACATTCAAGAC<br>GCTGCTTCGCAACTTCCTGATGATGAGAGTTTATTTTTTGGTG<br>ATACTGGGCTATCCAAAAATCCAATCGAGCTTGTAGAAGGTTG<br>GTTCAGTAGTTGGAAAAGCTCTATTGCCTCTTTTTTCTTTATC<br>ATAGGGTTAATCATTGGACTATTCTTGGTTCTCCGAGTTGGTA<br>TCCATCTTTGCATTAAATTAAAGCACACCAAGAAAAGACAGAT<br>TTATACAGACATAGAGATGAGAATTC |
| 25 | Envelope; Rabbit beta globin poly A; RNA stability | AGATCTTTTTCCCTCTGCCAAAAATTATGGGGACATCATGAAG<br>CCCCTTGAGCATCTGACTTCTGGCTAATAAAGGAAATTTATTT<br>TCATTGCAATAGTGTGTTGGAATTTTTTGTGTCTCTCACTCGG<br>AAGGACATATGGGAGGGCAAATCATTTAAAACATCAGAATGAG<br>TATTTGGTTTAGAGTTTGGCAACATATGCCCATATGCTGGCTG<br>CCATGAACAAAGGTTGGCTATAAAGAGGTCATCAGTATATGAA<br>ACAGCCCCCTGCTGTCCATTCCTTATTCCATAGAAAAGCCTTG<br>ACTTGAGGTTAGATTTTTTTATATTTTGTTTTGTGTTATTTT<br>TTTCTTTAACATCCCTAAAATTTTCCTTACATGTTTTACTAGC<br>CAGATTTTTCCTCCTCTCCTGACTACTCCCAGTCATAGCTGTC<br>CCTCTTCTCTTATGGAGATC |
| 26 | Gag, Pol, Integrase fragment | GAATTCATGAATTTGCCAGGAAGATGGAAACCAAAAATGATAG<br>GGGGAATTGGAGGTTTTATCAAAGTAAGACAGTATGATCAGAT<br>ACTCATAGAAATCTGCGGACATAAAGCTATAGGTACAGTATTA<br>GTAGGACCTACACCTGTCAACATAATTGGAAGAAATCTGTTGA<br>CTCAGATTGGCTGCACTTTAAATTTTCCCATTAGTCCTATTGA<br>GACTGTACCAGTAAAATTAAAGCCAGGAATGGATGGCCCAAAA<br>GTTAAACAATGGCCATTGACAGAAGAAAAAATAAAAGCATTAG<br>TAGAAATTTGTACAGAAATGGAAAAGGAAGGAAAAATTTCAAA<br>AATTGGGCCTGAAAATCCATACAATACTCCAGTATTTGCCATA<br>AAGAAAAAGACAGTACTAAATGGAGAAAATTAGTAGATTTCA<br>GAGAACTTAATAAGAGAACTCAAGATTTCTGGGAAGTTCAATT<br>AGGAATACCACATCCTGCAGGGTTAAAACAGAAAAAATCAGTA<br>ACAGTACTGGATGTGGGCGATGCATATTTTTCAGTTCCCTTAG<br>ATAAAGACTTCAGGAAGTATACTGCATTTACCATACCTAGTAT |

| SEQ ID NO: | Description | Sequence |
|---|---|---|
| | | AAACAATGAGACACCAGGGATTAGATATCAGTACAATGTGCTT |
| | | CCACAGGGATGGAAAGGATCACCAGCAATATTCCAGTGTAGCA |
| | | TGACAAAAATCTTAGAGCCTTTTAGAAAACAAAATCCAGACAT |
| | | AGTCATCTATCAATACATGGATGATTTGTATGTAGGATCTGAC |
| | | TTAGAAATAGGGCAGCATAGAACAAAAATAGAGGAACTGAGAC |
| | | AACATCTGTTGAGGTGGGGATTTACCACACCAGACAAAAAACA |
| | | TCAGAAAGAACCTCCATTCCTTTGGATGGGTTATGAACTCCAT |
| | | CCTGATAAATGGACAGTACAGCCTATAGTGCTGCCAGAAAAGG |
| | | ACAGCTGGACTGTCAATGACATACAGAAATTAGTGGGAAAATT |
| | | GAATTGGGCAAGTCAGATTTATGCAGGGATTAAAGTAAGGCAA |
| | | TTATGTAAACTTCTTAGGGGAACCAAAGCACTAACAGAAGTAG |
| | | TACCACTAACAGAAGAAGCAGAGCTAGAACTGGCAGAAAACAG |
| | | GGAGATTCTAAAAGAACCGGTACATGGAGTGTATTATGACCCA |
| | | TCAAAAGACTTAATAGCAGAAATACAGAAGCAGGGGCAAGGCC |
| | | AATGGACATATCAAATTTATCAAGAGCCATTTAAAAATCTGAA |
| | | AACAGGAAAGTATGCAAGAATGAAGGGTGCCCACACTAATGAT |
| | | GTGAAACAATTAACAGAGGCAGTACAAAAAATAGCCACAGAAA |
| | | GCATAGTAATATGGGGAAAGACTCCTAAATTTAAATTACCCAT |
| | | ACAAAAGGAAACATGGGAAGCATGGTGGACAGAGTATTGGCAA |
| | | GCCACCTGGATTCCTGAGTGGGAGTTTGTCAATACCCCTCCCT |
| | | TAGTGAAGTTATGGTACCAGTTAGAGAAAGAACCCATAATAGG |
| | | AGCAGAAACTTTCTATGTAGATGGGGCAGCCAATAGGGAAACT |
| | | AAATTAGGAAAAGCAGGATATGTAACTGACAGAGGAAGACAAA |
| | | AAGTTGTCCCCCTAACGGACACAACAAATCAGAAGACTGAGTT |
| | | ACAAGCAATTCATCTAGCTTTGCAGGATTCGGGATTAGAAGTA |
| | | AACATAGTGACAGACTCACAATATGCATTGGGAATCATTCAAG |
| | | CACAACCAGATAAGAGTGAATCAGAGTTAGTCAGTCAAATAAT |
| | | AGAGCAGTTAATAAAAAAGGAAAAAGTCTACCTGGCATGGGTA |
| | | CCAGCACACAAAGGAATTGGAGGAAATGAACAAGTAGATAAAT |
| | | TGGTCAGTGCTGGAATCAGGAAAGTACTATTTTTAGATGGAAT |
| | | AGATAAGGCCCAAGAAGAACATGAGAAATATCACAGTAATTGG |
| | | AGAGCAATGGCTAGTGATTTTAACCTACCACCTGTAGTAGCAA |
| | | AAGAAATAGTAGCCAGCTGTGATAAATGTCAGCTAAAAGGGGA |
| | | AGCCATGCATGGACAAGTAGACTGTAGCCCAGGAATATGGCAG |
| | | CTAGATTGTACACATTTAGAAGGAAAAGTTATCTTGGTAGCAG |
| | | TTCATGTAGCCAGTGGATATATAGAAGCAGAAGTAATTCCAGC |
| | | AGAGACAGGGCAAGAAACAGCATACTTCCTCTTAAAATTAGCA |
| | | GGAAGATGGCCAGTAAAAACAGTACATACAGACAATGGCAGCA |
| | | ATTTCACCAGTACTACAGTTAAGGCCGCCTGTTGGTGGGCGGG |
| | | GATCAAGCAGGAATTTGGCATTCCCTACAATCCCCAAAGTCAA |
| | | GGAGTAATAGAATCTATGAATAAAGAATTAAAGAAAATTATAG |
| | | GACAGGTAAGAGATCAGGCTGAACATCTTAAGACAGCAGTACA |
| | | AATGGCAGTATTCATCCACAATTTTAAAAGAAAAGGGGGGATT |
| | | GGGGGGTACAGTGCAGGGGAAAGAATAGTAGACATAATAGCAA |
| | | CAGACATACAAACTAAAGAATTACAAAAACAAATTACAAAAAT |
| | | TCAAAATTTTCGGGTTTATTACAGGGACAGCAGAGATCCAGTT |
| | | TGGAAAGGACCAGCAAAGCTCCTCTGGAAAGGTGAAGGGGCAG |
| | | TAGTAATACAAGATAATAGTGACATAAAAGTAGTGCCAAGAAG |
| | | AAAAGCAAAGATCATCAGGGATTATGGAAAACAGATGGCAGGT |
| | | GATGATTGTGTGGCAAGTAGACAGGATGAGGATTAA |
| 27 | DNA Fragment containing Rev, RRE and rabbit beta globin poly A | TCTAGAATGGCAGGAAGAAGCGGAGACAGCGACGAAGAGCTCA |
| | | TCAGAACAGTCAGACTCATCAAGCTTCTCTATCAAAGCAACCC |
| | | ACCTCCCAATCCCGAGGGGACCCGACAGGCCCGAAGGAATAGA |
| | | AGAAGAAGGTGGAGAGAGAGACAGAGACAGATCCATTCGATTA |
| | | GTGAACGGATCCTTGGCACTTATCTGGGACGATCTGCGGAGCC |
| | | TGTGCCTCTTCAGCTACCACCGCTTGAGAGACTTACTCTTGAT |
| | | TGTAACGAGGATTGTGGAACTTCTGGGACGCAGGGGGTGGGAA |
| | | GCCCTCAAATATTGGTGGAATCTCCTACAATATTGGAGTCAGG |
| | | AGCTAAAGAATAGAGGGAGCTTTGTTCCTTGGGTTCTTGGGAGC |
| | | AGCAGGAAGCACTATGGGCGCAGCGTCAATGACGCTGACGGTA |
| | | CAGGCCAGACAATTATTGTCTGGTATAGTGCAGCAGCAGAACA |
| | | ATTTGCTGAGGGCTATTGAGGCGCAACAGCATCTGTTGCAACT |
| | | CACAGTCTGGGGCATCAAGCAGCTCCAGGCAAGAATCCTGGCT |
| | | GTGGAAAGATACCTAAAGGATCAACAGCTCCTAGATCTTTTTC |
| | | CCTCTGCCAAAAATTATGGGGACATCATGAAGCCCCTTGAGCA |
| | | TCTGACTTCTGGCTAATAAAGGAAATTTATTTTCATTGCAATA |
| | | GTGTGTTGGAATTTTTTGTGTCTCTCACTCGGAAGGACATATG |
| | | GGAGGGCAAATCATTTAAAACATCAGAATGAGTATTTGGTTTA |
| | | GAGTTTGGCAACATATGCCATATGCTGGCTGCCATGAACAAAG |
| | | GTGGCTATAAAGAGGTCATCAGTATATGAAACAGCCCCCTGCT |
| | | GTCCATTCCTTATTCCATAGAAAAGCCTTGACTTGAGGTTAGA |
| | | TTTTTTTTATATTTTGTTTTGTGTTATTTTTTCTTTAACATC |
| | | CCTAAAATTTTCCTTACATGTTTTACTAGCCAGATTTTTCCTC |
| | | CTCTCCTGACTACTCCCAGTCATAGCTGTCCCTCTTCTCTTAT |
| | | GAAGATCCCTCGACCTGCAGCCCAAGCTTGGCGTAATCATGGT |

-continued

| SEQ ID NO: | Description | Sequence |
|---|---|---|
|  |  | CATAGCTGTTTCCTGTGTGAAATTGTTATCCGCTCACAATTCC ACACAACATACGAGCCGGAAGCATAAAGTGTAAAGCCTGGGGT GCCTAATGAGTGAGCTAACTCACATTAATTGCGTTGCGCTCAC TGCCCGCTTTCCAGTCGGGAAACCTGTCGTGCCAGCGGATCCG CATCTCAATTAGTCAGCAACCATAGTCCCGCCCCTAACTCCGC CCATCCCGCCCCTAACTCCGCCCAGTTCCGCCCATTCTCCGCC CCATGGCTGACTAATTTTTTTTATTTATGCAGAGGCCGAGGCC GCCTCGGCCTCTGAGCTATTCCAGAAGTAGTGAGGAGGCTTTT TTGGAGGCCTAGGCTTTTGCAAAAAGCTAACTTGTTTATTGCA GCTTATAATGGTTACAAATAAAGCAATAGCATCACAAATTTCA CAAATAAAGCATTTTTTTCACTGCATTCTAGTTGTGGTTTGTC CAAACTCATCAATGTATCTTATCAGCGGCCGCCCCGGG |
| 28 | DNA fragment containing the CAG enhancer/promoter/ intron sequence | ACGCGTTAGTTATTAATAGTAATCAATTACGGGGTCATTAGTT CATAGCCCATATATGGAGTTCCGCGTTACATAACTTACGGTAA ATGGCCCGCCTGGCTGACCGCCCAACGACCCCCGCCCATTGAC GTCAATAATGACGTATGTTCCCATAGTAACGCCAATAGGGACT TTCCATTGACGTCAATGGGTGGACTATTTACGGTAAACTGCCC ACTTGGCAGTACATCAAGTGTATCATATGCCAAGTACGCCCCC TATTGACGTCAATGACGGTAAATGGCCCGCCTGGCATTATGCC CAGTACATGACCTTATGGGACTTTCCTACTTGGCAGTACATCT ACGTATTAGTCATCGCTATTACCATGGGTCGAGGTGAGCCCCA CGTTCTGCTTCACTCTCCCCATCTCCCCCCCCTCCCCACCCCC AATTTTGTATTTATTTATTTTTTAATTATTTTGTGCAGCGATG GGGGCGGGGGGGGGGGGGCGCGCGCCAGGCGGGGCGGGGCGG GGCGAGGGGCGGGGCGGGGCGAGGCGGAGAGGTGCGGCGGCAG CCAATCAGAGCGGCGCGCTCCGAAAGTTTCCTTTTATGGCGAG GCGGCGGCGGCGGCGGCCCTATAAAAAGCGAAGCGCGCGGCGG GCGGGAGTCGCTGCGTTGCCTTCGCCCCGTGCCCCGCTCCGCG CCGCCTCGCGCCGCCCGCCCCGGCTCTGACTGACCGCGTTACT CCCACAGGTGAGCGGGCGGGACGGCCCTTCTCCTCCGGGCTGT AATTAGCGCTTGGTTTAATGACGGCTCGTTTCTTTTCTGTGGC TGCGTGAAAGCCTTAAAGGGCTCCGGGAGGGCCCTTTGTGCGG GGGGAGCGGCTCGGGGGTGCGTGCGTGTGTGTGCGTGGG GAGCGCCGCGTGCGGCCCGCGCTGCCCGGCGGCTGTGAGCGCT GCGGGCGCGGCGCGGGCTTTGTGCGCTCCGCGTGTGCGCGAG GGGAGCGCGGCCGGGGCGGTGCCCCGCGGTCGGGGGGCTG CGAGGGGAACAAAGGCTGCGTGCGGGGTGTGTGCGTGGGGGGG TGAGCAGGGGGTGTGGGCGCGGCGGTCGGGCTGTAACCCCCCC CTGCACCCCCCTCCCCGAGTTGCTGAGCACGGCCCGGCTTCGG GTGCGGGGCTCCGTGCGGGGCGTGGCGCGGGGCTCGCCGTGCC GGGCGGGGGTGGCGGCAGGTGGGGGTGCCGGGCGGGGCGGGG CCGCCTCGGGCCGGGGAGGGCTCGGGGAGGGGCGCGCGGCC CCGGAGCGCCGGCGGCTGTCGAGGCGCGGCGAGCCGCAGCCAT TGCCTTTTATGGTAATCGTGCGAGAGGGCGCAGGGACTTCCTT TGTCCCAAATCTGGCGGAGCCGAAATCTGGGAGGCGCCGCCGC ACCCCCTCTAGCGGGCGCGGGCGAAGCGGTGCGGCGCCGGCAG GAAGGAAATGGGCGGGGAGGGCCTTCGTGCGTCGCCGCGCCGC CGTCCCCTTCTCCATCTCCAGCCTCGGGGCTGCCGCAGGGGGA CGGCTGCCTTCGGGGGGACGGGCAGGGCGGGGTTCGGCTTC TGGCGTGTGACCGGCGGGAATTC |
| 29 | RSV promoter and HIV Rev | CAATTGCGATGTACGGGCCAGATATACGCGTATCTGAGGGGAC TAGGGTGTGTTTAGGCGAAAAGCGGGGCTTCGGTTGTACGCGG TTAGGAGTCCCCTCAGGATATAGTAGTTTCGCTTTTGCATAGG GAGGGGGAAATGTAGTCTTATGCAATACACTTGTAGTCTTGCA ACATGGTAACGATGAGTTAGCAACATGCCTTACAAGGAGAGAA AAAGCACCGTGCATGCCGATTGGTGGAAGTAAGGTGGTACGAT CGTGCCTTATTAGGAAGGCAACAGACAGGTCTGACATGGATTG GACGAACCACTGAATTCCGCATTGCAGAGATAATTGTATTTAA GTGCCTAGCTCGATACAATAAACGCCATTTGACCATTCACCAC ATTGGTGTGCACCTCCAAGCTCGAGCTCGTTTAGTGAACCGTC AGATCGCTGGAGACGCCATCCACGCTGTTTTGACCTCCATAG AAGACACCGGGACCGATCCAGCCTCCCCTCGAAGCTAGCGATT AGGCATCTCCTATGGCAGGAAGAAGCGGAGACAGCGACGAAGA ACTCCTCAAGGCAGTCAGACTCATCAAGTTTCTCTATCAAAGC AACCCACCTCCCAATCCCGAGGGGACCCGACAGGCCCGAAGGA ATAGAAGAAGAAGGTGGAGAGAGAGACAGAGACAGATCCATTC GATTAGTGAACGGATCCTTAGCACTTATCTGGGACGATCTGCG GAGCCTGTGCCTCTTCAGCTACCACCGCTTGAGAGACTTACTC TTGATTGTAACGAGGATTGTGGAACTTCTGGGACGCAGGGGGT GGGAAGCCCTCAAATATTGGTGGAATCTCCTACAATATTGGAG TCAGGAGCTAAAGAATAGTCTAGA |
| 30 | RRE/rabbit poly A beta globin | TCTAGAAGGAGCTTTGTTCCTTGGGTTCTTGGGAGCAGCAGGA AGCACTATGGGCGCAGCGTCAATGACGCTGACGGTACAGGCCA |

| SEQ ID NO: | Description | Sequence |
|---|---|---|
| | | GACAATTATTGTCTGGTATAGTGCAGCAGCAGAACAATTTGCT GAGGGCTATTGAGGCGCAACAGCATCTGTTGCAACTCACAGTC TGGGGCATCAAGCAGCTCCAGGCAAGAATCCTGGCTGTGGAAA GATACCTAAAGGATCAACAGCTCCTAGATCTTTTTCCCTCTGC CAAAAATTATGGGGACATCATGAAGCCCCTTGAGCATCTGACT TCTGGCTAATAAAGGAAATTTATTTTCATTGCAATAGTGTGTT GGAATTTTTTGTGTCTCTCACTCGGAAGGACATATGGGAGGGC AAATCATTTAAAACATCAGAATGAGTATTTGGTTTAGAGTTTG GCAACATATGCCATATGCTGGCTGCCATGAACAAAGGTGGCTA TAAAGAGGTCATCAGTATATGAAACAGCCCCCTGCTGTCCATT CCTTATTCCATAGAAAAGCCTTGACTTGAGGTTAGATTTTTTT TATATTTTGTTTTGTGTTATTTTTTCTTTAACATCCCTAAAA TTTTCCTTACATGTTTTACTAGCCAGATTTTTCCTCCTCTCCT GACTACTCCCAGTCATAGCTGTCCCTCTTCTCTTATGAAGATC CCTCGACCTGCAGCCCAAGCTTGGCGTAATCATGGTCATAGCT GTTTCCTGTGTGAAATTGTTATCCGCTCACAATTCCACACAAC ATACGAGCCGGAAGCATAAAGTGTAAAGCCTGGGGTGCCTAAT GAGTGAGCTAACTCACATTAATTGCGTTGCGCTCACTGCCCGC TTTCCAGTCGGGAAACCTGTCGTGCCAGCGGATCCGCATCTCA ATTAGTCAGCAACCATAGTCCCGCCCCTAACTCCGCCCATCCC GCCCCTAACTCCGCCCAGTTCCGCCCATTCTCCGCCCCATGGC TGACTAATTTTTTTTATTTATGCAGAGGCCGAGGCCGCCTCGG CCTCTGAGCTATTCCAGAAGTAGTGAGGAGGCTTTTTTGGAGG CCTAGGCTTTTGCAAAAAGCTAACTTGTTTATTGCAGCTTATA ATGGTTACAAATAAAGCAATAGCATCACAAATTTCACAAATAA AGCATTTTTTCACTGCATTCTAGTTGTGGTTTGTCCAAACTC ATCAATGTATCTTATCACCCGGG |
| 31 | Elongation Factor-1 alpha (EF1-alpha) promoter | CCGGTGCCTAGAGAAGGTGGCGCGGGGTAAACTGGGAAAGTGA TGTCGTGTACTGGCTCCGCCTTTTTCCCGAGGGTGGGGGAGAA CCGTATATAAGTGCAGTAGTCGCCGTGAACGTTCTTTTTCGCA ACGGGTTTGCCGCCAGAACACAGGTAAGTGCCGTGTGTGGTTC CCGCGGGCCTGGCCTCTTTACGGGTTATGGCCCTTGCGTGCCT TGAATTACTTCCACGCCCCTGGCTGCAGTACGTGATTCTTGAT CCCGAGCTTCGGGTTGGAAGTGGGTGGGAGAGTTCGAGGCCTT GCGCTTAAGGAGCCCCTTCGCCTCGTGCTTGAGTTGAGGCCTG GCCTGGGCGCTGGGGCCGCCGCGTGCGAATCTGGTGGCACCTT CGCGCCTGTCTCGCTGCTTTCGATAAGTCTCTAGCCATTTAAA ATTTTTGATGACCTGCTGCGACGCTTTTTTTCTGGCAAGATAG TCTTGTAAATGCGGGCCAAGATCTGCACACTGGTATTTCGGTT TTTGGGGCCGCGGGCGGCGACGGGGCCCGTGCGTCCCAGCGCA CATGTTCGGCGAGGCGGGGCCTGCGAGCGCGGCCACCGAGAAT CGGACGGGGGTAGTCTCAAGCTGGCCGGCCTGCTCTGGTGCCT GGCCTCGCGCCGCCGTGTATCGCCCCGCCCTGGGCGGCAAGGC TGGCCCGGTCGGCACCAGTTGCGTGAGCGGAAAGATGGCCGCT TCCCGGCCCTGCTGCAGGGAGCTCAAAATGGAGGACGCGGCGC TCGGGAGAGCGGGCGGGTGAGTCACCCACACAAAGGAAAAGGG CCTTTCCGTCCTCAGCCGTCGCTTCATGTGACTCCACGGAGTA CCGGGCGCCGTCCAGGCACCTCGATTAGTTCTCGAGCTTTTGG AGTACGTCGTCTTTAGGTTGGGGGGAGGGGTTTTATGCGATGG AGTTTCCCCACACTGAGTGGGTGGAGACTGAAGTTAGGCCAGC TTGGCACTTGATGTAATTCTCCTTGGAATTTGCCCTTTTTGAG TTTGGATCTTGGTTCATTCTCAAGCCTCAGACAGTGGTTCAAA GTTTTTTTCTTCCATTTCAGGTGTCGTGA |
| 32 | Promoter; PGK | GGGGTTGGGGTTGCGCCTTTTCCAAGGCAGCCCTGGGTTTGCG CAGGGACGCGGCTGCTCTGGGCGTGGTTCCGGGAAACGCAGCG GCGCCGACCCTGGGTCTCGCACATTCTTCACGTCCGTTCGCAG CGTCACCCGGATCTTCGCCGCTACCCTTGTGGGCCCCCCGGCG ACGCTTCCTGCTCCGCCCCTAAGTCGGGAAGGTTCCTTGCGGT TCGCGGCGTGCCGGACGTGACAAACGGAAGCCGCACGTCTCAC TAGTACCCTCGCAGACGGACAGCGCCAGGGAGCAATGGCAGCG CGCCGACCGCGATGGGCTGTGGCCAATAGCGGCTGCTCAGCAG GGCGCGCCGAGAGCAGCGGCCGGGAAGGGGCGGTGCGGGAGGC GGGGTGTGGGGCGGTAGTGTGGGCCCTGTTCCTGCCCGCGCGG TGTTCCGCATTCTGCAAGCCTCCGGAGCGCACGTCGGCAGTCG GCTCCCTCGTTGACCGAATCACCGACCTCTCTCCCCAG |
| 33 | Promoter; UbC | GCGCCGGGTTTTGGCGCCTCCCGCGGGCGCCCCCCTCCTCACG GCGAGCGCTGCCACGTCAGACGAAGGGCGCAGGAGCGTTCCTG ATCCTTCCGCCCGGACGCTCAGGACAGCGGCCCGCTGCTCATA AGACTCGGCCTTAGAACCCCAGTATCAGCAGAAGGACATTTTA GGACGGGACTTGGGTGACTCTAGGGCACTGGTTTTCTTTCCAG AGAGCGGAACAGGCGAGGAAAAGTAGTCCCTTCTCGGCGATTC TGCGGAGGGATCTCCGTGGGGCGGTGAACGCCGATGATTATAT AAGGACGCGCCGGGTGTGGCACAGCTAGTTCCGTCGCAGCCGG |

-continued

| SEQ ID NO: | Description | Sequence |
|---|---|---|
| | | GATTTGGGTCGCGGTTCTTGTTTGTGGATCGCTGTGATCGTCA<br>CTTGGTGAGTTGCGGGCTGCTGGGCTGGCCGGGGCTTTCGTGG<br>CCGCCGGGCCGCTCGGTGGGACGGAAGCGTGTGGAGAGACCGC<br>CAAGGGCTGTAGTCTGGGTCCGCGAGCAAGGTTGCCCTGAACT<br>GGGGGGTTGGGGGGAGCGCACAAAATGGCGGCTGTTCCCGAGTC<br>TTGAATGGAAGACGCTTGTAAGGCGGGCTGTGAGGTCGTTGAA<br>ACAAGGTGGGGGGCATGGTGGGCGGCAAGAACCCAAGGTCTTG<br>AGGCCTTCGCTAATGCGGGAAAGCTCTTATTCGGGTGAGATGG<br>GCTGGGGCACCATCTGGGGACCCTGACGTGAAGTTTGTCACTG<br>ACTGGAGAACTCGGGTTTGTCGTCTGGTTGCGGGGGCGGCAGT<br>TATGCGGTGCCGTTGGGCAGTGCACCCGTACCTTTGGGAGCGC<br>GCGCCTCGTCGTGTCGTGACGTCACCCGTTCTGTTGGCTTATA<br>ATGCAGGGTGGGGCCACCTGCCGGTAGGTGTGCGGTAGGCTTT<br>TCTCCGTCGCAGGACGCAGGGTTCGGGCCTAGGGTAGGCTCTC<br>CTGAATCGACAGGCGCCGGACCTCTGGTGAGGGGAGGGATAAG<br>TGAGGCGTCAGTTTCTTTGGTCGGTTTTATGTACCTATCTTCT<br>TAAGTAGCTGAAGCTCCGGTTTTGAACTATGCGCTCGGGGTTG<br>GCGAGTGTGTTTTGTGAAGTTTTTTAGGCACCTTTTGAAATGT<br>AATCATTTGGGTCAATATGTAATTTTCAGTGTTAGACTAGTAA<br>A |
| 34 | Poly A; SV40 | GTTTATTGCAGCTTATAATGGTTACAAATAAAGCAATAGCATC<br>ACAAATTTCACAAATAAAGCATTTTTTTCACTGCATTCTAGTT<br>GTGGTTTGTCCAAACTCATCAATGTATCTTATCA |
| 35 | Poly A; bGH | GACTGTGCCTTCTAGTTGCCAGCCATCTGTTGTTTGCCCCTCC<br>CCCGTGCCTTCCTTGACCCTGGAAGGTGCCACTCCCACTGTCC<br>TTTCCTAATAAAATGAGGAAATTGCATCGCATTGTCTGAGTAG<br>GTGTCATTCTATTCTGGGGGGTGGGGTGGGGCAGGACAGCAAG<br>GGGGAGGATTGGGAAGACAATAGCAGGCATGCTGGGGATGCGG<br>TGGGCTCTATGG |
| 36 | Envelope; RD 114 | ATGAAACTCCCAACAGGAATGGTCATTTTATGTAGCCTAATAA<br>TAGTTCGGGCAGGGTTTGACGACCCCCGCAAGGCTATCGCATT<br>AGTACAAAAACAACATGGTAAACCATGCGAATGCAGCGGAGGG<br>CAGGTATCCGAGGCCCCACCGAACTCCATCCAACAGGTAACTT<br>GCCCAGGCAAGACGGCCTACTTAATGACCAACCAAAAATGGAA<br>ATGCAGAGTCACTCCAAAAAATCTCACCCCTAGCGGGGGAGAA<br>CTCCAGAACTGCCCCTGTAACACTTTCCAGGACTCGATGCACA<br>GTTCTTGTTATACTGAATACCGGCAATGCAGGGCGAATAATAA<br>GACATACTACACGGCCACCTTGCTTAAAATACGGTCTGGGAGC<br>CTCAACGAGGTACAGATATTACAAAACCCCAATCAGCTCCTAC<br>AGTCCCCTTGTAGGGGCTCTATAAATCAGCCCGTTTGCTGGAG<br>TGCCACAGCCCCCATCCATATCTCCGATGGTGGAGGACCCCTC<br>GATACTAAGAGAGTGTGGACAGTCCAAAAAAGGCTAGAACAAA<br>TTCATAAGGCTATGCATCCTGAACTTCAATACCACCCCTTAGC<br>CCTGCCCAAAGTCAGAGATGACCTTAGCCTTGATGCACGGACT<br>TTTGATATCTGAATACCACTTTTAGGTTACTCCAGATGTCCA<br>ATTTTAGCCTTGCCCAAGATTGTTGGCTCTGTTTAAAACTAGG<br>TACCCCTACCCCTCTTGCGATACCCACTCCCTCTTTAACCTAC<br>TCCCTAGCAGACTCCCTAGCGAATGCCTCCTGTCAGATTATAC<br>CTCCCCTCTTGGTTCAACCGATGCAGTTCTCCAACTCGTCCTG<br>TTTATCTTCCCCTTTCATTAACGATACGGAACAAATAGACTTA<br>GGTGCAGTCACCTTTACTAACTGCACCTCTGTAGCCAATGTCA<br>GTAGTCCTTTATGTGCCCTAAACGGGTCAGTCTTCCTCTGTGG<br>AAATAACATGGCATACACCTATTTACCCCAAAACTGGACAGGA<br>CTTTGCGTCCAAGCCTCCCTCCTCCCCGACATTGACATCATCC<br>CGGGGGATGAGCCAGTCCCCATTCCTGCCATTGATCATTATAT<br>ACATAGACCTAAACGAGCTGTACAGTTCATCCCTTTACTAGCT<br>GGACTGGGAATCACCGCAGCATTCACCACCGGAGCTACAGGCC<br>TAGGTGTCTCCGTCACCCAGTATACAAAATTATCCCATCAGTT<br>AATATCTGATGTCCAAGTCTTATCCGGTACCATACAAGATTTA<br>CAAGACCAGGTAGACTCGTTAGCTGAAGTAGTTCTCCAAAATA<br>GGAGGGGACTGGACCTACTAACGGCAGAACAAGGAGGAATTTG<br>TTTAGCCTTACAAGAAAAATGCTGTTTTTATGCTAACAAGTCA<br>GGAATTGTGAGAAACAAAATAAGAACCCTACAAGAAGAATTAC<br>AAAAACGCAGGGAAAGCCTGGCATCCAACCCTCTCTGGACCGG<br>GCTGCAGGGCTTTCTTCCGTACCTCCTACCTCTCCTGGGACCC<br>CTACTCACCCTCCTACTCATACTAACCATTGGGCCATGCGTTT<br>TCAATCGATTGGTCCAATTTGTTAAAGACAGGATCTCAGTGGT<br>CCAGGCTCTGGTTTTGACTCAGCAATATCACCAGCTAAAACCC<br>ATAGAGTACGAGCCATGA |
| 37 | Envelope; GALV | ATGCTTCTCACCTCAAGCCCGCACCACCTTCGGCACCAGATGA<br>GTCCTGGGAGCTGGAAAAGACTGATCATCCTTCTTAAGCTGCGT<br>ATTCGGAGACGGCAAAACGAGTCTGCAGAATAAGAACCCCCAC |

| SEQ ID NO: | Description | Sequence |
|---|---|---|
| | | CAGCCTGTGACCCTCACCTGGCAGGTACTGTCCCAAACTGGGG<br>ACGTTGTCTGGGACAAAAAGGCAGTCCAGCCCCTTTGGACTTG<br>GTGGCCCTCTCTTACACCTGATGTATGTGCCCTGGCGGCCGGT<br>CTTGAGTCCTGGGATATCCCGGGATCCGATGTATCGTCCTCTA<br>AAAGAGTTAGACCTCCTGATTCAGACTATACTGCCGCTTATAA<br>GCAAATCACCTGGGGAGCCATAGGGTGCAGCTACCCTCGGGCT<br>AGGACCAGGATGGCAAATTCCCCCTTCTACGTGTGTCCCCGAG<br>CTGGCCGAACCCATTCAGAAGCTAGGAGGTGTGGGGGGCTAGA<br>ATCCCTATACTGTAAAGAATGGAGTTGTGAGACCACGGGTACC<br>GTTTATTGGCAACCCAAGTCCTCATGGGACCTCATAACTGTAA<br>AATGGGACCAAAATGTGAAATGGGAGCAAAAATTTCAAAAGTG<br>TGAACAAACCGGCTGGTGTAACCCCCTCAAGATAGACTTCACA<br>GAAAAAGGAAAACTCTCCAGAGATTGGATAACGGAAAAAACCT<br>GGGAATTAAGGTTCTATGTATATGGACACCCAGGCATACAGTT<br>GACTATCCGCTTAGAGGTCACTAACATGCCGGTTGTGGCAGTG<br>GGCCCAGACCCTGTCCTTGCGGAACAGGGACCTCCTAGCAAGC<br>CCCTCACTCTCCCTCTCTCCCACGGAAAGCGCCGCCCACCCC<br>TCTACCCCCGGCGGCTAGTGAGCAAACCCCTGCGGTGCATGGA<br>GAAACTGTTACCCTAAACTCTCCGCCTCCCACCAGTGGCGACC<br>GACTCTTTGGCCTTGTGCAGGGGGCCTTCCTAACCTTGAATGC<br>TACCAACCCAGGGGCCACTAAGTCTTGCTGGCTCTGTTTGGGC<br>ATGAGCCCCCTTATTATGAAGGGATAGCCTCTTCAGGAGAGG<br>TCGCTTATACCTCCAACCATACCCGATGCCACTGGGGGGCCCA<br>AGGAAAGCTTACCCTCACTGAGGTCTCCGGACTCGGGTCATGC<br>ATAGGGAAGGTGCCTCTTACCCATCAACATCTTTGCAACCAGA<br>CCTTACCCATCAATTCCTCTAAAAACCATCAGTATCTGCTCCC<br>CTCAAACCATAGCTGGTGGGCCTGCAGCACTGGCCTCACCCCC<br>TGCCTCTCCACCTCAGTTTTTAATCAGTCTAAAGACTTCTGTG<br>TCCAGGTCCAGCTGATCCCCCGCATCTATTACCATTCTGAAGA<br>AACCTTGTTACAAGCCTATGACAAATCACCCCCCAGGTTTAAA<br>AGAGAGCCTGCCTCACTTACCCTAGCTGTCTTCCTGGGGTTAG<br>GGATTGCGGCAGGTATAGGTACTGGCTCAACCGCCCTAATTAA<br>AGGGCCCATAGACCTCCAGCAAGGCCTAACCAGCCTCCAAATC<br>GCCATTGACGCTGACCTCCGGGCCCTTCAGGACTCAATCAGCA<br>AGCTAGAGGACTCACTGACTTCCCTATCTGAGGTAGTACTCCA<br>AAATAGGAGAGGCCTTGACTTACTATTCCTTAAAGAAGGAGGC<br>CTCTGCGCGGCCCTAAAAGAAGAGTGCTGTTTTTATGTAGACC<br>ACTCAGGTGCAGTACGAGACTCCATGAAAAACTTAAAGAAAG<br>ACTAGATAAAAGACAGTTAGAGCGCCAGAAAAACCAAAACTGG<br>TATGAAGGGTGGTTCAATAACTCCCCTTGGTTTACTACCCTAC<br>TATCAACCATCGCTGGGCCCCTATTGCTCCTCCTTTTGTTACT<br>CACTCTTGGGCCCTGCATCATCAATAAATTAATCCAATTCATC<br>AATGATAGGATAAGTGCAGTCAAAATTTTAGTCCTTAGACAGA<br>AATATCAGACCCTAGATAACGAGGAAAACCTTTAA |
| 38 | Envelope; FUG | ATGGTTCCGCAGGTTCTTTTGTTTGTACTCCTTCTGGGTTTTT<br>CGTTGTGTTTCGGGAAGTTCCCCATTTACACGATACCAGACGA<br>ACTTGGTCCCTGGAGCCCTATTGACATACACCATCTCAGCTGT<br>CCAAATAACCTGGTTGTGGAGGATGAAGGATGTACCAACCTGT<br>CCGAGTTCTCCTACATGGAACTCAAAGTGGGATACATCTCAGC<br>CATCAAAGTGAACGGGTTCACTTGCACAGGTGTTGTGACAGAG<br>GCAGAGACCTACACCAACTTTGTTGGTTATGTCACAACCACAT<br>TCAAGAGAAAGCATTTCCGCCCCACCCCAGACGCATGTAGAGC<br>CGCGTATAACTGGAAGATGGCCGGTGACCCCAGATATGAAGAG<br>TCCCTACACAATCCATACCCCGACTACCACTGGCTTCGAACTG<br>TAAGAACCACCAAAGAGTCCCTCATTATCATATCCCCAAGTGT<br>GACAGATTTGGACCCATATGACAAATCCCTTCACTCAAGGGTC<br>TTCCCTGGCGGAAAGTGCTCAGGAATAACGGTGTCCTCTACCT<br>ACTGCTCAACTAACCATGATTACACCATTTGGATGCCCGAGAA<br>TCCGAGACCAAGGACACCTTGTGACATTTTTACCAATAGCAGA<br>GGGAAGAGAGCATCCAACGGGAACAAGACTTGCGGCTTTGTGG<br>ATGAAAGAGGCCTGTATAAGTCTCTAAAAGGAGCATGCAGGCT<br>CAAGTTATGTGGAGTTCTTGGACTTAGACTTATGGATGGAACA<br>TGGGTCGCGATGCAAACATCAGATGAGACCAAATGGTGCCCTC<br>CAGATCAGTTGGTGAATTTGCACGACTTTCGCTCAGACGAGAT<br>CGAGCATCTCGTTGTGGAGGAGTTAGTTAAGAAAAGAGAGGAA<br>TGTCTGGATGCATTAGAGTCCATCATGACCACCAAGTCAGTAA<br>GTTTCAGACGTCTCAGTCACCTGAGAAAACTTGTCCCAGGGTT<br>TGGAAAAGCATATACCATATTCAACAAAACCTTGATGGAGGCT<br>GATGCTCACTACAAGTCAGTCCGGACCTGGAATGAGATCATCC<br>CCTCAAAAGGGTGTTTGAAAGTTGGAGGAAGGTGCCATCCTCA<br>TGTGAACGGGGTGTTTTTCAATGGTATAATATTAGGGCCTGAC<br>GACCATGTCCTAATCCCAGAGATGCAATCATCCCTCCTCCAGC<br>AACATATGGAGTTGTTGGAATCTTCAGTTATCCCCCTGATGCA<br>CCCCCTGGCAGACCCTTCTACAGTTTTCAAAGAAGGTGATGAG<br>GCTGAGGATTTTGTTGAAGTTCACCTCCCCGATGTGTACAAAC |

-continued

| SEQ ID NO: | Description | Sequence |
|---|---|---|
| | | AGATCTCAGGGGTTGACCTGGGTCTCCCGAACTGGGGAAAGTA<br>TGTATTGATGACTGCAGGGGCCATGATTGGCCTGGTGTTGATA<br>TTTTCCCTAATGACATGGTGCAGAGTTGGTATCCATCTTTGCA<br>TTAAATTAAAGCACACCAAGAAAAGACAGATTTATACAGACAT<br>AGAGATGAACCGACTTGGAAAGTAA |
| 39 | Envelope; LCMV | ATGGGTCAGATTGTGACAATGTTTGAGGCTCTGCCTCACATCA<br>TCGATGAGGTGATCAACATTGTCATTATTGTGCTTATCGTGAT<br>CACGGGTATCAAGGCTGTCTACAATTTTGCCACCTGTGGGATA<br>TTCGCATTGATCAGTTTCCTACTTCTGGCTGGCAGGTCCTGTG<br>GCATGTACGGTCTTAAGGGACCCGACATTTACAAAGGAGTTTA<br>CCAATTTAAGTCAGTGGAGTTTGATATGTCACATCTGAACCTG<br>ACCATGCCCAACGCATGTTCAGCCAACAACTCCCACCATTACA<br>TCAGTATGGGGACTTCTGGACTAGAATTGACCTTCACCAATGA<br>TTCCATCATCAGTCACAACTTTTGCAATCTGACCTCTGCCTTC<br>AACAAAAAGACCTTTGACCACACACTCATGAGTATAGTTTCGA<br>GCCTACACCTCAGTATCAGAGGGAACTCCAACTATAAGGCAGT<br>ATCCTGCGACTTCAACAATGGCATAACCATCCAATACAACTTG<br>ACATTCTCAGATCGACAAAGTGCTCAGAGCCAGTGTAGAACCT<br>TCAGAGGTAGAGTCCTAGATATGTTTAGAACTGCCTTCGGGGG<br>GAAATACATGAGGAGTGGCTGGGCTGGACAGGCTCAGATGGC<br>AAGACCACCTGGTGTAGCCAGACGAGTTACCAATACCTGATTA<br>TACAAAATAGAACCTGGGAAAACCACTGCACATATGCAGGTCC<br>TTTTGGGATGTCCAGGATTCTCCTTTCCCAAGAGAAGACTAAG<br>TTCTTCACTAGGAGACTAGCGGGCACATTCACCTGGACTTTGT<br>CAGACTCTTCAGGGGTGGAGAATCCAGGTGGTTATTGCCTGAC<br>CAAATGGATGATTCTTGCTGCAGAGCTTAAGTGTTTCGGGAAC<br>ACAGCAGTTGCGAAATGCAATGTAAATCATGATGCCGAATTCT<br>GTGACATGCTGCGACTAATTGACTACAACAAGGCTGCTTTGAG<br>TAAGTTCAAAGAGGACGTAGAATCTGCCTTGCACTTATTCAAA<br>ACAACAGTGAATTCTTTGATTTCAGATCAACTACTGATGAGGA<br>ACCACTTGAGAGATCTGATGGGGGTGCCATATTGCAATTACTC<br>AAAGTTTTGGTACCTAGAACATGCAAAGACCGGCGAAACTAGT<br>GTCCCCAAGTGCTGGCTTGTCACCAATGGTTCTTACTTAAATG<br>AGACCCACTTCAGTGATCAAATCGAACAGGAAGCCGATAACAT<br>GATTACAGAGATGTTGAGGAAGGATTACATAAAGAGGCAGGGG<br>AGTACCCCCCTAGCATTGATGGACCTTCTGATGTTTTCCACAT<br>CTGCATATCTAGTCAGCATCTTCCTGCACCTTGTCAAAATACC<br>AACACACAGGCACATAAAAGGTGGCTCATGTCCAAAGCCACAC<br>CGATTAACCAACAAAGGAATTTGTAGTTGTGGTGCATTTAAGG<br>TGCCTGGTGTAAAAACCGTCTGGAAAAGACGCTGA |
| 40 | Envelope; FPV | ATGAACACTCAAATCCTGGTTTTCGCCCTTGTGGCAGTCATCC<br>CCACAAATGCAGACAAAATTTGTCTTGGACATCATGCTGTATC<br>AAATGGCACCAAAGTAAACACACTCACTGAGAGAGGAGTAGAA<br>GTTGTCAATGCAACGGAAACAGTGGAGCGGACAAACATCCCCA<br>AAATTTGCTCAAAAGGGAAAGAACCACTGATCTTGGCCAATG<br>CGGACTGTTAGGGACCATTACCGGACCACCTCAATGCGACCAA<br>TTTCTAGAATTTTCAGCTGATCTAATAATCGAGAGACGAGAAG<br>GAAATGATGTTTGTTACCCGGGGAAGTTTGTTAATGAAGAGGC<br>ATTGCGACAAATCCTCAGAGGATCAGGTGGGATTGACAAAGAA<br>ACAATGGGATTCACATATAGTGGAATAAGGACCAACGGAACAA<br>CTAGTGCATGTAGAAGATCAGGGTCTTCATTCTATGCAGAAAT<br>GGAGTGGCTCCTGTCAAATACAGACAATGCTGCTTTCCCACAA<br>ATGACAAAATCATACAAAAACACAAGGAGAGAATCAGCTCTGA<br>TAGTCTGGGGAATCCACCATTCAGGATCAACCACCGAACAGAC<br>CAAACTATATGGGAGTGGAAATAAACTGATAACAGTCGGGAGT<br>TCCAAATATCATCAATCTTTTGTGCCGAGTCCAGGAACACGAC<br>CGCAGATAAATGGCCAGTCCGGACGGATTGATTTTCATTGGTT<br>GATCTTGGATCCCAATGATACAGTTACTTTTAGTTTCAATGGG<br>GCTTTCATAGCTCCAAATCGTGCCAGCTTCTTGAGGGGAAAGT<br>CCATGGGATCCAGAGCGATGTGCAGGTTGATGCCAATTGCGA<br>AGGGGAATGCTACCACAGTGGAGGGACTATAACAAGCAGATTG<br>CCTTTTCAAAACATCAATAGCAGAGCAGTTGGCAAATGCCCAA<br>GATATGTAAAACAGGAAAGTTTATTATTGGCAACTGGGATGAA<br>GAACGTTCCCGAACCTTCCAAAAAAAGGAAAAAAAGAGGCCTG<br>TTTGGCGCTATAGCAGGGTTTATTGAAAATGGTTGGGAAGGTC<br>TGGTCGACGGGTGGTACGGTTTCAGGCATCAGAATGCACAAGG<br>AGAAGGAACTGCAGCAGACTACAAAAGCACCCAATCGGCAATT<br>GATCAGATAACCGGAAAGTTAAATAGACTTCATTGAGAAAACCA<br>ACCAGCAATTTGAGCTAATAGATAATGAATTCACTGAGGTGGA<br>AAAGCAGATTGGCAATTTAATTAACTGGACCAAAGACTCCATC<br>ACAGAAGTATGGTCTTACAATGCTGAACTTCTTGTGGCAATGG<br>AAAACCAGCACACTATTGATTTGGCTGATTCAGAGATGAACAA<br>GCTGTATGAGCGAGTGAGGAAACAATTAAGGGAAAATGCTGAA<br>GAGGATGGCACTGGTTGCTTTGAAATTTTTCATAAATGTGACG |

-continued

| SEQ ID NO: | Description | Sequence |
|---|---|---|
| | | ATGATTGTATGGCTAGTATAAGGAACAATACTTATGATCACAG<br>CAAATACAGAGAAGAAGCGATGCAAAATAGAATACAAATTGAC<br>CCAGTCAAATTGAGTAGTGGCTACAAAGATGTGATACTTTGGT<br>TTAGCTTCGGGGCATCATGCTTTTTGCTTCTTGCCATTGCAAT<br>GGGCCTTGTTTTCATATGTGTGAAGAACGGAAACATGCGGTGC<br>ACTATTTGTATATAA |
| 41 | Envelope; RRV | AGTGTAACAGAGCACTTTAATGTGTATAAGGCTACTAGACCAT<br>ACCTAGCACATTGCGCCGATTGCGGGGACGGGTACTTCTGCTA<br>TAGCCCAGTTGCTATCGAGGAGATCCGAGATGAGGCGTCTGAT<br>GGCATGCTTAAGATCCAAGTCTCCGCCCAAATAGGTCTGGACA<br>AGGCAGGCACCCACGCCCACACGAAGCTCCGATATATGGCTGG<br>TCATGATGTTCAGGAATCTAAGAGAGATTCCTTGAGGGTGTAC<br>ACGTCCGCAGCGTGCTCCATACATGGGACGATGGGACACTTCA<br>TCGTCGCACACTGTCCACCAGGCGACTACCTCAAGGTTTCGTT<br>CGAGGACGCAGATTCGCACGTGAAGGCATGTAAGGTCCAATAC<br>AAGCACAATCCATTGCCGGTGGGTAGAGAGAAGTTCGTGGTTA<br>GACCACACTTTGGCGTAGAGCTGCCATGCACCTCATACCAGCT<br>GACAACGGCTCCCACCGACGAGGAGATTGACATGCATACACCG<br>CCAGATATACCGGATCGCACCCTGCTATCACAGACGGCGGGCA<br>ACGTCAAAATAACAGCAGGCGGCAGGACTATCAGGTACAACTG<br>TACCTGCGGCCGTGACAACGTAGGCACTACCAGTACTGACAAG<br>ACCATCAACACATGCAAGATTGACCAATGCCATGCTGCCGTCA<br>CCAGCCATGACAAATGGCAATTTACCTCTCCATTTGTTCCCAG<br>GGCTGATCAGACAGCTAGGAAAGGCAAGGTACACGTTCCGTTC<br>CCTCTGACTAACGTCACCTGCCGAGTGCCGTTGGCTCGAGCGC<br>CGGATGCCACCTATGGTAAGAAGGAGGTGACCCTGAGATTACA<br>CCCAGATCATCCGACGCTCTTCTCCTATAGGAGTTTAGGAGCC<br>GAACCGCACCCGTACGAGGAATGGGTTGACAAGTTCTCTGAGC<br>GCATCATCCCAGTGACGGAAGAAGGGATTGAGTACCAGTGGGG<br>CAACAACCCGCCGGTCTGCCTGTGGGCGCAACTGACGACCGAG<br>GGCAAACCCCATGGCTGGCCACATGAAATCATTCAGTACTATT<br>ATGGACTATACCCCGCCGCCACTATTGCCGCAGTATCCGGGGC<br>GAGTCTGATGGCCCTCCTAACTCTGGCGGCCACATGCTGCATG<br>CTGGCCACCGCGAGGAGAAAGTGCCTAACACCGTACGCCCTGA<br>CGCCAGGAGCGGTGGTACCGTTGACACTGGGGCTGCTTTGCTG<br>CGCACCGAGGGCGAATGCA |
| 42 | Envelope; MLV 10A1 | ATGGAAGGTCCAGCGTTCTCAAAACCCCTTAAAGATAAGATTA<br>ACCCGTGGAAGTCCTTAATGGTCATGGGGGTCTATTTAAGAGT<br>AGGGATGGCAGAGAGCCCCCATCAGGTCTTTAATGTAACCTGG<br>AGAGTCACCAACCTGATGACTGGGCGTACCGCCAATGCCACCT<br>CCCTTTTAGGAACTGTACAAGATGCCTTCCCAAGATTATATTT<br>TGATCTATGTGATCTGGTCGGAGAAGAGTGGGACCCTTCAGAC<br>CAGGAACCATATGTCGGGTATGGCTGCAAATACCCCGGAGGGA<br>GAAAGCGGACCCGGACTTTTGACTTTTACGTGTGCCCTGGGCA<br>TACCGTAAAATCGGGGTGTGGGGGGCCAAGAGAGGGCTACTGT<br>GGTGAATGGGGTTGTGAAACCACCGGACAGGCTTACTGGAAGC<br>CCACATCATCATGGGACCTAATCTCCCTTAAGCGCGGTAACAC<br>CCCCTGGGACACGGGATGCTCCAAAATGGCTTGTGGCCCCTGC<br>TACGACCTCTCCAAAGTATCCAATTCCTTCCAAGGGGCTACTC<br>GAGGGGGCAGATGCAACCCTCTAGTCCTAGAATTCACTGATGC<br>AGGAAAAAAGGCTAATTGGGACGGGCCCAAATCGTGGGGACTG<br>AGACTGTACCGGACAGGAACAGATCCTATTACCATGTTCTCCC<br>TGACCCGCCAGGTCCTCAATATAGGGCCCCGCATCCCCATTGG<br>GCCTAATCCCGTGATCACTGGTCAACTACCCCCCTCCCGACCC<br>GTGCAGATCAGGCTCCCCAGGCCTCCTCAGCCTCCTCCTACAG<br>GCGCAGCCTCTATAGTCCCTGAGACTGCCCCACCTTCTCAACA<br>ACCTGGGACGGGAGACAGGCTGCTAAACCTGGTAGAAGGAGCC<br>TATCAGGCGCTTAACCTCACCAATCCCGACAAGACCCAAGAAT<br>GTTGGCTGTGCTTAGTGTCGGGACCTCCTTATTACGAAGGAGT<br>AGCGGTCGTGGGCACTTATACCAATCATTCTACCGCCCCGGCC<br>AGCTGTACGGCCACTTCCCAACATAAGCTTACCCTATCTGAAG<br>TGACAGGACAGGGCCTATGCATGGGAGCACTACCTAAAACTCA<br>CCAGGCCTTATGTAACACCACCCAAAGTGCCGGCTCAGGATCC<br>TACTACCTTGCAGCACCCGCTGGAACAATGTGGGCTTGTAGCA<br>CTGGATTGACTCCCTGCTTGTCCACCACGATGCTCAATCTAAC<br>CACAGACTATTGTGTATTAGTTGAGCTCTGGCCCAGAATAATT<br>TACCACTCCCCCGATTATATGTATGGTCAGCTTGAACAGCGTA<br>CCAAATATAAGAGGGAGCCAGTATCGTTGACCCTGGCCCTTCT<br>GCTAGGAGGATTAACCATGGGAGGGATTGCAGCTGGAATAGGG<br>ACGGGGACCACTGCCCTAATCAAAACCCAGCAGTTTGAGCAGC<br>TTCACGCCGCTATCCAGACAGACCTCAACGAAGTCGAAAAATC<br>AATTACCAACCTAGAAAAGTCACTGACCTCGTTGTCTGAAGTA<br>GTCCTACAGAACCGAAGAGGCCTAGATTTGCTCTTCCTAAAAG<br>AGGGAGGTCTCTGCGCAGCCCTAAAAGAAGAATGTTGTTTTTA |

| SEQ ID NO: | Description | Sequence |
|---|---|---|
| | | TGCAGACCACACGGGACTAGTGAGAGACAGCATGGCCAAACTA<br>AGGGAAAGGCTTAATCAGAGACAAAAACTATTTGAGTCAGGCC<br>AAGGTTGGTTCGAAGGGCAGTTTAATAGATCCCCCTGGTTTAC<br>CACCTTAATCTCCACCATCATGGGACCTCTAATAGTACTCTTA<br>CTGATCTTACTCTTTGGACCCTGCATTCTCAATCGATTGGTCC<br>AATTTGTTAAAGACAGGATCTCAGTGGTCCAGGCTCTGGTTTT<br>GACTCAACAATATCACCAGCTAAAACCTATAGAGTACGAGCCA<br>TGA |
| 43 | Envelope; Ebola | ATGGGTGTTACAGGAATATTGCAGTTACCTCGTGATCGATTCA<br>AGAGGACATCATTCTTTCTTTGGGTAATTATCCTTTTCCAAAG<br>AACATTTTCCATCCCACTTGGAGTCATCCACAATAGCACATTA<br>CAGGTTAGTGATGTCGACAAACTGGTTTGCCGTGACAAACTGT<br>CATCCACAAATCAATTGAGATCAGTTGGACTGAATCTCGAAGG<br>GAATGGAGTGGCAACTGACGTGCCATCTGCAACTAAAAGATGG<br>GGCTTCAGGTCCGGTGTCCCACCAAAGGTGGTCAATTATGAAG<br>CTGGTGAATGGGCTGAAAACTGCTACAATCTTGAAATCAAAAA<br>ACCTGACGGGAGTGAGTGTCTACCAGCAGCGCCAGACGGGATT<br>CGGGGCTTCCCCCGGTGCCGGTATGTGCACAAAGTATCAGGAA<br>CGGGACCGTGTGCCGGAGACTTTGCCTTCCACAAAGAGGGTGC<br>TTTCTTCCTGTATGACCGACTTGCTTCCACAGTTATCTACCGA<br>GGAACGACTTTCGCTGAAGGTGTCGTTGCATTTCTGATACTGC<br>CCCAAGCTAAGAAGGACTTCTTCAGCTCACACCCCTTGAGAGA<br>GCCGGTCAATGCAACGGAGGACCCGTCTAGTGGCTACTATTCT<br>ACCACAATTAGATATCAAGCTACCGGTTTTGGAACCAATGAGA<br>CAGAGTATTTGTTCGAGGTTGACAATTTGACCTACGTCCAACT<br>TGAATCAAGATTCACACCACAGTTTCTGCTCCAGCTGAATGAG<br>ACAATATATACAAGTGGGAAAAGGAGCAATACCACGGGAAAAC<br>TAATTTGGAAGGTCAACCCCGAAATTGATACAACAATCGGGGA<br>GTGGGCCTTCTGGGAAACTAAAAAAACCTCACTAGAAAAATTC<br>GCAGTGAAGAGTTGTCTTTCACAGCTGTATCAAACAGAGCCAA<br>AAACATCAGTGGTCAGAGTCCGGCGCGAACTTCTTCCGACCCA<br>GGGACCAACACAACAACTGAAGACCACAAAATCATGGCTTCAG<br>AAAATTCCTCTGCAATGGTTCAAGTGCACAGTCAAGGAAGGGA<br>AGCTGCAGTGTCGCATCTGACAACCCTTGCCACAATCTCCACG<br>AGTCCTCAACCCCCCACAACCAAACCAGGTCCGGACAACAGCA<br>CCCACAATACACCCGTGTATAAACTTGACATCTCTGAGGCAAC<br>TCAAGTTGAACAACATCACCGCAGAACAGACAACGACAGCACA<br>GCCTCCGACACTCCCCCCGCCACGACCGCAGCCGGACCCCTAA<br>AAGCAGAGAACACCAACACGAGCAAGGGTACCGACCTCCTGGA<br>CCCCGCCACCACAACAAGTCCCCAAAACCACAGCGAGACCGCT<br>GGCAACAACAACACTCATCACCAAGATACCGGAGAAGAGAGTG<br>CCAGCAGCGGGAAGCTAGGCTTAATTACCAATACTATTGCTGG<br>AGTCGCAGGACTGATCACAGGCGGGAGGAGAGCTCGAAGAGAA<br>GCAATTGTCAATGCTCAACCCAAATGCAACCCTAATTTACATT<br>ACTGGACTACTCAGGATGAAGGTGCTGCAATCGGACTGGCCTG<br>GATACCATATTTCGGGCCAGCAGCCGAGGGAATTTACATAGAG<br>GGGCTGATGCACAATCAAGATGGTTTAATCTGTGGGTTGAGAC<br>AGCTGGCCAACGAGACGACTCAAGCTCTTCAACTGTTCCTGAG<br>AGCCACAACCGAGCTACGCACCTTTTCAATCCTCAACCGTAAG<br>GCAATTGATTTCTTGCTGCAGCGATGGGCGGCACATGCCACA<br>TTTTGGGACCGGACTGCTGTATCGAACCACATGATTGGACCAA<br>GAACATAACAGACAAATTGATCAGATTATTCATGATTTTGTT<br>GATAAAACCCTTCCGGACCAGGGGGACAATGACAATTGGTGGA<br>CAGGATGGAGACAATGGATACCGGCAGGTATTGGAGTTACAGG<br>CGTTATAATTGCAGTTATCGCTTTATTCTGTATATGCAAATTT<br>GTCTTTTAG |
| 44 | Forward Primer to amplify Gag, Pol, and Integrase | TAAGCAGAATTCATGAATTTGCCAGGAAGAT |
| 45 | Reverse Primer to amplify Gag, Pol, and Integrase | CCATACAATGAATGGACACTAGGCGGCCGCACGAAT |
| 46 | KIF11 Forward Primer | CCGTTCTGGAGCTGTTGATAA |
| 47 | KIF11 Reverse Primer | TGTTCTTTCTACAAGGGCAGTAA |
| 48 | KIF11 TaqMan Probe (Fam/Iowa Black Zen quencher) | CCCTGTTGACTTTGGGAAGGGTCA |

| SEQ ID NO: | Description | Sequence |
|---|---|---|
| 49 | Actin forward primer | GGACCTGACTGACTACCTCAT |
| 50 | Actin reverse primer #1 | CGTAGCACAGCTTCTCCTTAAT |
| 51 | Actin reverse primer #2 | ATTAAGGAGAAGCTGTGCTACG |
| 52 | Actin probe (FAM or VIC/Iowa Black Zen) | AGCGGGAAATCGTGCGTGAC |
| 53 | Gag forward primer | GGAGCTAGAACGATTCGCAGTTA |
| 54 | Gag reverse primer | TGTAGCTGTCCCAGTATTTGTC |
| 55 | Gag probe (FAM/Iowa Black Zen) | CCTGGCCTGTTAGAAACATCAGAAGGCTGT |
| 56 | Non-targeting shRNA sequence | GCCGCTTTGTAGGATAGAGCTCGAGCTCTATCCTACAAAGCGGCTTTTT |

What is claimed is:

1. A modified mesenchymal stem cell comprising a mesenchymal stem cell infected with a lentiviral particle, wherein the lentiviral particle comprises:
   an envelope protein capable of infecting the mesenchymal stem cell; and
   a first nucleotide sequence encoding a small RNA capable of binding a non-coding region of a host copy of KIF11,
   wherein the small RNA comprises a sequence having at least 80% sequence identity with at least one of SEQ ID NO: 1, SEQ ID NO: 2, or SEQ ID NO: 3.

2. The modified mesenchymal stem cell of claim 1, wherein the small RNA comprises at least one of SEQ ID NO: 1, SEQ ID NO: 2, or SEQ ID NO: 3.

3. A method of producing a modified mesenchymal stem cell, the method comprising:
   infecting a mesenchymal stem cell with an effective amount of a lentiviral particle, wherein the lentiviral particle comprises:
      an envelope protein capable of infecting the mesenchymal stem cell; and
      a first nucleotide sequence encoding a small RNA capable of binding a non-coding region of a host copy of KIF11,
      wherein the small RNA comprises a sequence having at least 80% sequence identity with at least one of SEQ ID NO: 1, SEQ ID NO: 2, or SEQ ID NO: 3.

4. The method of claim 3, wherein the small RNA comprises at least one of SEQ ID NO: 1, SEQ ID NO: 2, or SEQ ID NO: 3.

5. A viral vector comprising a first nucleotide sequence encoding a small RNA capable of binding a non-coding region of a host copy of KIF11,
   wherein the small RNA comprises a sequence having at least 80% sequence identity with at least one of SEQ ID NO: 1, SEQ ID NO: 2, or SEQ ID NO: 3.

6. The viral vector of claim 5, wherein the small RNA comprises at least one of SEQ ID NO: 1, SEQ ID NO: 2, or SEQ ID NO: 3.

7. A lentiviral particle produced by a packaging cell and capable of infecting a target cell, the lentiviral particle comprising:
   an envelope protein capable of infecting the target cell; and
   a first nucleotide sequence encoding a small RNA capable of binding a non-coding region of a host copy of KIF11,
   wherein the small RNA comprises a sequence having at least 80% sequence identity with at least one of SEQ ID NO: 1, SEQ ID NO: 2, or SEQ ID NO: 3.

8. The lentiviral particle of claim 7, wherein the small RNA comprises at least one of SEQ ID NO: 1, SEQ ID NO: 2, or SEQ ID NO: 3.

* * * * *

```
                       SEQUENCE LISTING

<160> NUMBER OF SEQ ID NOS: 56

<210> SEQ ID NO 1
<211> LENGTH: 53
<212> TYPE: DNA
<213> ORGANISM: Artificial Sequence
<220> FEATURE:
<223> OTHER INFORMATION: KIF11 small RNA sequence #1

<400> SEQUENCE: 1
tttgatctgg caaccatatt tctcgagaaa tatggttgcc agatcaaatt ttt          53

<210> SEQ ID NO 2
<211> LENGTH: 53
<212> TYPE: DNA
<213> ORGANISM: Artificial Sequence
<220> FEATURE:
<223> OTHER INFORMATION: KIF11 small RNA sequence #2

<400> SEQUENCE: 2
tgcaatgtaa atacgtattt cctcgaggaa atacgtattt acattgcatt ttt          53

<210> SEQ ID NO 3
<211> LENGTH: 51
<212> TYPE: DNA
<213> ORGANISM: Artificial Sequence
<220> FEATURE:
<223> OTHER INFORMATION: KIF11 small RNA sequence #3

<400> SEQUENCE: 3
gcttgagctt acataggtaa ctcgagttac ctatgtaagc tcaagctttt t            51

<210> SEQ ID NO 4
<211> LENGTH: 3171
<212> TYPE: DNA
<213> ORGANISM: Artificial Sequence
<220> FEATURE:
<223> OTHER INFORMATION: KIF11 sequence
```

-continued

```
<400> SEQUENCE: 4
atggcgtcgc agccaaattc gtctgcgaag aagaaagagg agaaggggaa gaacatccag      60
gtggtggtga gatgcagacc atttaatttg gcagagcgga aagctagcgc ccattcaata     120
gtagaatgtg atcctgtacg aaaagaagtt agtgtacgaa ctggaggatt ggctgacaag     180
agctcaagga aaacatacac ttttgatatg gtgtttggag catctactaa acagattgat     240
gtttaccgaa gtgttgtttg tccaattctg gatgaagtta ttatgggcta taattgcact     300
atctttgcgt atggccaaac tggcactgga aaaactttta caatggaagg tgaaaggtca     360
cctaatgaag agtatacctg ggaagaggat cccttggctg gtataattcc acgtacccct     420
catcaaattt ttgagaaact tactgataat ggtactgaat tttcagtcaa agtgtctctg     480
ttggagatct ataatgaaga cttttttgat cttcttaatc catcatctga tgtttctgag     540
agactacaga tgtttgatga tccccgtaac aagagaggag tgataattaa aggtttagaa     600
gaaattacag tacacaacaa ggatgaagtc tatcaaattt tagaaaaggg ggcagcaaaa     660
aggacaactg cagctactct gatgaatgca tactctagtc gttcccactc agttttctct     720
gttacaatac atatgaaaga aactacgatt gatggagaag agcttgttaa aatcggaaag     780
ttgaacttgg ttgatcttgc aggaagtgaa aacattggcc gttctggagc tgttgataag     840
agagctcggg aagctggaaa tataaatcaa tccctgttga ctttgggaag ggtcattact     900
gcccttgtaa aagaacacc tcatgttcct tatcgagaat ctaaactaac tagaatcctc     960
caggattctc ttggagggcg tacaagaaca tctataattg caacaatttc tcctgcatct    1020
ctcaatcttg aggaaactct gagtacattg gaatatgctc atagagcaaa gaacatattg    1080
aataagcctg aagtgaatca gaaactcacc aaaaaagctc ttattaagga gtatacggag    1140
gagatagaac gttaaaacg agatcttgct gcagcccgtg agaaaaatgg agtgtatatt    1200
tctgaagaaa attttagagt catgagtgga aaattaactg ttcaagaaga gcagattgta    1260
gaattgattg aaaaaaattgg tgctgttgag gaggagctga atagggttac agagttgttt    1320
atggataata aaaatgaact tgaccagtgt aaatctgacc tgcaaaataa aacacaagaa    1380
cttgaaacca ctcaaaaaca tttgcaagaa actaaattac aacttgttaa agaagaatat    1440
atcacatcag ctttggaaag tactgaggag aaacttcatg atgctgccag caagctgctt    1500
aacacagttg aagaaactac aaaagatgta tctggtctcc attccaaact ggatcgtaag    1560
aaggcagttg accaacacaa tgcagaagct caggatattt ttggcaaaaa cctgaatagt    1620
ctgtttaata atatggaaga attaattaag gatggcagct caaagcaaaa ggccatgcta    1680
gaagtacata agaccttatt tggtaatctg ctgtcttcca gtgtctctgc attagatacc    1740
attactacag tagcacttgg atctctcaca tctattccag aaaatgtgtc tactcatgtt    1800
tctcagattt ttaatatgat actaaaagaa caatcattag cagcagaaag taaaactgta    1860
ctacaggaat tgattaatgt actcaagact gatcttctaa gttcactgga aatgatttta    1920
tccccaactg tggtgtctat actgaaaatc aatagtcaac taaagcatat tttcaagact    1980
tcattgacag tggccgataa gatagaagat caaaaaaagg aactagatgg ctttctcagt    2040
atactgtgta acaatctaca tgaactacaa gaaaatacca tttgttcctt ggttgagtca    2100
caaaagcaat gtggaaacct aactgaagac ctgaagacaa taaagcagac ccattcccag    2160
gaactttgca agttaatgaa tctttggaca gagagattct gtgctttgga ggaaagtgt     2220
gaaaatatac agaaaccact tagtagtgtc caggaaaata tacagcagaa atctaaggat    2280
atagtcaaca aaatgacttt tcacagtcaa aaattttgtg ctgattctga tggcttctca    2340
```

| | | |
|---|---|---|
| caggaactca gaaattttaa ccaagaaggt acaaaattgg ttgaagaatc tgtgaaacac | 2400 |
| tctgataaac tcaatggcaa cctgaaaaaa atatctcaag agactgaaca gagatgtgaa | 2460 |
| tctctgaaca caagaacagt ttattttct gaacagtggg tatcttcctt aaatgaaagg | 2520 |
| gaacaggaac ttcacaactt attggaggtt gtaagccaat gttgtgaggc ttcaagttca | 2580 |
| gacatcactg agaaatcaga tggacgtaag gcagctcatg agaaacagca taacattttt | 2640 |
| cttgatcaga tgactattga tgaagataaa ttgatagcac aaaatctaga acttaatgaa | 2700 |
| accataaaaa ttggtttgac taagcttaat tgctttctgg aacaggatct gaaactggat | 2760 |
| atcccaacag gtacgacacc acagaggaaa agttatttat acccatcaac actggtaaga | 2820 |
| actgaaccac gtgaacatct ccttgatcag ctgaaaagga acagcctga gctgttaatg | 2880 |
| atgctaaact gttcagaaaa caacaaagaa gagacaattc cggatgtgga tgtagaagag | 2940 |
| gcagttctgg ggcagtatac tgaagaacct ctaagtcaag agccatctgt agatgctggt | 3000 |
| gtggattgtt catcaattgg cggggttcca tttttccagc ataaaaaatc acatggaaaa | 3060 |
| gacaaagaaa acagaggcat taacacactg gagaggtcta agtggaaga aactacagag | 3120 |
| cacttggtta caaagagcag attacctctg cgagcccaga tcaacccttta a | 3171 |

<210> SEQ ID NO 5
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 5

| | | |
|---|---|---|
| gtagtcttat gcaatactct tgtagtcttg caacatggta acgatgagtt agcaacatgc | 60 |
| cttacaagga gagaaaaagc accgtgcatg ccgattggtg gaagtaaggt ggtacgatcg | 120 |
| tgccttatta ggaaggcaac agacgggtct gacatggatt ggacgaacca ctgaattgcc | 180 |
| gcattgcaga gatattgtat ttaagtgcct agctcgatac aataaacg | 228 |

<210> SEQ ID NO 6
<211> LENGTH: 180
<212> TYPE: DNA
<213> ORGANISM: Artificial Sequence
<220> FEATURE:
<223> OTHER INFORMATION: 5' Long terminal repeat (LTR)

<400> SEQUENCE: 6

| | | |
|---|---|---|
| ggtctctctg gttagaccag atctgagcct gggagctctc tggctaacta gggaacccac | 60 |
| tgcttaagcc tcaataaagc ttgccttgag tgcttcaagt agtgtgtgcc cgtctgttgt | 120 |
| gtgactctgg taactagaga tccctcagac cctttagtc agtgtggaaa atctctagca | 180 |

<210> SEQ ID NO 7
<211> LENGTH: 41
<212> TYPE: DNA
<213> ORGANISM: Artificial Sequence
<220> FEATURE:
<223> OTHER INFORMATION: Psi Packaging signal

<400> SEQUENCE: 7

| | | |
|---|---|---|
| tacgccaaaa attttgacta gcggaggcta aaggagaga g | 41 |

<210> SEQ ID NO 8
<211> LENGTH: 233
<212> TYPE: DNA

<213> ORGANISM: Artificial Sequence
<220> FEATURE:
<223> OTHER INFORMATION: Rev response element (RRE)

<400> SEQUENCE: 8

```
aggagctttg ttccttgggt tcttgggagc agcaggaagc actatgggcg cagcctcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcc          233
```

<210> SEQ ID NO 9
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 9

```
ttttaaaaga aaaggggggga ttggggggta cagtgcaggg gaaagaatag tagacataat    60
agcaacagac atacaaacta agaattaca aaaacaaatt acaaaattca aaattttta    118
```

<210> SEQ ID NO 10
<211> LENGTH: 217
<212> TYPE: DNA
<213> ORGANISM: Artificial Sequence
<220> FEATURE:
<223> OTHER INFORMATION: Polymerase III shRNA promoters - H1 promoter

<400> SEQUENCE: 10

```
gaacgctgac gtcatcaacc cgctccaagg aatcgcgggc ccagtgtcac taggcgggaa    60
cacccagcgc gcgtgcgccc tggcaggaag atggctgtga gggacagggg agtggcgccc   120
tgcaatattt gcatgtcgct atgtgttctg ggaaatcacc ataaacgtga atgtctttg   180
gatttgggaa tcttataagt tctgtatgag accactt                            217
```

<210> SEQ ID NO 11
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 11

```
aatcaacctc tgattacaaa atttgtgaaa gattgactgg tattcttaac tatgttgctc    60
cttttacgct atgtggatac gctgctttaa tgcctttgta tcatgctatt gcttcccgta   120
tggctttcat tttctcctcc ttgtataaat cctggttgct gtctctttat gaggagttgt   180
ggcccgttgt caggcaacgt ggcgtggtgt gcactgtgtt gctgacgca accccactg    240
gttgggcat tgccaccacc tgtcagctcc tttccgggac tttcgctttc ccctccta   300
ttgccacggc ggaactcatc gccgcctgcc ttgcccgctg ctggacaggg gctcggctgt   360
tgggcactga caattccgtg gtgttgtcgg ggaaatcatc gtcctttcct ggctgctcg   420
cctgtgttgc cacctggatt ctgcgcggga cgtccttctg ctacgtccct tcggccctca   480
atccagcgga ccttccttcc cgcggcctgc tgccggctct gcggcctctt ccgcgtcttc   540
gccttcgccc tcagacgagt cggatctccc tttgggccgc ctccccgcct              590
```

<210> SEQ ID NO 12
<211> LENGTH: 250

```
<212> TYPE: DNA
<213> ORGANISM: Artificial Sequence
<220> FEATURE:
<223> OTHER INFORMATION: 3' delta LTR

<400> SEQUENCE: 12
tggaagggct aattcactcc caacgaagat aagatctgct ttttgcttgt actgggtctc    60
tctggttaga ccagatctga gcctgggagc tctctggcta actagggaac ccactgctta   120
agcctcaata aagcttgcct tgagtgcttc aagtagtgtg tgcccgtctg ttgtgtgact   180
ctggtaacta gagatccctc agaccctttt agtcagtgtg aaaatctct agcagtagta    240 gttcatgtca                                                          250

<210> SEQ ID NO 13
<211> LENGTH: 290
<212> TYPE: DNA
<213> ORGANISM: Artificial Sequence
<220> FEATURE:
<223> OTHER INFORMATION: Helper/Rev - Chicken beta actin (CAG)
      promoter - Transcription

<400> SEQUENCE: 13
gctattacca tgggtcgagg tgagccccac gttctgcttc actctcccca tctcccccc    60 ctccccaccc ccaattttgt atttatttat tttttaatta ttttgtgcag cgatgggggc   120 ggggggggggg ggggcgcgcg ccaggcgggg cggggcgggg cgaggggcgg ggcggggcga   180
ggcggagagg tgcggcggca gccaatcaga gcggcgcgct ccgaaagttt cctttatgg   240 cgaggcggcg gcggcggcgg ccctataaaa agcgaagcgc gcggcgggcg               290

<210> SEQ ID NO 14
<211> LENGTH: 1503
<212> TYPE: DNA
<213> ORGANISM: Artificial Sequence
<220> FEATURE:
<223> OTHER INFORMATION: Helper/Rev - HIV Gag - Viral capsid

<400> SEQUENCE: 14
atgggtgcga gagcgtcagt attaagcggg ggagaattag atcgatggga aaaaattcgg    60
ttaaggccag ggggaaagaa aaaatataaa ttaaaacata tagtatgggc aagcagggag   120
ctagaacgat tcgcagttaa tcctggcctg ttagaaacat cagaaggctg tagacaaata   180
ctgggacagc tacaaccatc ccttcagaca ggatcagaag aacttagatc attatataat   240
acagtagcaa ccctctattg tgtgcatcaa aggatagaga taaaagacac caaggaagct   300
ttagacaaga tagaggaaga gcaaaacaaa agtaagaaaa agcacagca agcagcagct    360 gacacaggac acagcaatca ggtcagccaa aattacccta tagtgcagaa catccagggg   420
caaatggtac atcaggccat atcacctaga actttaaatg catgggtaaa agtagtagaa   480
gagaaggctt tcagcccaga agtgataccc atgttttcag cattatcaga aggagccacc   540
ccacaagatt taaacaccat gctaaacaca gtggggggga tcaagcagc catgcaaatg    600 ttaaaagaga ccatcaatga ggaagctgca gaatgggata gagtgcatcc agtgcatgca    660
gggcctattg caccaggcca gatgagagaa ccaaggggaa gtgacatagc aggaactact   720
agtacccttc aggaacaaat aggatggatg acacataatc cacctatccc agtaggagaa   780
atctataaaa gatggataat cctgggatta aataaaatag taagaatgta tagccctacc   840
agcattctgg acataagaca aggaccaaag gaacccttta gagactatgt agaccgattc   900
tataaaactc taagagccga gcaagcttca caagaggtaa aaaattggat gacagaaacc   960
```

| | |
|---|---|
| ttgttggtcc aaaatgcgaa cccagattgt aagactatt taaaagcatt gggaccagga | 1020 |
| gcgacactag aagaaatgat gacagcatgt cagggagtgg ggggacccgg ccataaagca | 1080 |
| agagttttgg ctgaagcaat gagccaagta acaaatccag ctaccataat gatacagaaa | 1140 |
| ggcaatttta ggaaccaaag aaagactgtt aagtgtttca attgtggcaa agaagggcac | 1200 |
| atagccaaaa attgcagggc ccctaggaaa aagggctgtt ggaaatgtgg aaggaagga | 1260 |
| caccaaatga aagattgtac tgagagacag gctaattttt tagggaagat ctggccttcc | 1320 |
| cacaagggaa ggccagggaa ttttcttcag agcagaccag agccaacagc cccaccagaa | 1380 |
| gagagcttca ggtttgggga agagacaaca actccctctc agaagcagga gccgatagac | 1440 |
| aaggaactgt atcctttagc ttccctcaga tcactctttg gcagcgaccc ctcgtcacaa | 1500 |
| taa | 1503 |

<210> SEQ ID NO 15
<211> LENGTH: 1872
<212> TYPE: DNA
<213> ORGANISM: Artificial Sequence
<220> FEATURE:
<223> OTHER INFORMATION: Helper/Rev - HIV Pol - Protease and reverse
      transcriptase

<400> SEQUENCE: 15

| | |
|---|---|
| atgaatttgc caggaagatg gaaaccaaaa atgatagggg gaattggagg ttttatcaaa | 60 |
| gtaggacagt atgatcagat actcatagaa atctgcggac ataaagctat aggtacagta | 120 |
| ttagtaggac ctacacctgt caacataatt ggaagaaatc tgttgactca gattggctgc | 180 |
| actttaaatt ttcccattag tcctattgag actgtaccag taaaattaaa gccaggaatg | 240 |
| gatggcccaa aagttaaaca atggccattg acagaagaaa aaataaaagc attagtagaa | 300 |
| atttgtacag aaatggaaaa ggaaggaaaa atttcaaaaa ttgggcctga aaatccatac | 360 |
| aatactccag tatttgccat aaagaaaaaa gacagtacta atggagaaaa attagtagat | 420 |
| ttcagagaac ttaataagag aactcaagat ttctgggaag ttcaattagg aataccacat | 480 |
| cctgcagggt taaaacagaa aaaatcagta acagtactgg atgtgggcga tgcatatttt | 540 |
| tcagttccct tagataaaga cttcaggaag tatactgcat ttaccatacc tagtataaac | 600 |
| aatgagacac cagggattag atatcagtac aatgtgcttc cacagggatg gaaaggatca | 660 |
| ccagcaatat tccagtgtag catgacaaaa atcttagagc cttttagaaa acaaaatcca | 720 |
| gacatagtca tctatcaata catggatgat ttgtatgtag gatctgactt agaaataggg | 780 |
| cagcatagaa caaaaataga ggaactgaga caacatctgt tgaggtgggg atttaccaca | 840 |
| ccagacaaaa aacatcagaa agaacctcca ttcctttgga tgggttatga actccatcct | 900 |
| gataaatgga cagtacagcc tatagtgctg ccagaaaagg acagctggac tgtcaatgac | 960 |
| atacagaaat tagtgggaaa attgaattgg gcaagtcaga tttatgcagg gattaaagta | 1020 |
| aggcaattat gtaaacttct taggggaacc aaagcactaa cagaagtagt accactaaca | 1080 |
| gaagaagcag agctagaact ggcagaaaac agggagattc taaaagaacc ggtacatgga | 1140 |
| gtgtattatg acccatcaaa agacttaata gcagaaatac agaagcaggg gcaaggccaa | 1200 |
| tggacatatc aaatttatca agagccattt aaaaatctga aaacaggaaa atatgcaaga | 1260 |
| atgaagggtg cccacactaa tgatgtaaaa caattaacag aggcagtaca aaaaatagcc | 1320 |
| acagaaagca tagtaatatg gggaaagact cctaaattta aattacccat acaaaaggaa | 1380 |
| acatgggaag catggtggac agagtattgg caagccacct ggattcctga gtgggagttt | 1440 |

```
gtcaataccc ctcccttagt gaagttatgg taccagttag agaaagaacc cataatagga   1500
gcagaaactt tctatgtaga tggggcagcc aatagggaaa ctaaattagg aaaagcagga   1560
tatgtaactg acagaggaag acaaaaagtt gtcccctaa cggacacaac aaatcagaag    1620
actgagttac aagcaattca tctagctttg caggattcgg gattagaagt aaacatagtg   1680
acagactcac aatatgcatt gggaatcatt caagcacaac cagataagag tgaatcagag   1740
ttagtcagtc aaataataga gcagttaata aaaaaggaaa aagtctacct ggcatgggta   1800
ccagcacaca aaggaattgg aggaaatgaa caagtagatg ggttggtcag tgctggaatc   1860
aggaaagtac ta                                                        1872

<210> SEQ ID NO 16
<211> LENGTH: 867
<212> TYPE: DNA
<213> ORGANISM: Artificial Sequence
<220> FEATURE:
<223> OTHER INFORMATION: Helper Rev - HIV Integrase - Integration of
      viral RNA

<400> SEQUENCE: 16
tttttagatg gaatagataa ggcccaagaa gaacatgaga atatcacag taattggaga     60 gcaatggcta gtgattttaa cctaccacct gtagtagcaa aagaaatagt agccagctgt   120
gataaatgtc agctaaaagg ggaagccatg catggacaag tagactgtag cccaggaata   180
tggcagctag attgtacaca tttagaagga aaagttatct tggtagcagt tcatgtagcc   240
agtggatata tagaagcaga agtaattcca gcagagacag ggcaagaaac agcatacttc   300
ctcttaaaat tagcaggaag atggccagta aaaacagtac atacagacaa tggcagcaat   360
ttcaccagta ctacagttaa ggccgcctgt tggtgggcgg ggatcaagca ggaatttggc   420
attccctaca atccccaaag tcaaggagta atagaatcta tgaataaaga attaaagaaa   480
attataggac aggtaagaga tcaggctgaa catcttaaga cagcagtaca aatggcagta   540
ttcatccaca attttaaaag aaaagggggg attggggggt acagtgcagg ggaaagaata   600
gtagacataa tagcaacaga catacaaact aaagaattac aaaaacaaat tacaaaaatt   660
caaaattttc gggtttatta cagggacagc agagatccag tttggaaagg accagcaaag   720
ctcctctgga aaggtgaagg ggcagtagta atacaagata atagtgacat aaaagtagtg   780
ccaagaagaa aagcaaagat catcagggat tatggaaaac agatggcagg tgatgattgt   840
gtggcaagta gacaggatga ggattaa                                       867

<210> SEQ ID NO 17
<211> LENGTH: 234
<212> TYPE: DNA
<213> ORGANISM: Artificial Sequence
<220> FEATURE:
<223> OTHER INFORMATION: Helper/Rev - HIV RRE - Binds Rev element

<400> SEQUENCE: 17
aggagctttg ttccttgggt tcttgggagc agcaggaagc actatgggcg cagcgtcaat   60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcct          234

<210> SEQ ID NO 18
<211> LENGTH: 351
```

```
<212> TYPE: DNA
<213> ORGANISM: Artificial Sequence
<220> FEATURE:
<223> OTHER INFORMATION: Helper/Rev - HIV Rev - Nuclear export and
      stabilize viral mRNA

<400> SEQUENCE: 18
atggcaggaa gaagcggaga cagcgacgaa gaactcctca aggcagtcag actcatcaag      60
tttctctatc aaagcaaccc acctcccaat cccgagggga cccgacaggc ccgaaggaat     120
agaagaagaa ggtggagaga gagacagaga cagatccatt cgattagtga acggatcctt     180
agcacttatc tgggacgatc tgcggagcct gtgcctcttc agctaccacc gcttgagaga     240
cttactcttg attgtaacga ggattgtgga acttctggga cgcaggggggt gggaagccct     300 caaatattgg tggaatctcc tacaatattg gagtcaggag ctaaagaata g              351

<210> SEQ ID NO 19
<211> LENGTH: 352
<212> TYPE: DNA
<213> ORGANISM: Artificial Sequence
<220> FEATURE:
<223> OTHER INFORMATION: Helper/Rev - CMV early (CAG) enhancer -
      EnhanceTranscription

<400> SEQUENCE: 19
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tc             352

<210> SEQ ID NO 20
<211> LENGTH: 960
<212> TYPE: DNA
<213> ORGANISM: Artificial Sequence
<220> FEATURE:
<223> OTHER INFORMATION: Helper/Rev - Chicken beta actin intron -
      Enhance gene expression

<400> SEQUENCE: 20
ggagtcgctg cgttgccttc gccccgtgcc ccgctccgcg ccgcctcgcg ccgcccgccc      60
cggctctgac tgaccgcgtt actcccacag gtgagcgggc gggacggccc ttctcctccg     120
ggctgtaatt agcgcttggt ttaatgacgg ctcgtttctt ttctgtggct gcgtgaaagc     180
cttaaagggc tccggagggc ccttttgtgc ggggggggagc ggctcggggg gtgcgtgcgt     240
gtgtgtgtgc gtggggagcg ccgcgtgcgg cccgcgctgc ccggcggctg tgagcgctgc     300
gggcgcggcg cggggctttg tgcgctccgc gtgtgcgcga ggggagcgcg gccggggggcg     360 gtgccccgcg gtgcgggggg gctgcgaggg gaacaaaggc tgcgtgcggg gtgtgtgcgt     420
gggggggtga gcaggggggtg tgggcgcggc ggtcgggctg taaccccccc ctgcaccccc     480
ctccccgagt tgctgagcac ggcccggctt cgggtgcggg gctccgtgcg gggcgtggcg     540
cggggctcgc cgtgccgggc ggggggtggc ggcaggtggg ggtgccgggc ggggcggggc     600
cgcctcgggc cggggagggc tcggggggagg gcgcggcgg ccccgagcg ccggcggctg     660 tcgaggcgcg gcgagccgca gccattgcct tttatggtaa tcgtgcgaga gggcgcaggg     720
acttcctttg tcccaaatct ggcggagccg aaatctggga ggcgccgccg cacccccctct     780
```

```
agcgggcgcg ggcgaagcgg tgcggcgccg gcaggaagga aatgggcggg gagggccttc     840
gtgcgtcgcc gcgccgccgt ccccttctcc atctccagcc tcggggctgc cgcaggggga     900
cggctgcctt cggggggggac ggggcagggc ggggttcggc ttctggcgtg tgaccggcgg    960
```

```
<210> SEQ ID NO 21
<211> LENGTH: 448
<212> TYPE: DNA
<213> ORGANISM: Artificial Sequence
<220> FEATURE:
<223> OTHER INFORMATION: Helper/Rev - Rabbit beta globin poly A - RNA
      stability

<400> SEQUENCE: 21 agatctttt ccctctgcca aaaattatgg ggacatcatg aagccccttg agcatctgac       60
ttctggctaa taaaggaaat ttattttcat tgcaatagtg tgttggaatt ttttgtgtct    120
ctcactcgga aggacatatg ggagggcaaa tcatttaaaa catcagaatg agtatttggt    180
ttagagtttg gcaacatatg ccatatgctg gctgccatga acaaaggtgg ctataaagag    240
gtcatcagta tatgaaacag ccccctgctg tccattcctt attccataga aaagccttga    300
cttgaggtta gatttttttt atatttgtt ttgtgttatt ttttcttta acatccctaa      360 aattttcctt acatgtttta ctagccagat ttttcctcct ctcctgacta ctcccagtca    420
tagctgtccc tcttctctta tgaagatc                                       448
```

```
<210> SEQ ID NO 22
<211> LENGTH: 577
<212> TYPE: DNA
<213> ORGANISM: Artificial Sequence
<220> FEATURE:
<223> OTHER INFORMATION: Envelope - CMV promoter - Transcription

<400> SEQUENCE: 22
acattgatta ttgactagtt attaatagta atcaattacg gggtcattag ttcatagccc       60
atatatggag ttccgcgtta cataacttac ggtaaatggc ccgcctggct gaccgcccaa    120 cgaccccgc ccattgacgt caataatgac gtatgttccc atagtaacgc caatagggac      180
tttccattga cgtcaatggg tggagtattt acggtaaact gcccacttgg cagtacatca    240
agtgtatcat atgccaagta cgccccctat tgacgtcaat gacggtaaat ggcccgcctg    300
gcattatgcc cagtacatga ccttatggga ctttcctact tggcagtaca tctacgtatt    360
agtcatcgct attaccatgg tgatgcggtt ttggcagtac atcaatgggc gtggatagcg    420
gtttgactca cggggatttc caagtctcca ccccattgac gtcaatggga gtttgttttg    480
gcaccaaaat caacgggact ttccaaaatg tcgtaacaac tccgccccat tgacgcaaat    540
gggcggtagg cgtgtacggt gggaggtcta tataagc                             577
```

```
<210> SEQ ID NO 23
<211> LENGTH: 573
<212> TYPE: DNA
<213> ORGANISM: Artificial Sequence
<220> FEATURE:
<223> OTHER INFORMATION: Envelope - Beta globin intron - Enhance gene
      expression

<400> SEQUENCE: 23
gtgagtttgg ggacccttga ttgttctttc ttttcgcta ttgtaaaatt catgttatat        60 ggaggggca aagttttcag ggtgttgttt agaatgggaa gatgtcccctt gtatcaccat    120
```

| | | | |
|---|---|---|---|
| ggaccctcat | gataattttg | tttctttcac | tttctactct gttgacaacc attgtctcct | 180 |
| cttattttct | tttcattttc | tgtaacttttt | tcgttaaact ttagcttgca tttgtaacga | 240 |
| atttttaaat | tcacttttgt | ttatttgtca | gattgtaagt actttctcta atcactttttt | 300 |
| tttcaaggca | atcagggtat | attatattgt | acttcagcac agttttagag aacaattgtt | 360 |
| ataattaaat | gataaggtag | aatatttctg | catataaatt ctggctggcg tggaaatatt | 420 |
| cttattggta | gaaacaacta | caccctggtc | atcatcctgc ctttctcttt atggttacaa | 480 |
| tgatatacac | tgtttgagat | gaggataaaa | tactctgagt ccaaaccggg ccctctgct | 540 |
| aaccatgttc | atgccttctt | ctctttccta | cag | 573 |

<210> SEQ ID NO 24
<211> LENGTH: 1531
<212> TYPE: DNA
<213> ORGANISM: Artificial Sequence
<220> FEATURE:
<223> OTHER INFORMATION: DNA fragment containing VSV-G

<400> SEQUENCE: 24

| | | | |
|---|---|---|---|
| gaattcatga | agtgccttttt | gtacttagcc | tttttattca ttggggtgaa ttgcaagttc | 60 |
| accatagttt | ttccacacaa | ccaaaaagga | aactggaaaa atgttccttc taattaccat | 120 |
| tattgcccgt | caagctcaga | tttaaattgg | cataatgact taataggcac agccttacaa | 180 |
| gtcaaaatgc | ccaagagtca | caaggctatt | caagcagacg gttggatgtg tcatgcttcc | 240 |
| aaatgggtca | ctacttgtga | tttccgctgg | tatggaccga agtatataac acattccatc | 300 |
| cgatccttca | ctccatctgt | agaacaatgc | aaggaaagca ttgaacaaac gaaacaagga | 360 |
| acttggctga | atccaggctt | ccctcctcaa | agttgtggat atgcaactgt gacggatgcc | 420 |
| gaagcagtga | ttgtccaggt | gactcctcac | catgtgctgg ttgatgaata cacaggagaa | 480 |
| tgggttgatt | cacagttcat | caacggaaaa | tgcagcaatt acatatgccc cactgtccat | 540 |
| aactctacaa | cctggcattc | tgactataag | gtcaaagggc tatgtgattc taacctcatt | 600 |
| tccatggaca | tcaccttctt | ctcagaggac | ggagagctat catccctggg aaaggagggc | 660 |
| acagggttca | gaagtaacta | ctttgcttat | gaaactggag gcaaggcctg caaaatgcaa | 720 |
| tactgcaagc | attggggagt | cagactccca | tcaggtgtct ggttcgagat ggctgataag | 780 |
| gatctctttg | ctgcagccag | attccctgaa | tgcccagaag gtcaagtat ctctgctcca | 840 |
| tctcagacct | cagtggatgt | aagtctaatt | caggacgttg agaggatctt ggattattcc | 900 |
| ctctgccaag | aaacctggag | caaaatcaga | gcgggtctctc aatctctcc agtggatctc | 960 |
| agctatcttg | ctcctaaaaa | cccaggaacc | ggtcctgctt tcaccataat caatggtacc | 1020 |
| ctaaaatact | ttgagaccag | atacatcaga | gtcgatattg ctgctccaat cctctcaaga | 1080 |
| atggtcggaa | tgatcagtgg | aactaccaca | gaaagggaac tgtgggatga ctgggcacca | 1140 |
| tatgaagacg | tggaaattgg | acccaatgga | gttctgagga ccagttcagg atataagttt | 1200 |
| cctttataca | tgattggaca | tggtatgttg | gactccgatc ttcatcttag ctcaaaggct | 1260 |
| caggtgttcg | aacatcctca | cattcaagac | gctgcttcgc aacttcctga tgatgagagt | 1320 |
| ttattttttg | gtgatactgg | gctatccaaa | aatccaatcg agcttgtaga aggttggttc | 1380 |
| agtagttgga | aaagctctat | tgcctcttttt | ttctttatca tagggttaat cattggacta | 1440 |
| ttcttggttc | tccgagttgg | tatccatctt | tgcattaaat taaagcacac caagaaaaga | 1500 |
| cagatttata | cagacataga | gatgagaatt | c | 1531 |

<210> SEQ ID NO 25
<211> LENGTH: 450
<212> TYPE: DNA
<213> ORGANISM: Artificial Sequence
<220> FEATURE:
<223> OTHER INFORMATION: Envelope - Rabbit beta globin poly A - RNA stability

<400> SEQUENCE: 25

```
agatctttt  ccctctgcca  aaaattatgg  ggacatcatg  aagccccttg  agcatctgac    60
ttctggctaa  taaaggaaat  ttatttcat   tgcaatagtg  tgttggaatt  ttttgtgtct   120
ctcactcgga  aggacatatg  ggagggcaaa  tcatttaaaa  catcagaatg  agtatttggt   180
ttagagtttg  gcaacatatg  cccatatgct  ggctgccatg  aacaaaggtt  ggctataaag   240
aggtcatcag  tatatgaaac  agccccctgc  tgtccattcc  ttattccata  gaaaagcctt   300
gacttgaggt  tagatttttt  ttatatttg   ttttgtgtta  ttttttcctt  taacatccct   360
aaaattttcc  ttacatgttt  tactagccag  attttcctc   ctctcctgac  tactcccagt   420
catagctgtc  cctcttctct  tatggagatc                                      450
```

<210> SEQ ID NO 26
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 26

```
gaattcatga  atttgccagg  aagatggaaa  ccaaaaatga  tagggggaat  tggaggtttt    60
atcaaagtaa  gacagtatga  tcagatactc  atagaaatct  gcggacataa  agctataggt   120
acagtattag  taggacctac  acctgtcaac  ataattggaa  gaaatctgtt  gactcagatt   180
ggctgcactt  taaatttccc  cattagtcct  attgagactg  taccagtaaa  attaaagcca   240
ggaatggatg  gcccaaaagt  taaacaatgg  ccattgacag  aagaaaaaat  aaaagcatta   300
gtagaaattt  gtacagaaat  ggaaaaggaa  ggaaaaattt  caaaaattgg  gcctgaaaat   360
ccatacaata  ctccagtatt  tgccataaag  aaaaaagaca  gtactaaatg  gagaaaatta   420
gtagatttca  gagaacttaa  taagagaact  caagatttct  gggaagttca  attaggaata   480
ccacatcctg  cagggttaaa  acagaaaaaa  tcagtaacag  tactggatgt  gggcgatgca   540
tatttttcag  ttcccttaga  taaagacttc  aggaagtata  ctgcatttac  catacctagt   600
ataaacaatg  agacaccagg  gattagatat  cagtacaatg  tgcttccaca  gggatggaaa   660
ggatcaccag  caatattcca  gtgtagcatg  acaaaaatct  tagagccttt  tagaaaacaa   720
aatccagaca  tagtcatcta  tcaatacatg  gatgatttgt  atgtaggatc  tgacttagaa   780
ataggcagc   atagaacaaa  aatagaggaa  ctgagacaac  atctgttgag  gtggggattt   840
accacaccag  acaaaaaaca  tcagaaagaa  cctccattcc  tttggatggg  ttatgaactc   900
catcctgata  aatggacagt  acagcctata  gtgctgccag  aaaaggacag  ctggactgtc   960
aatgacatac  agaaattagt  gggaaaattg  aattgggcaa  gtcagattta  tgcagggatt  1020
aaagtaaggc  aattatgtaa  acttcttagg  ggaaccaaag  cactaacaga  agtagtacca  1080
ctaacagaag  aagcagagct  agaactggca  gaaaacaggg  agattctaaa  agaaccggta  1140
catggagtgt  attatgaccc  atcaaaagac  ttaatagcag  aaatacagaa  gcaggggcaa  1200
ggccaatgga  catatcaaat  ttatcaagag  ccatttaaaa  atctgaaaac  aggaaagtat  1260
gcaagaatga  agggtgccca  cactaatgat  gtgaaacaat  taacagaggc  agtacaaaaa  1320
```

```
atagccacag aaagcatagt aatatgggga aagactccta aatttaaatt acccatacaa   1380
aaggaaacat gggaagcatg gtggacagag tattggcaag ccacctggat tcctgagtgg   1440
gagtttgtca atacccctcc cttagtgaag ttatggtacc agttagagaa agaacccata   1500
ataggagcag aaactttcta tgtagatggg gcagccaata gggaaactaa attaggaaaa   1560
gcaggatatg taactgacag aggaagacaa aaagttgtcc ccctaacgga cacaacaaat   1620
cagaagactg agttacaagc aattcatcta gctttgcagg attcgggatt agaagtaaac   1680
atagtgacag actcacaata tgcattggga atcattcaag cacaaccaga taagagtgaa   1740
tcagagttag tcagtcaaat aatagagcag ttaataaaaa aggaaaaagt ctacctggca   1800
tgggtaccag cacacaaagg aattggagga aatgaacaag tagataaatt ggtcagtgct   1860
ggaatcagga aagtactatt tttagatgga atagataagg cccaagaaga acatgagaaa   1920
tatcacagta attggagagc aatggctagt gattttaacc taccacctgt agtagcaaaa   1980
gaaatagtag ccagctgtga taatgtcag ctaaaagggg aagccatgca tggacaagta   2040
gactgtagcc caggaatatg gcagctagat tgtacacatt tagaaggaaa agttatcttg   2100
gtagcagttc atgtagccag tggatatata gaagcagaag taattccagc agagacaggg   2160
caagaaacag catacttcct cttaaaatta gcaggaagat ggccagtaaa aacagtacat   2220
acagacaatg gcagcaattt caccagtact acagttaagg ccgcctgttg gtgggcgggg   2280
atcaagcagg aatttggcat tccctacaat ccccaaagtc aaggagtaat agaatctatg   2340
aataaagaat taagaaaat tataggacag gtaagagatc aggctgaaca tcttaagaca   2400
gcagtacaaa tggcagtatt catccacaat tttaaaagaa aaggggggat tggggggtac   2460
agtgcagggg aaagaatagt agacataata gcaacagaca tacaaactaa agaattacaa   2520
aaacaaatta caaaaattca aaattttcgg gtttattaca gggacagcag agatccagtt   2580
tggaaaggac cagcaaagct cctctggaaa ggtgaagggg cagtagtaat acaagataat   2640
agtgacataa aagtagtgcc aagaagaaaa gcaaagatca tcagggatta tggaaaacag   2700
atggcaggtg atgattgtgt ggcaagtaga caggatgagg attaa               2745
```

<210> SEQ ID NO 27
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 27

```
tctagaatgg caggaagaag cggagacagc gacgaagagc tcatcagaac agtcagactc    60
atcaagcttc tctatcaaag caacccacct cccaatcccg aggggaccccg acaggcccga   120 aggaatagaa gaagaaggtg gagagagaga cagagacaga tccattcgat tagtgaacgg   180
atccttggca cttatctggg acgatctgcg gagcctgtgc ctcttcagct accaccgctt   240
gagagactta ctcttgattg taacgaggat tgtggaactt ctgggacgca gggggtggga   300
agccctcaaa tattggtgga atctcctaca atattggagt caggagctaa agaatagagg   360
agctttgttc cttgggttct tgggagcagc aggaagcact atgggcgcag cgtcaatgac   420
gctgacggta caggccagac aattattgtc tggtatagtg cagcagcaga caatttgct   480 gagggctatt gaggcgcaac agcatctgtt gcaactcaca gtctggggca tcaagcagct   540
ccaggcaaga atcctggctg tggaaagata cctaaaggat caacagctcc tagatctttt   600
```

```
tccctctgcc aaaaattatg gggacatcat gaagccccct gagcatctga cttctggcta        660
ataaaggaaa tttattttca ttgcaatagt gtgttggaat tttttgtgtc tctcactcgg        720
aaggacatat gggagggcaa atcatttaaa acatcagaat gagtatttgg tttagagttt        780
ggcaacatat gccatatgct ggctgccatg aacaaaggtg gctataaaga ggtcatcagt        840
atatgaaaca gccccctgct gtccattcct tattccatag aaaagccttg acttgaggtt        900
agattttttt tatattttgt tttgtgttat ttttttcttt aacatcccta aaattttcct        960
tacatgtttt actagccaga ttttcctcc tctcctgact actcccagtc atagctgtcc         1020
ctcttctctt atgaagatcc ctcgacctgc agcccaagct tggcgtaatc atggtcatag        1080
ctgtttcctg tgtgaaattg ttatccgctc acaattccac acaacatacg agccggaagc        1140
ataaagtgta aagcctgggg tgcctaatga gtgagctaac tcacattaat tgcgttgcgc        1200
tcactgcccg ctttccagtc gggaaacctg tcgtgccagc ggatccgcat ctcaattagt        1260
cagcaaccat agtcccgccc ctaactccgc ccatcccgcc cctaactccg cccagttccg        1320
cccattctcc gccccatggc tgactaattt ttttattta tgcagaggcc gaggccgcct         1380
cggcctctga gctattccag aagtagtgag gaggcttttt tggaggccta ggcttttgca        1440
aaaagctaac ttgtttattg cagcttataa tggttacaaa taaagcaata gcatcacaaa        1500
tttcacaaat aaagcatttt tttcactgca ttctagttgt ggtttgtcca aactcatcaa        1560
tgtatcttat cagcggccgc cccggg                                             1586
```

<210> SEQ ID NO 28  
<211> LENGTH: 1614  
<212> TYPE: DNA  
<213> ORGANISM: Artificial Sequence  
<220> FEATURE:  
<223> OTHER INFORMATION: DNA fragment containing the CAG enhancer/  
      promoter/intron sequence

<400> SEQUENCE: 28

```
acgcgttagt tattaatagt aatcaattac ggggtcatta gttcatagcc catatatgga         60
gttccgcgtt acataactta cggtaaatgg cccgcctggc tgaccgccca acgacccccg        120
cccattgacg tcaataatga cgtatgttcc catagtaacg ccaatagga ctttccattg         180 acgtcaatgg gtggactatt tacggtaaac tgcccacttg gcagtacatc aagtgtatca        240
tatgccaagt acgccccta ttgacgtcaa tgacggtaaa tggcccgcct ggcattatgc         300
ccagtacatg accttatggg actttcctac ttggcagtac atctacgtat tagtcatcgc        360
tattaccatg gtcgaggtg agccccacgt tctgcttcac tctccccatc tccccccct         420 ccccacccc aattttgtat ttatttattt ttaattatt ttgtgcagcg atggggggcgg         480 gggggggggg ggcgcgcgcc aggcggggcg ggcggggcg agggcggggg cggggcgagg        540
cggagaggtg cggcggcagc caatcagagc ggcgcgctcc gaaagtttcc ttttatggcg        600
aggcggcggc ggcggcggcc ctataaaaag cgaagcgcgc ggcgggcggg agtcgctgcg        660
ttgccttcgc cccgtgcccc gctccgcgcc gcctcgcgcc gcccgccccg gctctgactg        720
accgcgttac tcccacaggt gagcgggcgg gacggccctt ctcctccggg ctgtaattag        780
cgcttggttt aatgacggct cgtttctttt ctgtggctgc gtgaaagcct taaagggctc        840
cgggagggcc ctttgtgcgg gggggagcgg ctcgggggt gcgtgcgtgt gtgtgtgcgt         900
ggggagcgcc gcgtgcggcc gcgctgccc ggcggctgtg agcgctgcgg gcgcggcgcg         960
gggctttgtg cgctccgcgt gtgcgcgagg ggagcgcggc cggggcggt gccccgcggt        1020
```

```
gcggggggc  tgcgagggga  acaaaggctg  cgtgcgggt   gtgtgcgtgg  ggggtgagc   1080 aggggtgtg   ggcgcggcgg  tcgggctgta  accccccct   gcacccccct  ccccgagttg  1140
ctgagcacgg  cccggcttcg  ggtgcggggc  tccgtgcggg  gcgtggcgcg  gggctcgccg  1200
tgccgggcgg  ggggtggcgg  caggtggggg  tgccgggcgg  ggcggggccg  cctcgggccg  1260
gggagggctc  ggggagggg   cgcggcggcc  ccggagcgcc  ggcggctgtc  gaggcgcggc  1320
gagccgcagc  cattgccttt  tatggtaatc  gtgcgagagg  gcgcagggac  ttcctttgtc  1380
ccaaatctgg  cggagccgaa  atctgggagg  cgccgccgca  cccctctag   cgggcgcggg  1440 cgaagcggtg  cggcgccggc  aggaaggaaa  tgggcgggga  gggccttcgt  gcgtcgccgc  1500
gccgccgtcc  ccttctccat  ctccagcctc  ggggctgccg  caggggacg   gctgccttcg  1560 ggggggacgg  ggcagggcgg  ggttcggctt  ctggcgtgtg  accggcggga  attc        1614
```

<210> SEQ ID NO 29
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 29

```
caattgcgat  gtacgggcca  gatatacgcg  tatctgaggg  gactagggtg  tgtttaggcg   60
aaaagcgggg  cttcggttgt  acgcggttag  gagtcccctc  aggatatagt  agtttcgctt  120
ttgcataggg  aggggaaat   gtagtcttat  gcaatacact  tgtagtcttg  caacatggta  180
acgatgagtt  agcaacatgc  cttacaagga  gagaaaagc   accgtgcatg  ccgattggtg  240
gaagtaaggt  ggtacgatcg  tgccttatta  ggaaggcaac  agacaggtct  gacatggatt  300
ggacgaacca  ctgaattccg  cattgcagag  ataattgtat  ttaagtgcct  agctcgatac  360
aataaacgcc  atttgaccat  tcaccacatt  ggtgtgcacc  tccaagctcg  agctcgttta  420
gtgaaccgtc  agatcgcctg  gagacgccat  ccacgctgtt  ttgacctcca  tagaagacac  480
cgggaccgat  ccagcctccc  ctcgaagcta  gcgattaggc  atctcctatg  gcaggaagaa  540
gcggagacag  cgacgaagaa  ctcctcaagg  cagtcagact  catcaagttt  ctctatcaaa  600
gcaacccacc  tcccaatccc  gaggggaccc  gacaggcccg  aaggaataga  agaagaaggt  660
ggagagagag  acagagacag  atccattcga  ttagtgaacg  gatccttagc  acttatctgg  720
gacgatctgc  ggagcctgtg  cctcttcagc  taccaccgct  tgagagactt  actcttgatt  780
gtaacgagga  ttgtggaact  tctgggacgc  aggggtggg   aagccctcaa  atattggtgg  840
aatctcctac  aatattggag  tcaggagcta  agaatagtc   taga                    884
```

<210> SEQ ID NO 30
<211> LENGTH: 1227
<212> TYPE: DNA
<213> ORGANISM: Artificial Sequence
<220> FEATURE:
<223> OTHER INFORMATION: RRE/rabbit poly A beta globin

<400> SEQUENCE: 30

```
tctagaagga  gctttgttcc  ttgggttctt  gggagcagca  ggaagcacta  tgggcgcagc   60
gtcaatgacg  ctgacggtac  aggccagaca  attattgtct  ggtatagtgc  agcagcagaa  120
caatttgctg  agggctattg  aggcgcaaca  gcatctgttg  caactcacag  tctgggcat   180 caagcagctc  caggcaagaa  tcctggctgt  ggaaagatac  ctaaaggatc  aacagctcct  240
```

```
agatcttttt ccctctgcca aaaattatgg ggacatcatg aagccccttg agcatctgac    300
ttctggctaa taaaggaaat ttattttcat tgcaatagtg tgttggaatt ttttgtgtct    360
ctcactcgga aggacatatg ggagggcaaa tcatttaaaa catcagaatg agtatttggt    420
ttagagtttg gcaacatatg ccatatgctg gctgccatga acaaaggtgg ctataaagag    480
gtcatcagta tatgaaacag ccccctgctg tccattcctt attccataga aaagccttga    540
cttgaggtta gatttttttt atattttgtt ttgtgttatt tttttcttta acatccctaa    600
aattttcctt acatgtttta ctagccagat ttttcctcct ctcctgacta ctcccagtca    660
tagctgtccc tcttctctta tgaagatccc tcgacctgca gcccaagctt ggcgtaatca    720
tggtcatagc tgtttcctgt gtgaaattgt tatccgctca caattccaca acatacga     780 gccggaagca taaagtgtaa agcctggggt gcctaatgag tgagctaact cacattaatt    840
gcgttgcgct cactgcccgc tttccagtcg ggaaacctgt cgtgccagcg gatccgcatc    900
tcaattagtc agcaaccata gtcccgcccc taactccgcc catcccgccc taactccgc    960 ccagttccgc ccattctccg ccccatggct gactaatttt ttttatttat gcagaggccg    1020
aggccgcctc ggcctctgag ctattccaga agtagtgagg aggctttttt ggaggcctag    1080
gcttttgcaa aaagctaact tgtttattgc agcttataat ggttacaaat aaagcaatag    1140
catcacaaat ttcacaaata aagcattttt tcactgcat tctagttgtg ttgtccaa     1200 actcatcaat gtatcttatc acccggg                                        1227

<210> SEQ ID NO 31
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 31
ccggtgccta gagaaggtgg cgcggggtaa actgggaaag tgatgtcgtg tactggctcc     60 gccttttttcc cgagggtggg ggagaaccgt atataagtgc agtagtcgcc gtgaacgttc    120 ttttcgcaa cgggtttgcc gccagaacac aggtaagtgc cgtgtgtggt tcccgcgggc     180
ctggcctctt tacgggttat ggcccttgcg tgccttgaat tacttccacg cccctggctg    240
cagtacgtga ttcttgatcc cgagcttcgg gttggaagtg gtggggagag ttcgaggcct    300
tgcgcttaag gagccccttc gcctcgtgct tgagttgagg cctggcctgg gcgctggggc    360
cgccgcgtgc gaatctggtg gcaccttcgc gcctgtctcg ctgctttcga taagtctcta    420
gccatttaaa attttgatg acctgctgcg acgcttttt tctggcaaga tagtcttgta    480
aatgcgggcc aagatctgca cactggtatt tcggttttg gggccgcggg cggcgacggg    540
gcccgtgcgt cccagcgcac atgttcggcg aggcggggcc tgcgagcgcg ccaccgaga    600 atcggacggg ggtagtctca agctggccgg cctgctctgg tgcctggcct cgcgccgccg    660
tgtatcgccc cgccctgggc ggcaaggctg gcccggtcgg caccagttgc gtgagcggaa    720
agatggccgc ttcccggccc tgctgcaggg agctcaaaat ggaggacgcg gcgctcggga    780
gagcgggcgg gtgagtcacc cacacaaagg aaaagggcct ttccgtcctc agccgtcgct    840
tcatgtgact ccacggagta ccgggcgccg tccaggcacc tcgattagtt ctcgagcttt    900
tggagtacgt cgtctttagg ttgggggag gggtttatg cgatgagtt tccccacact    960 gagtgggtgg agactgaagt taggccagct tggcacttga tgtaattctc cttgaattt    1020 gcccttttg agtttggatc ttggttcatt ctcaagcctc agacagtggt tcaaagtttt    1080
```

```
tttcttccat tcaggtgtc gtga                                         1104
```

<210> SEQ ID NO 32
<211> LENGTH: 511
<212> TYPE: DNA
<213> ORGANISM: Artificial Sequence
<220> FEATURE:
<223> OTHER INFORMATION: Promoter - PGK

<400> SEQUENCE: 32

```
ggggttgggg ttgcgccttt tccaaggcag ccctgggttt gcgcagggac gcggctgctc    60
tgggcgtggt tccgggaaac gcagcggcgc cgaccctggg tctcgcacat tcttcacgtc   120
cgttcgcagc gtcacccgga tcttcgccgc tacccttgtg ggccccccgg cgacgcttcc   180
tgctccgccc ctaagtcggg aaggttcctt gcggttcgcg gcgtgccgga cgtgacaaac   240
ggaagccgca cgtctcacta gtaccctcgc agacggacag cgccagggag caatggcagc   300
gcgccgaccg cgatgggctg tggccaatag cggctgctca gcagggcgcg ccgagagcag   360
cggccgggaa ggggcggtgc gggaggcggg gtgtggggcg gtagtgtggg ccctgttcct   420
gcccgcgcgt tgttccgcat tctgcaagcc tccggagcgc acgtcggcag tcggctccct   480
cgttgaccga atcaccgacc tctctcccca g                                 511
```

<210> SEQ ID NO 33
<211> LENGTH: 1162
<212> TYPE: DNA
<213> ORGANISM: Artificial Sequence
<220> FEATURE:
<223> OTHER INFORMATION: Promoter - UbC

<400> SEQUENCE: 33

```
gcgccgggtt ttggcgcctc ccgcgggcgc cccctcctc acggcgagcg ctgccacgtc     60
agacgaaggg cgcaggagcg ttcctgatcc ttccgcccgg acgctcagga cagcggcccg   120
ctgctcataa gactcggcct tagaacccca gtatcagcag aaggacattt taggacggga   180
cttgggtgac tctagggcac tggttttctt tccagagagc ggaacaggcg aggaaaagta   240
gtcccttctc ggcgattctg cggagggatc tccgtggggc ggtgaacgcc gatgattata   300
taaggacgcg ccgggtgtgg cacagctagt tccgtcgcag ccgggatttg gtcgcggtt   360
cttgtttgtg gatcgctgtg atcgtcactt ggtgagttgc gggctgctgg gctggccggg   420
gctttcgtgg ccgccgggcc gctcggtggg acggaagcgt gtggagagac cgccaagggc   480
tgtagtctgg gtccgcgagc aaggttgccc tgaactgggg gttgggggga gcgcacaaaa   540
tggcggctgt tcccgagtct tgaatggaag acgcttgtaa ggcgggctgt gaggtcgttg   600
aaacaaggtg gggggcatgg tgggcggcaa gaacccaagg tcttgaggcc ttcgctaatg   660
cgggaaagct cttattcggg tgagatgggc tggggcacca tctgggacc ctgacgtgaa   720
gtttgtcact gactggagaa ctcggggttg tcgtctggtt gcggggggcgg cagtaatgcg   780
gtgccgttgg gcagtgcacc cgtacctttg ggagcgcgcg cctcgtcgtg tcgtgacgtc   840
acccgttctg ttggcttata atgcaggtgt gggccacctg ccggtaggtg tgcggtaggc   900
ttttctccgt cgcaggacgc agggttcggg cctagggtag gctctcctga atcgacaggc   960
gccggacctc tggtgagggg aggataagt gaggcgtcag tttctttggt cggttttatg   1020
tacctatctt cttaagtagc tgaagctccg gttttgaact atgcgctcgg ggttggcgag   1080
tgtgttttgt gaagtttttt aggcaccttt tgaaatgtaa tcatttgggt caatatgtaa   1140
```
ttttcagtgt tagactagta aa 1162

<210> SEQ ID NO 34
<211> LENGTH: 120
<212> TYPE: DNA
<213> ORGANISM: Artificial Sequence
<220> FEATURE:
<223> OTHER INFORMATION: Poly A - SV40

<400> SEQUENCE: 34
gtttattgca gcttataatg gttacaaata aagcaatagc atcacaaatt tcacaaataa 60
agcatttttt tcactgcatt ctagttgtgg tttgtccaaa ctcatcaatg tatcttatca 120

<210> SEQ ID NO 35
<211> LENGTH: 227
<212> TYPE: DNA
<213> ORGANISM: Artificial Sequence
<220> FEATURE:
<223> OTHER INFORMATION: Poly A - bGH

<400> SEQUENCE: 35
gactgtgcct tctagttgcc agccatctgt tgtttgcccc tcccccgtgc cttccttgac 60
cctggaaggt gccactccca ctgtcctttc ctaataaaat gaggaaattg catcgcattg 120
tctgagtagg tgtcattcta ttctgggggg tggggtgggg caggacagca agggggagga 180
ttgggaagac aatagcaggc atgctgggga tgcggtgggc tctatgg 227

<210> SEQ ID NO 36
<211> LENGTH: 1695
<212> TYPE: DNA
<213> ORGANISM: Artificial Sequence
<220> FEATURE:
<223> OTHER INFORMATION: Envelope - RD114

<400> SEQUENCE: 36
atgaaactcc caacaggaat ggtcattttta tgtagcctaa taatagttcg ggcagggttt 60
gacgaccccc gcaaggctat cgcattagta caaaaacaac atggtaaacc atgcgaatgc 120
agcggagggc aggtatccga ggccccaccg aactccatcc aacaggtaac ttgcccaggc 180
aagacggcct acttaatgac caaccaaaaa tggaaatgca gagtcactcc aaaaaatctc 240 accccctagcg ggggagaact ccagaactgc ccctgtaaca cttttccagga ctcgatgcac 300 agttcttgtt atactgaata ccggcaatgc agggcgaata taagacata ctacacggcc 360 accttgctta aaatacggtc tgggagcctc aacgaggtac agatattaca aaaccccaat 420
cagctcctac agtcccctttg taggggctct ataaatcagc ccgtttgctg gagtgccaca 480
gcccccatcc atatctccga tggtggagga cccctcgata ctaagagagt gtggacagtc 540
caaaaaaggc tagaacaaat tcataaggct atgcatcctg aacttcaata ccacccctta 600
gccctgccca agtcagaga tgaccttagc cttgatgcac ggacttttga tatcctgaat 660
accactttta ggttactcca gatgtccaat tttagccttg cccaagattg ttggctctgt 720
ttaaaactag gtaccectac ccctcttgcg atacccactc cctctttaac ctactcccta 780
gcagactccc tagcgaatgc ctcctgtcag attatacctc cctcttggt tcaaccgatg 840 cagttctcca actcgtcctg tttatcttcc cctttcatta acgatacgga acaaatagac 900
ttaggtgcag tcacctttac taactgcacc tctgtagcca atgtcagtag tcctttatgt 960
gccctaaacg ggtcagtctt cctctgtgga aataacatgg cataccccta tttaccccaa 1020
aactggacag gactttgcgt ccaagcctcc ctcctcccg acattgacat catcccgggg 1080

| | |
|---|---|
| gatgagccag tccccattcc tgccattgat cattatatac atagacctaa acgagctgta | 1140 |
| cagttcatcc ctttactagc tggactggga atcaccgcag cattcaccac cggagctaca | 1200 |
| ggcctaggtg tctccgtcac ccagtataca aaattatccc atcagttaat atctgatgtc | 1260 |
| caagtcttat ccggtaccat acaagattta caagaccagg tagactcgtt agctgaagta | 1320 |
| gttctccaaa ataggagggg actggaccta ctaacggcag aacaaggagg aatttgttta | 1380 |
| gccttacaag aaaaatgctg ttttatgct aacaagtcag gaattgtgag aaacaaaata | 1440 |
| agaaccctac aagaagaatt acaaaaacgc agggaaagcc tggcatccaa ccctctctgg | 1500 |
| accgggctgc agggctttct tccgtacctc ctacctctcc tgggacccct actcaccctc | 1560 |
| ctactcatac taaccattgg gccatgcgtt ttcaatcgat tggtccaatt tgttaaagac | 1620 |
| aggatctcag tggtccaggc tctggttttg actcagcaat atcaccagct aaaacccata | 1680 |
| gagtacgagc catga | 1695 |

<210> SEQ ID NO 37
<211> LENGTH: 2013
<212> TYPE: DNA
<213> ORGANISM: Artificial Sequence
<220> FEATURE:
<223> OTHER INFORMATION: Envelope - GALV

<400> SEQUENCE: 37

| | |
|---|---|
| atgcttctca cctcaagccc gcaccacctt cggcaccaga tgagtcctgg gagctggaaa | 60 |
| agactgatca tcctcttaag ctgcgtattc ggagacggca aaacgagtct gcagaataag | 120 |
| aacccccacc agcctgtgac cctcacctgg caggtactgt cccaaactgg ggacgttgtc | 180 |
| tgggacaaaa aggcagtcca gcccctttgg acttggtggc cctctcttac acctgatgta | 240 |
| tgtgccctgg cggccggtct tgagtcctgg gatatcccgg gatccgatgt atcgtcctct | 300 |
| aaaagagtta gacctcctga ttcagactat actgccgctt ataagcaaat cacctgggga | 360 |
| gccatagggt gcagctaccc tcgggctagg accaggatgg caaattcccc cttctacgtg | 420 |
| tgtccccgag ctggccgaac ccattcagaa gctaggaggt gtgggggggct agaatcccta | 480 |
| tactgtaaag aatggagttg tgagaccacg ggtaccgttt attggcaacc caagtcctca | 540 |
| tgggacctca taactgtaaa atgggaccaa atgtgaaat gggagcaaaa atttcaaaag | 600 |
| tgtgaacaaa ccgggctggtg taaccccctc aagatagact tcacagaaaa aggaaaactc | 660 |
| tccagagatt ggataacgga aaaacctggg gaattaaggt tctatgtata tggacaccca | 720 |
| ggcatacagt tgactatccg cttagaggtc actaacatgc cggttgtggc agtgggccca | 780 |
| gaccctgtcc ttgcggaaca gggacctcct agcaagcccc tcactctccc tctctcccca | 840 |
| cggaaagcgc cgcccacccc tctacccccg gcggctagtg agcaaacccc tcgggtgcat | 900 |
| ggagaaactg ttaccctaaa ctctccgcct cccaccagtg gcgaccgact ctttggcctt | 960 |
| gtgcagggg ccttcctaac cttgaatgct accaacccag ggccactaa gtcttgctgg | 1020 |
| ctctgtttgg gcatgagccc cccttattat gaagggatag cctcttcagg agaggtcgct | 1080 |
| tatacctcca accatacccg atgccactgg ggggcccaag gaaagcttac cctcactgag | 1140 |
| gtctccggac tcgggtcatg catagggaag gtgcctctta cccatcaaca tctttgcaac | 1200 |
| cagaccttac ccatcaattc ctctaaaaac catcagtatc tgctcccctc aaaccatagc | 1260 |
| tggtgggcct gcagcactgg cctcacccc tgcctctcca cctcagtttt taatcagtct | 1320 |
| aaagacttct gtgtccaggt ccagctgatc ccccgcatct attaccatc tgaagaaacc | 1380 |

| | |
|---|---|
| ttgttacaag cctatgacaa atcacccccc aggtttaaaa gagagcctgc ctcacttacc | 1440 |
| ctagctgtct tcctggggtt agggattgcg gcaggtatag gtactggctc aaccgcccta | 1500 |
| attaaagggc ccatagacct ccagcaaggc ctaaccagcc tccaaatcgc cattgacgct | 1560 |
| gacctccggg cccttcagga ctcaatcagc aagctagagg actcactgac ttccctatct | 1620 |
| gaggtagtac tccaaaatag gagaggcctt gacttactat tccttaaaga aggaggcctc | 1680 |
| tgcgcggccc taaagaaga gtgctgtttt tatgtagacc actcaggtgc agtacgagac | 1740 |
| tccatgaaaa aacttaaaga aagactagat aaaagacagt tagagcgcca gaaaaaccaa | 1800 |
| aactggtatg aagggtggtt caataactcc ccttggttta ctaccctact atcaaccatc | 1860 |
| gctgggcccc tattgctcct ccttttgtta ctcactcttg ggccctgcat catcaataaa | 1920 |
| ttaatccaat tcatcaatga taggataagt gcagtcaaaa ttttagtcct tagacagaaa | 1980 |
| tatcagaccc tagataacga ggaaaacctt taa | 2013 |

<210> SEQ ID NO 38
<211> LENGTH: 1530
<212> TYPE: DNA
<213> ORGANISM: Artificial Sequence
<220> FEATURE:
<223> OTHER INFORMATION: Envelope - FUG

<400> SEQUENCE: 38

| | |
|---|---|
| atggttccgc aggttctttt gtttgtactc cttctgggtt tttcgttgtg tttcgggaag | 60 |
| ttccccattt acacgatacc agacgaactt ggtccctgga gccctattga catacaccat | 120 |
| ctcagctgtc caaataacct ggttgtggag gatgaaggat gtaccaacct gtccgagttc | 180 |
| tcctacatgg aactcaaagt gggatacatc tcagccatca agtgaacgg ttcacttgc | 240 |
| acaggtgttg tgacagaggc agagacctac accaactttg ttggttatgt cacaaccaca | 300 |
| ttcaagagaa agcatttccg ccccacccca gacgcatgta gagccgcgta taactggaag | 360 |
| atggccggtg accccagata tgaagagtcc ctacacaatc catccccga ctaccactgg | 420 |
| cttcgaactg taagaaccac caaagagtcc ctcattatca tatccccaag tgtgacagat | 480 |
| ttggacccat atgacaaatc ccttcactca agggtcttcc ctggcggaaa gtgctcagga | 540 |
| ataacggtgt cctctaccta ctgctcaact aaccatgatt acaccatttg gatgcccgag | 600 |
| aatccgagac caaggacacc ttgtgacatt tttaccaata gcagagggaa gagagcatcc | 660 |
| aacgggaaca gacttgcgg ctttgtggat gaaagaggcc tgtataagtc tctaaaagga | 720 |
| gcatgcaggc tcaagttatg tggagttctt ggacttagac ttatggatgg aacatgggtc | 780 |
| gcgatgcaaa catcagatga gaccaaatgg tgccctccag atcagttggt gaatttgcac | 840 |
| gactttcgct cagacgagat cgagcatctc gttgtggagg agttagttaa gaaaagagag | 900 |
| gaatgtctgg atgcattaga gtccatcatg accaccaagt cagtaagttt cagacgtctc | 960 |
| agtcacctga aaacttgt cccagggttt ggaaaagcat ataccatatt caacaaaacc | 1020 |
| ttgatggagg ctgatgctca ctacaagtca gtccggacct ggaatgagat catcccctca | 1080 |
| aaagggtgtt tgaaagttgg aggaaggtgc catcctcatg tgaacgggt gttttttcaat | 1140 |
| ggtataatat tagggcctga cgaccatgtc ctaatcccag atgcaatc atccctcctc | 1200 |
| cagcaacata tggagttgtt ggaatcttca gttatccccc tgatgcaccc cctggcagac | 1260 |
| ccttctacag ttttcaaaga aggtgatgag gctgaggatt tgttgaagt tcacctcccc | 1320 |
| gatgtgtaca aacagatctc aggggttgac ctgggtctcc cgaactgggg aaagtatgta | 1380 |
| ttgatgactg caggggccat gattggcctg gtgttgatat tttccctaat gacatggtgc | 1440 |

```
agagttggta tccatctttg cattaaatta aagcacacca agaaaagaca gatttataca    1500
gacatagaga tgaaccgact tggaaagtaa                                     1530

<210> SEQ ID NO 39
<211> LENGTH: 1497
<212> TYPE: DNA
<213> ORGANISM: Artificial Sequence
<220> FEATURE:
<223> OTHER INFORMATION: Envelope - LCMV

<400> SEQUENCE: 39
atgggtcaga ttgtgacaat gtttgaggct ctgcctcaca tcatcgatga ggtgatcaac      60
attgtcatta ttgtgcttat cgtgatcacg ggtatcaagg ctgtctacaa ttttgccacc    120
tgtgggatat tcgcattgat cagtttccta cttctggctg caggtcctg tggcatgtac     180 ggtcttaagg gacccgacat ttacaaagga gtttaccaat ttaagtcagt ggagtttgat    240
atgtcacatc tgaacctgac catgcccaac gcatgttcag ccaacaactc ccaccattac    300
atcagtatgg ggacttctgg actagaattg accttcacca tgattccat catcagtcac     360 aacttttgca atctgacctc tgccttcaac aaaaagacct tgaccacac actcatgagt     420 atagtttcga gcctacacct cagtatcaga gggaactcca actataaggc agtatcctgc    480
gacttcaaca atggcataac catccaatac aacttgacta tctcagatcg acaaagtgct    540
cagagccagt gtagaacctt cagaggtaga gtcctagata tgtttagaac tgccttcggg    600
gggaaataca tgaggagtgg ctggggctgg acaggctcag atggcaagac cacctggtgt    660
agccagacga gttaccaata cctgattata caaaatagaa cctgggaaaa ccactgcaca    720
tatgcaggtc ctttttgggat gtccaggatt ctcctttccc aagagaagac taagttcttc    780
actaggagac tagcgggcac attcacctgg actttgtcag actcttcagg ggtggagaat    840
ccaggtggtt attgcctgac caaatggatg attcttgctg cagagcttaa gtgtttcggg    900
aacacagcag ttgcgaaatg caatgtaaat catgatgccg aattctgtga catgctgcga    960
ctaattgact acaacaaggc tgctttgagt aagttcaaag aggacgtaga atctgccttg    1020
cacttattca aaacaacagt gaattctttg atttcagatc aactactgat gaggaaccac    1080
ttgagagatc tgatgggggt gccatattgc aattactcaa agttttggta cctagaacat    1140
gcaaagaccg gcgaaactag tgtccccaag tgctggcttg tcaccaatgg ttcttactta    1200
aatgagaccc acttcagtga tcaaatcgaa caggaagccg ataacatgat tacagagatg    1260
ttgaggaagg attacataaa gaggcagggg agtaccccc tagcattgat ggaccttctg    1320
atgtttccca catctgcata tctagtcagc atcttcctgc accttgtcaa ataccaaca    1380 cacaggcaca taaaggtgg ctcatgtcca aagccacacc gattaaccaa caaaggaatt    1440
tgtagttgtg gtgcatttaa ggtgcctggt gtaaaaaccg tctggaaaag acgctga      1497

<210> SEQ ID NO 40
<211> LENGTH: 1692
<212> TYPE: DNA
<213> ORGANISM: Artificial Sequence
<220> FEATURE:
<223> OTHER INFORMATION: Envelope - FPV

<400> SEQUENCE: 40
atgaacactc aaatcctggt tttcgccctt gtggcagtca tccccacaaa tgcagacaaa     60
atttgtcttg gacatcatgc tgtatcaaat ggcaccaaag taaacacact cactgagaga    120
```

-continued

```
ggagtagaag ttgtcaatgc aacggaaaca gtggagcgga caaacatccc caaaatttgc    180
tcaaaaggga aaagaaccac tgatcttggc caatgcggac tgttagggac cattaccgga    240
ccacctcaat gcgaccaatt tctagaattt tcagctgatc taataatcga gagacgagaa    300
ggaaatgatg tttgttaccc ggggaagttt gttaatgaag aggcattgcg acaaatcctc    360
agaggatcag gtgggattga caaagaaaca atgggattca catatagtgg aataaggacc    420
aacggaacaa ctagtgcatg tagaagatca gggtcttcat tctatgcaga aatggagtgg    480
ctcctgtcaa atacagacaa tgctgctttc ccacaaatga caaaatcata caaaaacaca    540
aggagagaat cagctctgat agtctgggga atccaccatt caggatcaac caccgaacag    600
accaaactat atgggagtgg aaataaactg ataacagtcg ggagttccaa atatcatcaa    660
tcttttgtgc cgagtccagg aacacgaccg cagataaatg gccagtccgg acggattgat    720
tttcattggt tgatcttgga tcccaatgat acagttactt ttagtttcaa tggggctttc    780
atagctccaa atcgtgccag cttcttgagg ggaaagtcca tggggatcca gagcgatgtg    840
caggttgatg ccaattgcga aggggaatgc taccacagtg gagggactat aacaagcaga    900
ttgccttttc aaaacatcaa tagcagagca gttggcaaat gcccaagata tgtaaaacag    960
gaaagtttat tattggcaac tgggatgaag aacgttcccg aaccttccaa aaaaaggaaa   1020
aaaagaggcc tgtttggcgc tatagcaggg tttattgaaa atggttggga aggtctggtc   1080
gacgggtggt acggtttcag gcatcagaat gcacaaggag aaggaactgc agcagactac   1140
aaaagcaccc aatcggcaat tgatcagata accggaaagt taaatagact cattgagaaa   1200
accaaccagc aatttgagct aatagataat gaattcactg aggtggaaaa gcagattggc   1260
aatttaatta actggaccaa agactccatc acagaagtat ggtcttacaa tgctgaactt   1320
cttgtggcaa tggaaaacca gcacactatt gatttggctg attcagagat gaacaagctg   1380
tatgagcgag tgaggaaaca attaagggaa aatgctgaag aggatggcac tggttgcttt   1440
gaaatttttc ataaatgtga cgatgattgt atggctagta taaggaacaa tacttatgat   1500
cacagcaaat acagagaaga agcgatgcaa aatagaatac aaattgaccc agtcaaattg   1560
agtagtggct acaaagatgt gatactttgg tttagcttcg ggcatcatg ctttttgctt   1620 cttgccattg caatgggcct tgttttcata tgtgtgaaga acggaaacat gcggtgcact   1680
atttgtatat aa                                                       1692
```

<210> SEQ ID NO 41
<211> LENGTH: 1266
<212> TYPE: DNA
<213> ORGANISM: Artificial Sequence
<220> FEATURE:
<223> OTHER INFORMATION: Envelope - RRV

<400> SEQUENCE: 41

```
agtgtaacag agcactttaa tgtgtataag gctactagac catacctagc acattgcgcc     60
gattgcgggg acgggtactt ctgctatagc ccagttgcta tcgaggagat ccgagatgag    120
gcgtctgatg gcatgcttaa gatccaagtc tccgcccaaa taggtctgga caaggcaggc    180
acccacgccc acacgaagct ccgatatatg gctggtcatg atgttcagga atctaagaga    240
gattccttga gggtgtacac gtccgcagcg tgctccatac atgggacgat gggacacttc    300
atcgtcgcac actgtccacc aggcgactac ctcaaggttt cgttcgagga cgcagattcg    360
cacgtgaagg catgtaaggt ccaatacaag cacaatccat tgccggtggg tagagagaag    420
ttcgtggtta gaccacactt tggcgtagag ctgccatgca cctcatacca gctgacaacg    480
```

```
gctcccaccg acgaggagat tgacatgcat acaccgccag atataccgga tcgcaccctg    540
ctatcacaga cggcgggcaa cgtcaaaata acagcaggcg gcaggactat caggtacaac    600
tgtacctgcg gccgtgacaa cgtaggcact accagtactg acaagaccat caacacatgc    660
aagattgacc aatgccatgc tgccgtcacc agccatgaca aatggcaatt tacctctcca    720
tttgttccca gggctgatca gacagctagg aaaggcaagg tacacgttcc gttccctctg    780
actaacgtca cctgccgagt gccgttggct cgagcgccgg atgccaccta tggtaagaag    840
gaggtgaccc tgagattaca cccagatcat ccgacgctct tctcctatag gagtttagga    900
gccgaaccgc acccgtacga ggaatggggtt gacaagttct ctgagcgcat catcccagtg    960
acggaagaag ggattgagta ccagtggggc aacaacccgc cggtctgcct gtgggcgcaa   1020
ctgacgaccg agggcaaacc ccatggctgg ccacatgaaa tcattcagta ctattatgga   1080
ctataccccg ccgccactat tgccgcagta tccggggcga gtctgatggc cctcctaact   1140
ctggcggcca catgctgcat gctggccacc gcgaggagaa agtgcctaac accgtacgcc   1200
ctgacgccag gagcggtggt accgttgaca ctggggctgc tttgctgcgc accgagggcg   1260
aatgca                                                              1266

<210> SEQ ID NO 42
<211> LENGTH: 1938
<212> TYPE: DNA
<213> ORGANISM: Artificial Sequence
<220> FEATURE:
<223> OTHER INFORMATION: Envelope - MLV 10A1

<400> SEQUENCE: 42
atggaaggtc cagcgttctc aaaaccccct aaagataaga ttaacccgtg gaagtcctta     60
atggtcatgg gggtctattt aagagtaggg atggcagaga gcccccatca ggtctttaat    120
gtaacctgga gagtcaccaa cctgatgact gggcgtaccg ccaatgccac ctccctttta    180
ggaactgtac aagatgcctt cccaagatta tattttgatc tatgtgatct ggtcggagaa    240
gagtgggacc cttcagacca ggaaccatat gtcgggtatg gctgcaaata ccccggaggg    300
agaaagcgga cccggacttt tgacttttac gtgtgccctg gcataccgt aaaatcgggg    360 tgtggggggc aagagagggc tactgtggt gaatgggtt gtgaaaccac cggacaggct    420
tactggaagc ccacatcatc atgggaccta atctccctta gcgcggtaa cacccccctgg    480 gacacgggat gctccaaaat ggcttgtggc ccctgctacg acctctccaa gtatccaat    540 tccttccaag gggctactcg aggggggcaga tgcaacccctc tagtcctaga attcactgat    600
gcaggaaaaa aggctaattg ggacgggccc aaatcgtggg gactgagact gtaccggaca    660
ggaacagatc ctattaccat gttctccctg accgccagg tcctcaatat agggccccgc    720 atcccccattg ggcctaatcc cgtgatcact ggtcaactac ccccctcccg acccgtgcag    780
atcaggctcc ccaggcctcc tcagcctcct cctacaggcg cagcctctat agtccctgag    840
actgccccac cttctcaaca acctgggacg ggagacaggc tgctaaacct ggtagaagga    900
gcctatcagg cgcttaacct caccaatccc gacaagaccc aagaatgttg gctgtgctta    960
gtgtcgggac tccttatta cgaaggagta gcggtcgtgg gcacttatac caatcattct   1020
accgccccgg ccagctgtac ggccacttcc aacataagc ttaccctatc tgaagtgaca   1080
ggacagggcc tatgcatggg agcactacct aaaactcacc aggccttatg taacaccacc   1140
caaagtgccg gctcaggatc ctactacctt gcagcacccg ctggaacaat gtgggcttgt   1200
```

| | |
|---|---|
| agcactggat tgactccctg cttgtccacc acgatgctca atctaaccac agactattgt | 1260 |
| gtattagttg agctctggcc cagaataatt taccactccc ccgattatat gtatggtcag | 1320 |
| cttgaacagc gtaccaaata taagagggag ccagtatcgt tgaccctggc ccttctgcta | 1380 |
| ggaggattaa ccatgggagg gattgcagct ggaataggga cggggaccac tgccctaatc | 1440 |
| aaaacccagc agtttgagca gcttcacgcc gctatccaga cagacctcaa cgaagtcgaa | 1500 |
| aaatcaatta ccaacctaga aaagtcactg acctcgttgt ctgaagtagt cctacagaac | 1560 |
| cgaagaggcc tagatttgct cttcctaaaa gagggaggtc tctgcgcagc cctaaaagaa | 1620 |
| gaatgttgtt tttatgcaga ccacacggga ctagtgagag acagcatggc caaactaagg | 1680 |
| gaaaggctta atcagagaca aaaactattt gagtcaggcc aaggttggtt cgaagggcag | 1740 |
| tttaatagat cccctggtt taccaccta atctccacca tcatgggacc tctaatagta | 1800 |
| ctcttactga tcttactctt tggaccctgc attctcaatc gattggtcca atttgttaaa | 1860 |
| gacaggatct cagtggtcca ggctctggtt ttgactcaac aatatcacca gctaaaacct | 1920 |
| atagagtacg agccatga | 1938 |

<210> SEQ ID NO 43
<211> LENGTH: 2030
<212> TYPE: DNA
<213> ORGANISM: Artificial Sequence
<220> FEATURE:
<223> OTHER INFORMATION: Envelope - Ebola

<400> SEQUENCE: 43

| | |
|---|---|
| atgggtgtta caggaatatt gcagttacct cgtgatcgat tcaagaggac atcattcttt | 60 |
| ctttgggtaa ttatcctttt ccaaagaaca ttttccatcc cacttggagt catccacaat | 120 |
| agcacattac aggttagtga tgtcgacaaa ctggtttgcc gtgacaaact gtcatccaca | 180 |
| aatcaattga gatcagttgg actgaatctc gaagggaatg gagtggcaac tgacgtgcca | 240 |
| tctgcaacta aaagatgggg cttcaggtcc ggtgtcccac caaaggtggt caattatgaa | 300 |
| gctggtgaat gggctgaaaa ctgctacaat cttgaaatca aaaaacctga cgggagtgag | 360 |
| tgtctaccag cagcgccaga cgggattcgg ggcttcccc ggtgccggta tgtgcacaaa | 420 |
| gtatcaggaa cgggaccgtg tgccggagac tttgccttcc acaaagaggg tgctttcttc | 480 |
| ctgtatgacc gacttgcttc cacagttatc taccgaggaa cgactttcgc tgaaggtgtc | 540 |
| gttgcatttc tgatactgcc ccaagctaag aaggacttct tcagctcaca ccccttgaga | 600 |
| gagccggtca atgcaacgga ggacccgtct agtggctact attctaccac aattagatat | 660 |
| caagctaccg gttttggaac caatgagaca gagtatttgt tcgaggttga caatttgacc | 720 |
| tacgtccaac ttgaatcaag attcacacca cagtttctgc tccagctgaa tgagacaata | 780 |
| tatacaagtg ggaaaggag caataccacg ggaaaactaa tttggaaggt caaccccgaa | 840 |
| attgatacaa caatcgggga gtgggccttc tgggaaacta aaaaaacctc actagaaaaa | 900 |
| ttcgcagtga agagttgtct ttcacagctg tatcaaacag agccaaaaac atcagtggtc | 960 |
| agagtccggc gcgaacttct tccgacccag ggaccaacac aacaactgaa gaccacaaaa | 1020 |
| tcatggcttc agaaaattcc tctgcaatgg ttcaagtgca cagtcaagga agggaagctg | 1080 |
| cagtgtcgca tctgacaacc cttgccacaa tctccacgag tcctcaaccc ccacaaccca | 1140 |
| aaccaggtcc ggacaacagc acccacaata cacccgtgta taaacttgac atctctgagg | 1200 |
| caactcaagt tgaacaacat caccgcagaa cagacaacga cagcacagcc tccgacactc | 1260 |
| ccccccgccac gaccgcagcc ggacccctaa aagcagagaa caccaacacg agcaagggta | 1320 |

```
ccgacctcct ggaccccgcc accacaacaa gtccccaaaa ccacagcgag accgctggca   1380
acaacaacac tcatcaccaa gataccggag aagagagtgc cagcagcggg aagctaggct   1440
taattaccaa tactattgct ggagtcgcag gactgatcac aggcgggagg agagctcgaa   1500
gagaagcaat tgtcaatgct caacccaaat gcaaccctaa tttacattac tggactactc   1560
aggatgaagg tgctgcaatc ggactggcct ggataccata tttcgggcca gcagccgagg   1620
gaatttacat agaggggctg atgcacaatc aagatggttt aatctgtggg ttgagacagc   1680
tggccaacga gacgactcaa gctcttcaac tgttcctgag agccacaacc gagctacgca   1740 cctttcaat cctcaaccgt aaggcaattg atttcttgct gcagcgatgg ggcggcacat   1800
gccacatttt gggaccggac tgctgtatcg aaccacatga ttggaccaag aacataacag   1860
acaaaattga tcagattatt catgattttg ttgataaaac ccttccggac caggggggaca   1920 atgacaattg gtggacagga tggagacaat ggataccggc aggtattgga gttacaggcg   1980
ttataattgc agttatcgct ttattctgta tatgcaaatt tgtcttttag              2030
```

<210> SEQ ID NO 44
<211> LENGTH: 31
<212> TYPE: DNA
<213> ORGANISM: Artificial Sequence
<220> FEATURE:
<223> OTHER INFORMATION: Forward Primer to amplify Gag, Pol, and
      Integrase

<400> SEQUENCE: 44

```
taagcagaat tcatgaattt gccaggaaga t                                  31
```

<210> SEQ ID NO 45
<211> LENGTH: 36
<212> TYPE: DNA
<213> ORGANISM: Artificial Sequence
<220> FEATURE:
<223> OTHER INFORMATION: Reverse Primer to amplify Gag, Pol, and
      Integrase

<400> SEQUENCE: 45

```
ccatacaatg aatggacact aggcggccgc acgaat                             36
```

<210> SEQ ID NO 46
<211> LENGTH: 21
<212> TYPE: DNA
<213> ORGANISM: Artificial Sequence
<220> FEATURE:
<223> OTHER INFORMATION: KIF11 Forward Primer

<400> SEQUENCE: 46

```
ccgttctgga gctgttgata a                                             21
```

<210> SEQ ID NO 47
<211> LENGTH: 23
<212> TYPE: DNA
<213> ORGANISM: Artificial Sequence
<220> FEATURE:
<223> OTHER INFORMATION: KIF11 Reverse Primer

<400> SEQUENCE: 47

```
tgttctttct acaagggcag taa                                           23
```

<210> SEQ ID NO 48
<211> LENGTH: 24
<212> TYPE: DNA

```
<213> ORGANISM: Artificial Sequence
<220> FEATURE:
<223> OTHER INFORMATION: KIF11 TaqMan Probe (Fam/Iowa Black Zen
      quencher)

<400> SEQUENCE: 48
ccctgttgac tttgggaagg gtca                                         24

<210> SEQ ID NO 49
<211> LENGTH: 21
<212> TYPE: DNA
<213> ORGANISM: Artificial Sequence
<220> FEATURE:
<223> OTHER INFORMATION: Actin forward primer

<400> SEQUENCE: 49
ggacctgact gactacctca t                                            21

<210> SEQ ID NO 50
<211> LENGTH: 22
<212> TYPE: DNA
<213> ORGANISM: Artificial Sequence
<220> FEATURE:
<223> OTHER INFORMATION: Actin reverse primer #1

<400> SEQUENCE: 50
cgtagcacag cttctcctta at                                           22

<210> SEQ ID NO 51
<211> LENGTH: 22
<212> TYPE: DNA
<213> ORGANISM: Artificial Sequence
<220> FEATURE:
<223> OTHER INFORMATION: Actin reverse primer #2

<400> SEQUENCE: 51
attaaggaga agctgtgcta cg                                           22

<210> SEQ ID NO 52
<211> LENGTH: 20
<212> TYPE: DNA
<213> ORGANISM: Artificial Sequence
<220> FEATURE:
<223> OTHER INFORMATION: Actin probe (FAM or VIC/Iowa Black Zen)

<400> SEQUENCE: 52
agcgggaaat cgtgcgtgac                                              20

<210> SEQ ID NO 53
<211> LENGTH: 23
<212> TYPE: DNA
<213> ORGANISM: Artificial Sequence
<220> FEATURE:
<223> OTHER INFORMATION: Gag forward primer

<400> SEQUENCE: 53
ggagctagaa cgattcgcag tta                                          23

<210> SEQ ID NO 54
<211> LENGTH: 22
<212> TYPE: DNA
<213> ORGANISM: Artificial Sequence
<220> FEATURE:
<223> OTHER INFORMATION: Gag reverse primer

<400> SEQUENCE: 54
```

```
tgtagctgtc ccagtatttg tc                                           22

<210> SEQ ID NO 55
<211> LENGTH: 30
<212> TYPE: DNA
<213> ORGANISM: Artificial Sequence
<220> FEATURE:
<223> OTHER INFORMATION: Gag probe (FAM/Iowa Black Zen)

<400> SEQUENCE: 55
cctggcctgt tagaaacatc agaaggctgt                                   30

<210> SEQ ID NO 56
<211> LENGTH: 49
<212> TYPE: DNA
<213> ORGANISM: Artificial Sequence
<220> FEATURE:
<223> OTHER INFORMATION: Non-targeting shRNA sequence

<400> SEQUENCE: 56
gccgctttgt aggatagagc tcgagctcta tcctacaaag cggctttt               49
```